United States Patent
Hermez et al.

(10) Patent No.: US 10,814,093 B2
(45) Date of Patent: Oct. 27, 2020

(54) COMPONENTS FOR MEDICAL CIRCUITS

(71) Applicant: Fisher & Paykel Healthcare Limited, East Tamaki, Auckland (NZ)

(72) Inventors: Laith Adeeb Hermez, Auckland (NZ); Kieran Michael Orchard, Hawera (NZ); Timothy Dee Gierke, Wilmington, DE (US)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 16/352,219

(22) Filed: Mar. 13, 2019

(65) Prior Publication Data

US 2019/0209803 A1 Jul. 11, 2019

Related U.S. Application Data

(63) Continuation of application No. 13/517,925, filed as application No. PCT/IB2010/003454 on Dec. 22, 2010, now Pat. No. 10,532,177.

(Continued)

(51) Int. Cl.
*A61M 16/16* (2006.01)
*A61M 16/08* (2006.01)
(Continued)

(52) U.S. Cl.
CPC .......... *A61M 16/16* (2013.01); *A61M 13/003* (2013.01); *A61M 13/006* (2014.02);
(Continued)

(58) Field of Classification Search
CPC ................ A61M 16/142; A61M 16/04; A61M 16/0402; A61M 16/042; A61M 16/0461;
(Continued)

(56) References Cited

U.S. PATENT DOCUMENTS

| 928,237 | A | 7/1909 | Baird |
| 2,868,199 | A | 1/1959 | Hudson |

(Continued)

FOREIGN PATENT DOCUMENTS

| AU | 200013529 | 6/2000 |
| CA | 2833707 A | 11/2001 |

(Continued)

OTHER PUBLICATIONS

International Search Report dated May 23, 2011 for PCT Application No. PCT/IB2010/003454.

(Continued)

*Primary Examiner* — Tu A Vo
(74) *Attorney, Agent, or Firm* — Knobbe Martens Olson & Bear LLP

(57) ABSTRACT

Breathable medical circuit components and materials and methods for forming these components incorporate breathable foamed materials that are permeable to water vapor and substantially impermeable to liquid water and the bulk flow of gases. The materials and methods can be incorporated into a variety of components, including tubes, Y-connectors, catheter mounts, and patient interfaces and are suitable for use in a variety of medical circuits, including insufflation, anesthesia, and breathing circuits.

30 Claims, 27 Drawing Sheets

Related U.S. Application Data

(60) Provisional application No. 61/289,089, filed on Dec. 22, 2009.

(51) Int. Cl.
| | |
|---|---|
| *B29D 23/18* | (2006.01) |
| *A61M 13/00* | (2006.01) |
| *A61M 16/06* | (2006.01) |
| *A61M 16/10* | (2006.01) |
| *A61M 16/14* | (2006.01) |
| *A61M 16/00* | (2006.01) |
| *A61M 16/01* | (2006.01) |
| *B29L 23/18* | (2006.01) |

(52) U.S. Cl.
CPC .... *A61M 16/0057* (2013.01); *A61M 16/0069* (2014.02); *A61M 16/0093* (2014.02); *A61M 16/01* (2013.01); *A61M 16/021* (2017.08); *A61M 16/06* (2013.01); *A61M 16/0666* (2013.01); *A61M 16/08* (2013.01); *A61M 16/0875* (2013.01); *A61M 16/109* (2014.02); *A61M 16/1075* (2013.01); *A61M 16/1095* (2014.02); *A61M 16/142* (2014.02); *B29D 23/18* (2013.01); *A61M 16/009* (2013.01); *A61M 16/0683* (2013.01); *A61M 16/0833* (2014.02); *A61M 16/1045* (2013.01); *A61M 2016/103* (2013.01); *A61M 2205/02* (2013.01); *A61M 2205/3368* (2013.01); *A61M 2205/7536* (2013.01); *A61M 2207/00* (2013.01); *B29L 2023/18* (2013.01); *Y10T 428/1376* (2015.01)

(58) Field of Classification Search
CPC .. A61M 16/0465; A61M 16/08; A61M 16/16; A61M 1/00; A61M 39/00; A61M 16/0045; A61M 16/009; A61M 16/1045; A61M 16/105; A61M 16/106; A61M 16/1065; A61M 16/1095; A61M 16/22; B29L 2023/18; B29L 2031/7532; B29D 23/18; Y10T 428/1321; Y10T 428/1376; Y10T 428/24496; Y10T 428/12479; Y10T 428/233
See application file for complete search history.

(56) References Cited

U.S. PATENT DOCUMENTS

| | | |
|---|---|---|
| 3,376,181 A | 4/1968 | Larson |
| 3,394,954 A | 7/1968 | Sarns |
| 3,513,844 A | 5/1970 | Smith |
| 3,578,777 A | 5/1971 | DeGain |
| 3,616,796 A | 11/1971 | Jackson |
| 3,682,171 A | 8/1972 | Dali |
| 3,700,513 A | 10/1972 | Haberhauer |
| 3,735,558 A | 5/1973 | Skarstrom |
| 3,754,552 A | 8/1973 | King |
| 3,829,340 A | 8/1974 | Dembiak |
| 3,912,795 A * | 10/1975 | Jackson ............ A61M 16/04 261/36.1 |
| 4,035,211 A | 7/1977 | Bill |
| 4,083,245 A | 4/1978 | Osborn |
| 4,086,305 A | 4/1978 | Dobritz |
| 4,318,398 A | 3/1982 | Oetjen |
| 4,367,735 A | 1/1983 | Dali |
| 4,368,088 A | 1/1983 | Asakura |
| 4,403,514 A | 9/1983 | Osborn |
| 4,417,574 A | 11/1983 | Talonn |
| 4,493,870 A | 1/1985 | Vrouenraets |
| 4,509,359 A | 4/1985 | Gedeon |
| 4,580,816 A | 4/1986 | Campbell |
| 4,592,351 A | 6/1986 | Smith |
| 4,597,594 A | 7/1986 | Kacalieff |
| 4,621,632 A | 11/1986 | Bartels |
| 4,698,196 A | 10/1987 | Fabian |
| 4,705,543 A | 11/1987 | Kertzman |
| 4,715,915 A | 12/1987 | Vanderzee |
| 4,808,201 A | 2/1989 | Kertzman |
| 4,886,528 A | 12/1989 | Aaltonen |
| 4,910,384 A | 3/1990 | Silver |
| 4,915,104 A | 4/1990 | Marcy |
| 4,915,105 A | 4/1990 | Lee |
| 4,919,128 A | 4/1990 | Kopala |
| 4,932,269 A | 6/1990 | Cammarata |
| 4,938,752 A | 7/1990 | Vrouenraets |
| 4,967,744 A | 11/1990 | Chua |
| 4,985,055 A | 1/1991 | Thorne |
| 4,995,384 A | 2/1991 | Keeling |
| 5,042,500 A | 8/1991 | Norlien |
| 5,061,258 A | 10/1991 | Martz |
| 5,088,332 A | 2/1992 | Meriläinen |
| 5,233,996 A | 8/1993 | Coleman |
| 5,273,689 A | 12/1993 | Hamasaki |
| 5,308,337 A | 5/1994 | Bingisser |
| 5,335,656 A | 8/1994 | Bowe |
| 5,341,206 A | 8/1994 | Pittaro |
| 5,365,938 A | 11/1994 | Eskelä |
| 5,367,604 A | 11/1994 | Murray |
| 5,377,670 A | 1/1995 | Smith |
| 5,438,978 A | 8/1995 | Hardester |
| 5,438,979 A | 8/1995 | Johnson |
| 5,445,874 A | 8/1995 | Shehata |
| 5,445,875 A | 8/1995 | Persson |
| 5,501,212 A | 3/1996 | Psaros |
| 5,513,634 A | 5/1996 | Jackson |
| 5,532,053 A | 7/1996 | Mueller |
| 5,537,996 A | 7/1996 | McPhee |
| 5,558,087 A | 9/1996 | Psaros |
| 5,599,610 A | 2/1997 | Levy |
| 5,623,922 A | 4/1997 | Smith |
| 5,645,054 A | 7/1997 | Cotner |
| 5,715,647 A | 2/1998 | Keim |
| 5,738,808 A | 4/1998 | Iwamoto |
| 5,794,619 A | 8/1998 | Edelman |
| 5,823,184 A | 10/1998 | Gross |
| 5,850,833 A | 12/1998 | Kotliar |
| 5,862,652 A | 1/1999 | Schoeler |
| 6,033,368 A | 3/2000 | Gaston |
| 6,078,730 A | 6/2000 | Huddart et al. |
| 6,119,694 A | 9/2000 | Correa |
| 6,192,886 B1 | 2/2001 | Rudolph |
| 6,203,534 B1 | 3/2001 | Schoenholtz |
| 6,349,722 B1 | 2/2002 | Gradon |
| 6,431,172 B1 | 8/2002 | Bordewick |
| 6,523,538 B1 | 2/2003 | Wikefeldt |
| 6,584,972 B2 | 7/2003 | McPhee |
| 6,595,215 B2 | 7/2003 | Wood |
| 6,662,802 B2 | 12/2003 | Smith et al. |
| 6,684,883 B1 | 3/2004 | Burns |
| 6,718,973 B2 | 4/2004 | Koch |
| 6,742,399 B2 | 6/2004 | Kunz |
| 6,986,353 B2 | 1/2006 | Wright |
| 7,083,849 B1 | 8/2006 | Albrecht et al. |
| 7,140,366 B2 | 11/2006 | Smith et al. |
| 7,777,635 B2 | 8/2010 | Liu |
| 7,807,260 B2 | 10/2010 | Nadella et al. |
| 8,197,123 B2 * | 6/2012 | Snyder ............ G01K 7/16 374/1 |
| 8,453,681 B2 | 6/2013 | Forrester et al. |
| 10,532,177 B2 | 1/2020 | Hermez et al. |
| 10,603,460 B2 | 3/2020 | Hermez et al. |
| 2002/0002976 A1 | 1/2002 | Smith et al. |
| 2002/0059935 A1 | 5/2002 | Wood |
| 2002/0195104 A1 | 12/2002 | Fini et al. |
| 2003/0028139 A1 | 2/2003 | Inoue |
| 2003/0047185 A1 | 3/2003 | Olsen |
| 2003/0062048 A1 | 4/2003 | Gradon |
| 2003/0070680 A1 | 4/2003 | Smith et al. |
| 2003/0094178 A1 | 5/2003 | McAuley |
| 2003/0154977 A1 * | 8/2003 | White ............ A61M 16/1075 128/203.26 |

(56) References Cited

U.S. PATENT DOCUMENTS

| | | | |
|---|---|---|---|
| 2003/0207640 A1 | 11/2003 | Anderson et al. | |
| 2003/0213490 A1 | 11/2003 | Righetti | |
| 2004/0060609 A1 | 4/2004 | Fatato et al. | |
| 2004/0099268 A1 | 5/2004 | Smith et al. | |
| 2005/0009972 A1 | 1/2005 | Rauh et al. | |
| 2005/0150505 A1* | 7/2005 | Burrow | A61M 16/0816 128/204.18 |
| 2008/0027344 A1 | 1/2008 | Terry | |
| 2009/0020124 A1 | 1/2009 | Roth et al. | |
| 2009/0025724 A1 | 1/2009 | Herron, Jr. | |
| 2009/0026198 A1 | 1/2009 | Ichikawa et al. | |
| 2009/0107493 A1* | 4/2009 | Liu | A61M 16/1075 128/202.22 |
| 2009/0107980 A1* | 4/2009 | Andel | A61M 16/1075 219/443.1 |
| 2009/0107982 A1* | 4/2009 | McGhin | A61M 16/1075 219/497 |
| 2009/0233024 A1 | 9/2009 | Ballard et al. | |
| 2009/0305030 A1 | 12/2009 | Sriraman et al. | |
| 2010/0018534 A1 | 1/2010 | Veliss et al. | |
| 2012/0090622 A1 | 4/2012 | Chang | |
| 2013/0098360 A1 | 4/2013 | Hurmez et al. | |
| 2017/0296769 A1 | 10/2017 | Smith et al. | |
| 2018/0071477 A1 | 3/2018 | Smith et al. | |
| 2018/0071478 A1 | 3/2018 | Smith et al. | |

FOREIGN PATENT DOCUMENTS

| | | | |
|---|---|---|---|
| CA | 2346628 | 7/2010 | |
| CA | 2697142 C | 2/2014 | |
| EP | 0535379 | 4/1993 | |
| EP | 0557040 | 8/1993 | |
| EP | 0567158 | 10/1993 | |
| EP | 0579384 A1 * | 1/1994 | A61M 16/08 |
| EP | 0621050 | 10/1994 | |
| EP | 0747078 | 11/1996 | |
| EP | 0521726 | 1/1997 | |
| EP | 0815792 | 1/1998 | |
| EP | 0885623 | 12/1998 | |
| EP | 1014527 | 6/2000 | |
| EP | 1 166 814 A2 | 1/2002 | |
| EP | 1166814 | 1/2002 | |
| EP | 1516643 | 3/2005 | |
| EP | 1477200 | 10/2006 | |
| EP | 1153627 | 11/2007 | |
| EP | 1681071 | 2/2009 | |
| EP | 2305336 | 4/2011 | |
| EP | 2025359 | 9/2013 | |
| EP | 1524937 | 3/2016 | |
| GB | 9683 | 4/1909 | |
| GB | 587163 | 4/1947 | |
| GB | 1492459 | 11/1977 | |
| GB | 2024100 | 12/1982 | |
| GB | 2139110 | 11/1984 | |
| GB | 2252515 | 8/1992 | |
| GB | 2284356 | 10/1997 | |
| JP | S62-236724 | 10/1987 | |
| JP | H03-168155 | 7/1991 | |
| JP | H05-052378 | 3/1993 | |
| JP | H0623051 | 2/1994 | |
| JP | H09234247 | 9/1997 | |
| JP | 11323899 A | 11/1999 | |
| JP | 2000024111 | 1/2000 | |
| WO | WO 01/41854 | 6/1991 | |
| WO | WO 95/16746 | 6/1995 | |
| WO | WO 97/18001 | 5/1997 | |
| WO | WO 1997/18001 | 5/1997 | |
| WO | WO 98/02199 | 1/1998 | |
| WO | WO 98/41148 | 9/1998 | |
| WO | WO 99/64077 | 12/1999 | |
| WO | WO 00/48682 | 8/2000 | |
| WO | WO 01/49351 | 7/2001 | |
| WO | WO 2008/070929 A1 | 6/2008 | |
| WO | WO 2009/012049 A1 | 1/2009 | |
| WO | WO 2011/077250 A1 | 6/2011 | |

OTHER PUBLICATIONS

Extended European Search Report dated Feb. 4, 2015 for EP Application No. 10838780.4.
Highbeam.com, "Polyester elastomer cuts costs in VT films. (Thermoplastic elastomers)," Oct. 1, 2007.
Notification of First Office Action dated Apr. 1, 2014 for CN Application No. 201080063062.7.
Notification of Second Office Action dated Feb. 11, 2015 for CN Application No. 201080063062.7.
Search Opinion and Search Report dated May 23, 2014 for DK Application No. PA 2012 70445.
First Technical Examination of Patent Application and Search Report dated Dec. 1, 2014 for DK Application No. PA 2012 704445.
Technical Notice dated Jun. 11, 2013 for SE Application No. 1250881-8.
Technical Notice dated Oct. 2, 2014 for SE 1250881-8.
Notification of Reason for Rejection dated Sep. 26, 2014 in JP Application No. 2012-545470.
Breathable TPE Films for Medical Applications.
Dryers, Sampling Systems, dated Jan. 27, 1999, Perma Pure, www.permapure.com capture from archive.org.
Effect of Temperature on Water Vapor Transport Through Polymer Membrane Laminates, dated Feb. 1999, U.S. Army.
Flow separation in a diverging conical duct: Effect of Reynolds number and divergence angle, dated Jun. 2009 International Journal of Heat and Mass Transfer.
Gas Monitoring in Clinical Practice, 1995, Butterworth-Heinemann.
MBM-200 Deltatrac II™ Service Manual, dated Mar. 1, 1993, Datex/ Division of Instrumentarium Corp.
Measurement of water vapor diffusion through laminated fabrics and membranes using a diode laser spectroscope, Jan. 1998, U.S. Army.
Medical Gas Dryers, dated Oct. 17, 2000, Perma Pure, www.permapure.com capture from archive.org.
ME-Series Moisture Exchangers, Mar. 3, 2001, Perma Pure, www.permapure.com capture from archive.org.
MR700/MR720/MR730 Respiratory Humidifiers Operator's Manual, Printed Mar. 1998, Fisher & Paykel Healthcare.
On the Flow of Water through Pipes and Passages having Converging or Diverging Boundaries, Oct. 10, 2009, University College, Dundee.
Perma Pure Dryers Bulletin 104, No date, at least as early as Dec. 14, 1992, Perma Pure.
Smart Anesthesia Multi-Gas SAM®/SAM-80 Module Field Service Manual, dated Jul. 1, 2000, Marquette Medical Systems.
Thermoplastic Polyether Ester Elastomers, Supplied by British Library, date unknown.
File History of U.S. Pat. No. 5,501,212.
May 3, 2019 Complaint for Patent Infringement Demand for Jury Trial, *Fisher & Paykel Healthcare Limited* v. *Flexicare Incorporated*, Case No. 8:19-CV-00835.
Australian Patent Application No. 200143823 Published on Nov. 15, 2001 entitled Components for Breathing Circuits; Inventors Smith, Baldwin, Powell and Millar.
Canadian Examination Report for Application No. CA 2,697,142 dated Jun. 27, 2012; 2 pages.
European Search Report for Application No. 10184899.2 dated Mar. 7, 2011; 3 pages.
Canadian Office Action dated Mar. 11, 2015 for Canadian Application No. 2833707, 4 pages.
One page off the Perma Pure Inc. website of the product brochure #104 of the New PDTM—Series Gas Dryers.
Three pages off the SympaTex website of some of the most common questions that are asked and some technical data on the SympaTex membrane.

(56) References Cited

OTHER PUBLICATIONS

Claim Construction Order in the United States District Court of the Central District of California (Case No. 8:19-cv-00835-JVS-DFM) dated Mar. 27, 2020.

* cited by examiner

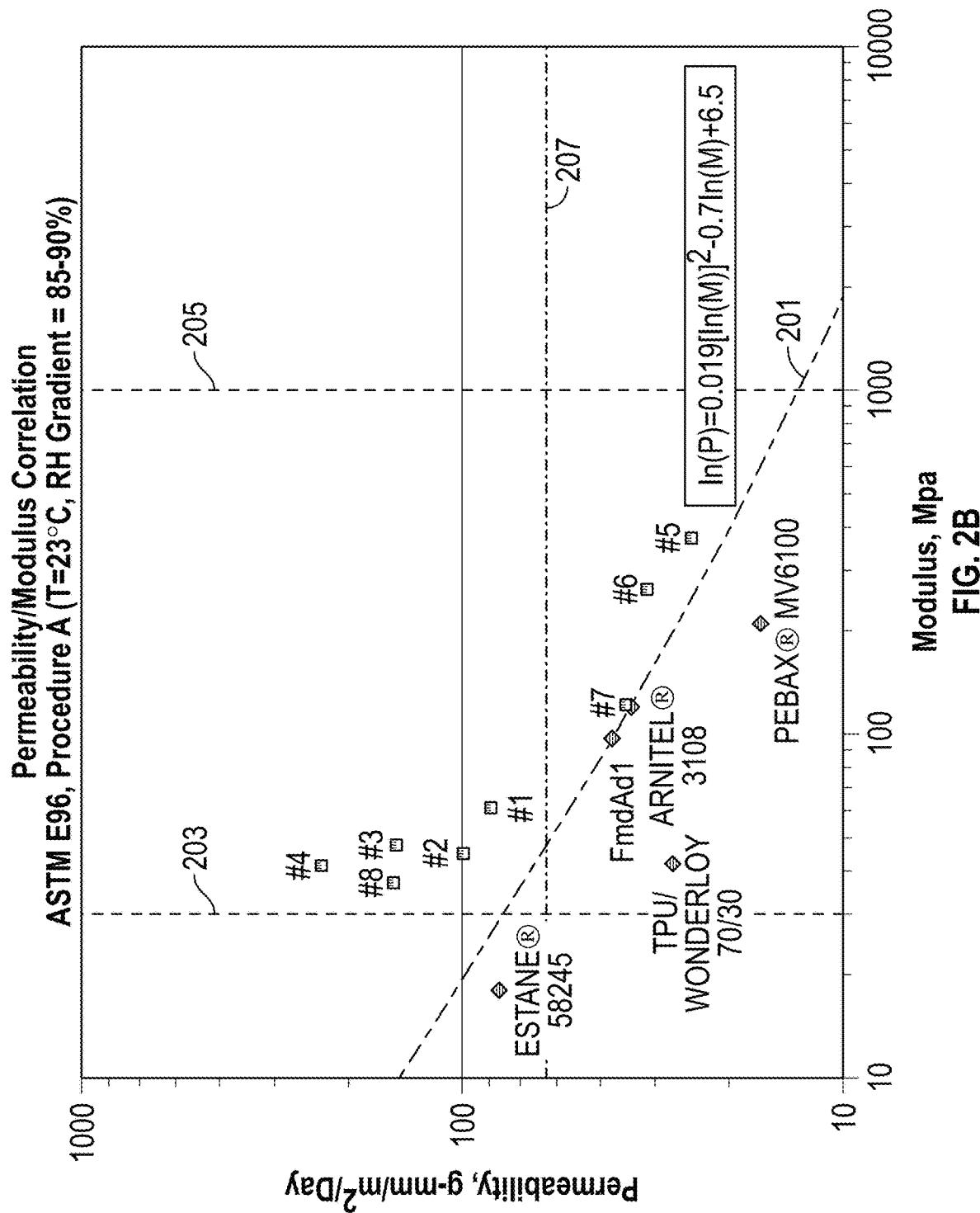

COMPONENTS FOR MEDICAL CIRCUITS

PRIORITY

This utility application is a continuation of U.S. patent application Ser. No. 13/517,925, filed Jun. 20, 2012, which is the U.S. national phase of International Application No. PCT/IB2010/003454, filed Dec. 22, 2010, which claims the benefit of U.S. Provisional Patent Application No. 61/289,089, filed Dec. 22, 2009, the entire contents of each of which are hereby incorporated by this reference.

BACKGROUND

Field

This disclosure relates generally to components for medical circuits, and in particular to components for medical circuits providing humidified gases to and/or removing humidified gases from a patient, such as in positive airway pressure (PAP), respirator, anaesthesia, ventilator, and insufflation systems.

Description of the Related Art

In medical applications, various components transport gases having high levels of relative humidity to and from patients. Condensation, or "rain out," can be a problem when the high humidity gases come into contact with the walls of a component at a lower temperature. However, condensation is dependent on many factors, including not only the temperature profile in the component, but also the gas flow rate, component geometry, and the intrinsic "breathability" of the material used to form the component, that is the ability of the material to transmit water vapor, while substantially resisting the bulk flow of liquid water and the bulk flow of gas.

For example, PAP systems (ventilation systems that provide patients with breathing gases at positive pressure) use breathing tubes for delivering and removing inspiratory and expiratory gases. In these applications, and in other breathing applications such as assisted breathing, the gases inhaled by a patient are usually delivered through an inspiratory tube at humidity near saturation. The breathing gases exhaled by a patient flow through an expiratory breathing tube and are usually fully saturated. Condensation may form on the interior walls of a breathing circuit component during patient inhalation, and significant condensation levels may form during patient exhalation. Such condensation is particularly deleterious when it is in close proximity to the patient. For instance, mobile condensate forming in a breathing tube (either inspiratory or expiratory) can be breathed or inhaled by a patient and may lead to coughing fits or other discomfort.

As another example, insufflation systems also deliver and remove humidified gases. During laparoscopic surgery with insufflation, it may be desirable for the insufflation gas (commonly $CO_2$) to be humidified before being passed into the abdominal cavity. This can help prevent "drying out" of the patient's internal organs, and can decrease the amount of time needed for recovery from surgery. Even when dry insufflation gas is employed, the gas can become saturated as it picks up moisture from the patient's body cavity. The moisture in the gases tends to condense out onto the walls of the discharge limb or tube of the insufflation system. The water vapor can also condense on other components of the insufflation system such as filters. Any vapor condensing on the filter and run-off along the limbs (inlet or exhaust) from moisture is highly undesirable. For example, water that has condensed on the walls can saturate the filter and cause it to become blocked. This potentially causes an increase in back pressure and hinders the ability of the system to clear smoke. Further, liquid water in the limbs can run into other connected equipment, which is undesirable.

Attempts have been made to reduce the adverse effects of condensation by incorporating highly "breathable" materials—that is, materials that are highly permeable to water vapor and substantially impermeable to liquid water and the bulk flow of gases—into the tube walls. However, this has required extremely thin membrane walls in order to achieve breathability sufficiently high to prevent or reduce condensation. As a result, tubes having acceptable breathability have had wall thicknesses so thin that the tubes need significant reinforcing measures. These reinforcing measures add time, cost, and complexity to the manufacturing process. Accordingly, a need remains for breathable, yet strong, components for medical circuits for delivering humidified gases.

SUMMARY

Materials and methods for forming breathable medical circuit components, such as breathable insufflation, anaesthesia, or breathing circuit components are disclosed herein in various embodiments. These breathable components incorporate breathable foamed materials that are permeable to water vapor and substantially impermeable to liquid water and the bulk flow of gases. The disclosed materials and methods can be incorporated into a variety of components, including tubes, Y-connectors, catheter mounts, and patient interfaces.

A medical circuit component for use with humidified gas is disclosed. In at least one embodiment, the component can comprise a wall defining a space within and wherein at least a part of said wall is of a breathable foamed material configured to allow the transmission of water vapor but substantially prevent the transmission of liquid water.

In various embodiments, the foregoing component has one, some, or all of the following properties. The diffusion coefficient of the breathable foamed material can be at least $3 \times 10^{-7}$ cm$^2$/s. The thickness of the wall can be between 0.1 mm and 3.0 mm. The breathable foamed material can comprise a blend of polymers. The breathable foamed material can comprise a thermoplastic elastomer with a polyether soft segment. The breathable foamed material can comprise a copolyester thermoplastic elastomer with a polyether soft segment. The breathable foamed material can be sufficiently stiff, such that the foamed material can be bent around a 25 mm diameter metal cylinder without kinking or collapse, as defined in the test for increase in flow resistance with bending according to ISO 5367:2000(E). The permeability P of the component in g-mm/m$^2$/day can be at least 60 g-mm/m$^2$/day when measured according to Procedure A of ASTM E96 (using the desiccant method at a temperature of 23° C. and a relative humidity of 90%). The elastic modulus of the component can be between 30 and 1000 MPa. The permeability P can satisfy the formula:

$$P > \exp\{0.019[\ln(M)]^2 - 0.7 \ln(M) + 6.5\}$$

in which M represents the elastic modulus of the foamed polymer in MPa and M is between 30 and 1000 MPa.

In addition, in various embodiments, the component according to any or all of the preceding embodiments has one, some, or all of the following properties. The foamed material can comprise voids. The foamed material can have a void fraction greater than 25%. The foamed material can have an average void size in the transverse direction less than 30% of the wall thickness. The foamed material can comprise voids that are flattened along the wall's longitudinal axis. At least 80% of the voids can have an aspect ratio of longitudinal length to transverse height greater than 2:1. At least 10% of the voids can be interconnected.

In certain embodiments, the component according to any or all of the preceding embodiments can form the wall of a tube or the wall of a mask. If the foamed material forms the wall of a tube, the tube can be, for example, an extruded tube, a corrugated tube, or an extruded, corrugated tube. Any of these foregoing tubes can be a tube for use in an insufflation system.

In at least one embodiment, the component can comprise a wall defining a space, wherein at least a part of the wall is of a foamed material that is permeable to water vapor and substantially impermeable to liquid water, wherein the permeability P of the foamed material measured according to Procedure A of ASTM E96 (using the desiccant method at a temperature of 23° C. and a relative humidity of 90%) in g-mm/m²/day is at least 60 g-mm/m²/day and satisfies the formula:

$$P > \exp\{0.019[\ln(M)]^2 - 0.7 \ln(M) + 6.5\}$$

wherein M represents the elastic modulus of the foamed material in MPa and M is between 30 and 1000 MPa.

In various embodiments, the foregoing component has one, some, or all of the following properties. P can be at least 70 g-mm/m²/day. M can be between 30 and 800 MPa. The wall thickness can be between 0.1 mm and 3.0 mm. The foamed material can have a void fraction greater than 25%. The foamed material can comprise voids. The foamed material can have an average void size in the transverse direction less than 30% of the wall thickness. At least some of the voids can be flattened along the wall's longitudinal axis. At least 80% of the voids can have an aspect ratio of longitudinal length to transverse height greater than 2:1. At least 10% of the voids can be interconnected. The breathable foamed material can comprise a thermoplastic elastomer with a polyether soft segment. The breathable foamed material can comprise a copolyester thermoplastic elastomer with a polyether soft segment.

In certain embodiments, the component according to any or all of the preceding embodiments can form the wall of a tube or the wall of a patient's mask. If the foamed material forms the wall of a tube, the tube can be, for example, an extruded tube, a corrugated tube, or an extruded, corrugated tube. Any of these foregoing tubes can be a tube for use in an insufflation system.

A method of manufacturing a medical circuit component is also disclosed. In at least one embodiment the method comprises mixing a foaming agent masterbatch (a mixture of a carrier polymer and active foaming agent) into a polymeric base material and forming a liquefied mixture, allowing the foaming agent portion to release gas bubbles into the base material portion of the liquefied mixture, and arresting the release of gas bubbles and processing the mixture to form a water-vapor permeable component.

In various embodiments, the foregoing method has one, some, or all of the following properties. The foaming agent and/or the polymeric base material can be selected and the mixture can be processed to form a water-vapor permeable component comprising a solid polymer and voids distributed throughout the solid polymer. The permeability P of the component in g-mm/m²/day can be at least 60 g-mm/m²/day or least 70 g-mm/m²/day measured according to Procedure A of ASTM E96 (using the desiccant method at a temperature of 23° C. and a relative humidity of 90%). The elastic modulus of the component can be between 30 and 1000 MPa. P can satisfy the formula:

$$P > \exp\{0.019[\ln(M)]^2 - 0.7 \ln(M) + 6.5\}$$

in which M represents the elastic modulus of the foamed polymer in MPa and M is between 30 and 1000 MPa, or between 30 and 800 MPa. The wall thickness can be between 0.1 mm and 3.0 mm.

In addition, in various embodiments, the method according to any or all of the preceding embodiments has one, some, or all of the following properties. The foamed material can comprise voids. The foamed material can have a void fraction greater than 25%. The average void size in the transverse direction can be less than 30% of the wall thickness. The foamed material can comprise voids that are flattened along the wall's longitudinal axis. At least 80% of the voids can have an aspect ratio of longitudinal length to transverse height greater than 2:1. At least 10% of the voids can be interconnected. The breathable foamed material can comprise a thermoplastic elastomer with a polyether soft segment. The breathable foamed material can comprise a copolyester thermoplastic elastomer with a polyether soft segment.

In certain embodiments, the method according to any or all of the preceding embodiments can comprise forming the water-vapor permeable component into a tube or forming the water vapor permeable component into a mask. If the method comprises forming the component into a tube, the act of processing the mixture can comprise extruding the mixture into a tube shape. Processing the mixture can also comprise co-extruding a plurality of reinforcing ribs on a surface of the tube shape. The ribs can be arranged on an inner surface of the tube shape, or on an outer surface of the tube shape, or on the inner and outer surface of the tube shape. In particular, the ribs can be arranged about the circumference of the tube shape, for example, circumferentially arranged about the inner surface of the tube shape. The ribs can be generally longitudinally aligned along a length of the tube shape. Processing the mixture can also comprise corrugating the extruded tube shape. If the extruded tube shape is corrugated, the tube shape can comprise ribs or the ribs can be omitted.

A tube for delivering humidified gas to or from a patient is also disclosed. In at least one embodiment, the tube comprises an inlet and an outlet and an extruded, corrugated, foamed-polymer conduit that is permeable to water vapor and substantially impermeable to liquid water and bulk flow of gas, the foamed-polymer conduit being configured to enable flow of humidified gas from the inlet to the outlet within a space enclosed by the conduit. The tube can further comprise a plurality of reinforcing ribs. The ribs can be arranged on an inner surface of the tube shape, or on an outer surface of the tube shape, or on the inner and outer surface of the tube shape. In particular, the ribs can be arranged about the circumference of the tube shape, for example, circumferentially arranged about the inner surface of the tube shape. The ribs can be generally longitudinally aligned along a length of the tube shape between the inlet and the outlet.

In various embodiments, the foregoing tubes, either with or without the above-described ribs, have one, some, or all of the following properties. The foamed-polymer conduit can comprise a solid thermoplastic elastomer material and cell voids distributed throughout the solid material. The foamed-polymer conduit can have an inner surface adjacent the enclosed space; and an inner volume adjacent the inner surface in which at least some of the cell voids are connected to other cell voids, thereby forming open cell pathways promoting movement of water vapor through the conduit. At least 10% or at least 20% of the cell voids can be connected to other cell voids. The inner volume can have a void fraction greater than 25%. The average void size in the transverse direction can be less than 30% of the wall thickness or less than 10% of the wall thickness. At least some of the voids can be flattened along a longitudinal axis of the conduit. The flattening can be expressed as having an aspect ratio of longitudinal length to transverse height greater than 2:1 or greater than 3:1. At least 80% of the voids can have the flattening.

In addition, in various embodiments, the tube according to any or all of the preceding embodiments has one, some, or all of the following properties. The foamed-polymer conduit can have a wall thickness between 0.1 mm and 3.0 mm. The permeability P of the component in g-mm/m$^2$/day can be at least 60 g-mm/m$^2$/day measured according to Procedure A of ASTM E96 (using the desiccant method at a temperature of 23° C. and a relative humidity of 90%). The elastic modulus of the component can be between 30 and 1000 MPa. P can satisfy the formula:

$$P > \exp\{0.019[\ln(M)]^2 - 0.7\ln(M) + 6.5\}$$

in which M represents the elastic modulus of the foamed polymer in MPa and M is between 30 and 1000 MPa. The foamed polymer conduit can be sufficiently stiff, such that the foamed polymer conduit can be bent around a 25 mm diameter metal cylinder without kinking or collapse, as defined in the test for increase in flow resistance with bending according to ISO 5367:2000(E).

In at least one embodiment, the tube comprises an inlet and an outlet and a foamed-polymer conduit that is permeable to water vapor and substantially impermeable to liquid water and bulk flow of gas, such that the foamed-polymer conduit enables flow of humidified gas from the inlet to the outlet within a space enclosed by the conduit, wherein the foamed-polymer conduit comprises a solid thermoplastic elastomer material and cell voids distributed throughout the solid material. The foamed-polymer conduit can have an inner surface adjacent the enclosed space; and an inner volume adjacent the inner surface. At least some of the cell voids in the inner volume can be connected to other cell voids, thereby forming open cell pathways promoting movement of water vapor through the conduit.

In various embodiments, the foregoing tubes have one, some, or all of the following properties. The foamed-polymer conduit can have a diffusion coefficient greater than $3 \times 10^{-7}$ cm$^2$/s. The conduit can be extruded. The conduit can be corrugated. The tube can further comprise a plurality of reinforcing ribs. The ribs can be arranged on an inner surface of the tube shape, or on an outer surface of the tube shape, or on the inner and outer surface of the tube shape. In particular, the ribs can be arranged about the circumference of the tube shape, for example, circumferentially arranged about the inner surface of the tube shape. The ribs can be generally longitudinally aligned along a length of the tube shape between the inlet and the outlet. The tube can comprise a heating line. The line can be generally longitudinally aligned along a length of the foamed-polymer conduit between the inlet and the outlet.

In addition, in various embodiments, the tube according to any or all of the preceding embodiments has one, some, or all of the following properties. At least 10% or at least 20% of the cell voids in the inner volume can be connected to other cell voids. The inner volume can have a void fraction greater than 25%. At least some of the voids can be flattened along a longitudinal axis of the conduit. The flattening can be expressed as having an aspect ratio of longitudinal length to transverse height greater than 2:1, or greater than 3:1. At least 80% of the voids can have the flattening. The inner volume can have an average void size in the transverse direction less than 30% or less than 10% of the foamed-polymer conduit wall thickness. The foamed-polymer conduit can have a wall thickness between 0.1 mm and 3.0 mm. The permeability P of the tube in g-mm/m$^2$/day can be at least 60 g-mm/m$^2$/day measured according to Procedure A of ASTM E96 (using the desiccant method at a temperature of 23° C. and a relative humidity of 90%). The elastic modulus of the tube can be between 30 and 1000 MPa P can satisfy the formula:

$$P > \exp\{0.019[\ln(M)]^2 - 0.7\ln(M) + 6.5\}$$

in which M represents the elastic modulus of the foamed polymer in MPa. The foamed polymer conduit can further have an outer skin adjacent the inner volume in which the cell voids are closed cell. The skin thickness can be between 5 and 10% of the wall thickness, for example, between 10 and 50 μm.

A method of manufacturing a tube suitable for delivering humidified gas to or from a patient is also disclosed. In at least one embodiment, the method comprises mixing a foaming agent into a base material to form an extrudate, the base material comprising one or more thermoplastic elastomers; applying pressure to the extrudate using an extruder to form a hollow tube; delivering the hollow tube to a corrugator mold; allowing the hollow tube to cool within the corrugator mold; and removing the cooled hollow tube from the corrugator, thereby forming a corrugated water-vapor permeable tube.

In various embodiments, the foregoing method has one, some, or all of the following properties. The tube can have a wall thickness between 0.1 mm and 3.0 mm. The corrugated tube can comprise solid thermoplastic elastomer and voids formed by the gas bubbles released by the foaming agent. The maximum void size diameter in the transverse direction can be less than one third of the minimum wall thickness. The void fraction of the corrugated tube can be greater than 25%. The base material can have a diffusion coefficient greater than $0.75 \times 10^{-7}$ cm$^2$/s. The base material can have a tensile modulus greater than 15 MPa.

A method of delivering humidified gas to or from a patient is also disclosed. In at least one embodiment, the method comprises providing a medical circuit component comprising a wall formed of breathable foamed material, connecting the medical circuit component to a patient, and transmitting humidified gas via the medical circuit component, wherein the medical circuit component allows for the passage of water vapor through the wall of the component but substantially prevents the transmission of liquid water and bulk flow of gas through the wall of the component.

In various embodiments, the foregoing method has one, some, or all of the following properties. The diffusion coefficient of the breathable foamed material can be at least $3 \times 10^{-7}$ cm$^2$/s. The thickness of the wall can be between 0.1 mm and 3.0 mm. The breathable foamed material can comprise a thermoplastic elastomer with a polyether soft segment. In particular, the breathable foamed material can comprise a copolyester thermoplastic elastomer with a polyether soft segment. The breathable foamed material can be sufficiently stiff, such that the foamed material can be bent around a 25 mm diameter metal cylinder without kinking or collapse, as defined in the test for increase in flow resistance with bending according to ISO 5367:2000(E). The permeability P of the component in g-mm/m²/day can be at least 60 g-mm/m²/day when measured according to Procedure A of ASTM E96 (using the desiccant method at a temperature of 23° C. and a relative humidity of 90%). The elastic modulus of the component can be between 30 and 1000 MPa. P can satisfy the formula:

$$P > \exp\{0.019[\ln(M)]^2 - 0.7 \ln(M) + 6.5\}$$

in which M represents the elastic modulus of the foamed polymer in MPa and M is between 30 and 1000 MPa.

In addition, in various embodiments, the method according to any or all of the preceding embodiments has one, some, or all of the following properties. The foamed material can comprise voids. At least 10% of the voids can be interconnected. The foamed material can have a void fraction greater than 25%. The foamed material can have an average void size in the transverse direction less than 30% of the wall thickness. At least some of the voids can be flattened along a longitudinal axis of the component. The flattening can be expressed as having an aspect ratio of longitudinal length to transverse height greater than 2:1 or greater than 3:1. At least 80% of the voids can have the flattening.

In certain embodiments, transmitting humidified gas via the medical circuit component can comprise transmitting humidified gas through a tube comprising the breathable foamed material, or transmitting humidified gas via a mask comprising the breathable foamed material, or transmitting humidified gas via an insufflation tube comprising the breathable foamed material.

The invention comprises all of the foregoing embodiments and also contemplates constructions of the following examples.

BRIEF DESCRIPTION OF THE DRAWINGS

Example embodiments that implement the various features of the disclosed systems and methods will now be described with reference to the drawings. The drawings and the associated descriptions are provided to illustrate embodiments and not to limit the scope of the disclosure.

FIG. 2B is a log/log plot of permeability vs. Young's modulus for previously known materials, and for breathable foamed polymer materials according to embodiments discussed herein.

FIGS. 4N and 4O are micrographs a non-foamed, extruded polymer strip.

Throughout the drawings, reference numbers are re-used to indicate correspondence between referenced (or similar) elements. In addition, the first digit of each reference number indicates the figure in which the element first appears.

DETAILED DESCRIPTION

The following detailed description discloses new materials and methods for forming breathable medical circuit components, such as breathable insufflation, anesthesia, or breathing circuit components. As explained above, these breathable components are permeable to water vapor and substantially impermeable to liquid water and the bulk flow of gases. The disclosed materials and methods can be incorporated into a variety of components, including tubes (e.g., inspiratory breathing tubes and expiratory breathing tubes and other tubing between various elements of a breathing circuit, such as ventilators, humidifiers, filters, water traps, sample lines, connectors, gas analyzers, and the like), Y-connectors, catheter mounts, and patient interfaces (e.g., masks for covering the nose and face, nasal masks, cannulas, nasal pillows, etc.), in a variety of medical circuits. Medical circuit is a broad term and is to be given its ordinary and customary meaning to a person of ordinary skill in the art (that is, it is not to be limited to a special or customized meaning). Thus, a medical circuit is meant to include open circuits, such as certain CPAP systems, which can comprise a single inspiratory breathing tube between a ventilator/blower and a patient interface, as well as closed circuits.

Breathing Circuit Comprising Breathable Components

Figure 1:
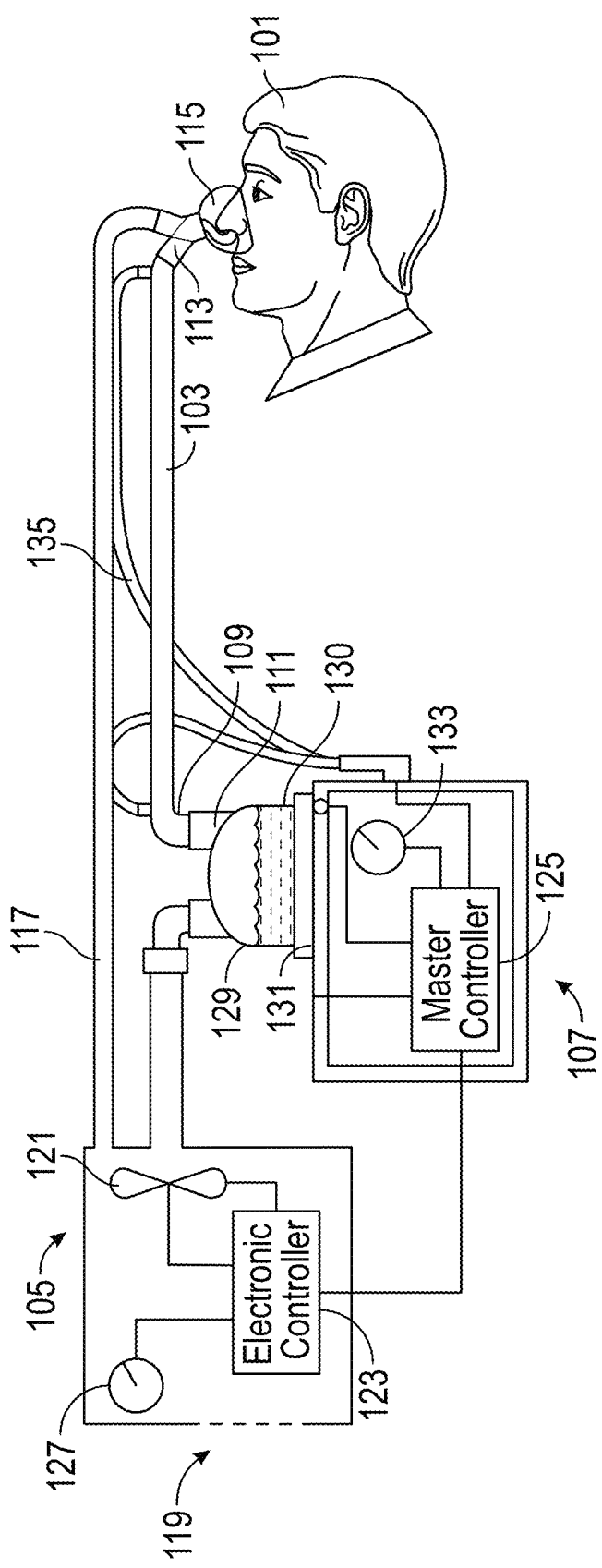
FIG. 1 is a schematic illustration of a medical circuit incorporating breathable components.

For a more detailed understanding of the disclosure, reference is first made to FIG. 1, which shows a breathing circuit according to at least one embodiment, which includes one or more breathable components. Such a breathing system can be a continuous, variable, or bi-level positive airway pressure (PAP) system or other form of respiratory therapy. In the example breathing circuit, a patient 101 receives humidified gas via a breathable inspiratory tube 103. Tube is a broad term and is to be given its ordinary and customary meaning to a person of ordinary skill in the art (that is, it is not to be limited to a special or customized meaning) and includes, without limitation, non-cylindrical passageways. An inspiratory tube is a tube that is configured to deliver humidified breathing gases to a patient. Breathable tubes are discussed in greater detail below.

Humidified gases can be transported in the circuit of FIG. 1 as follows. Dry gases pass from a ventilator/blower 105 to a humidifier 107, which humidifies the dry gases. The humidifier 107 connects to the inlet 109 (the end for receiving humidified gases) of the inspiratory tube 103 via a port 111, thereby supplying humidified gases to the inspiratory tube 103. The gases flow through the inspiratory tube 103 to the outlet 113 (the end for expelling humidified gases), and then to the patient 101 through a patient interface 115 connected to the outlet 113. An expiratory tube 117 also connects to the patient interface 115. An expiratory tube is a tube that is configured to move exhaled humidified gases away from a patient. Here, the expiratory tube 117 returns exhaled humidified gases from the patient interface 115 to the ventilator/blower 105.

In this example, dry gases enter the ventilator/blower 105 through a vent 119. A fan 121 can improve gas flow into the ventilator/blower by drawing air or other gases through vent 119. The fan 121 can be, for instance, a variable speed fan, where an electronic controller 123 controls the fan speed. In particular, the function of the electronic controller 123 can be controlled by an electronic master controller 125 in response to inputs from the master controller 125 and a user-set predetermined required value (preset value) of pressure or fan speed via a dial 127.

The humidifier 107 comprises a humidification chamber 129 containing a volume of water 130 or other suitable humidifying liquid. Preferably, the humidification chamber 129 is removable from the humidifier 107 after use. Removability allows the humidification chamber 129 to be more readily sterilized or disposed. However, the humidification chamber 129 portion of the humidifier 107 can be a unitary construction. The body of the humidification chamber 129 can be formed from a non-conductive glass or plastics material. But the humidification chamber 129 can also include conductive components. For instance, the humidification chamber 129 can include a highly heat-conductive base (for example, an aluminum base) contacting or associated with a heater plate 131 on the humidifier 107.

The humidifier 107 can also include electronic controls. In this example, the humidifier 107 includes an electronic, analog or digital master controller 125. Preferably, the master controller 125 is a microprocessor-based controller executing computer software commands stored in associated memory. In response to the user-set humidity or temperature value input via dial 133, for example, and other inputs, the master controller 125 determines when (or to what level) to energize heater plate 131 to heat the water 130 within humidification chamber 129.

Any suitable patient interface 115 can be incorporated. Patient interface is a broad term and is to be given its ordinary and customary meaning to a person of ordinary skill in the art (that is, it is not to be limited to a special or customized meaning) and includes, without limitation, masks (such as face masks and nasal masks), cannulas, and nasal pillows. A patient interface usually defines a gases space which, when in use, receives warm humid breathing gases and is therefore at risk of rain out forming. Due to the close proximity of the patient interface 115 to the patient 101, this is very undesirable. To address the risk of rain out, a temperature probe 135 can connect to the inspiratory tube 103 near the patient interface 115, or to the patient interface 115. The temperature probe 135 monitors the temperature near or at the patient interface 115. A heating line (not shown) communicating with the temperature probe can be used to adjust the temperature in the patient interface 115 and/or inspiratory tube 103 to raise the temperature in the inspiratory tube 103 and/or patient interface 115 above the saturation temperature. In addition to (or as an alternative to) a temperature probe and heating line, the patient interface 115 can also comprise a breathable interface, as described in greater detail below with respect to FIGS. 11A, 11B, and 12.

In FIG. 1, exhaled humidified gases are returned from the patient interface 115 to the ventilator/blower 105 via the expiratory tube 117. The expiratory tube 117 preferably comprises a breathable foamed material, as described below. However, the expiratory tube 117 can also be a medical tube as previously known in the art. In either case, the expiratory tube 117 can have a temperature probe and/or heating line, as described above with respect to the inspiratory tube 103, integrated with it to reduce the risk of rain out. Furthermore, the expiratory tube 117 need not return exhaled gases to the ventilator/blower 105. Alternatively, exhaled humidified gases can be passed directly to ambient surroundings or to other ancillary equipment, such as an air scrubber/filter (not shown). In certain embodiments, the expiratory tube is omitted altogether.

Foamed Polymers for Forming Breathable Components

As explained above with respect to FIG. 1, medical circuits such as breathing circuits can make use of breathable components, such as tubes or patient interfaces. Breathability is desirable to prevent rain out in these components. One measure of the material breathability is permeability (expressed in g-mm/m²/day). Another measure of breathability is the diffusivity of water in the material (diffusion coefficient, measured in cm²/sec). At similar test conditions, for example at similar temperatures, a given material's permeability and diffusivity are directly proportional to each other. It is known that breathable thermoplastic elastomer materials (TPE according to ISO 18064:2003(E), which is hereby incorporated in its entirety by this reference) are particularly suited to forming these breathable components.

However, these known materials are flimsy and require substantial reinforcement to render them usable.

It was found that the breathability-to-strength relationship can be unexpectedly improved by foaming polymer materials, including previously known breathable polymers, as they are formed into components. By incorporating highly breathable foamed material, components can be manufactured having both a relatively high flexural stiffness and a high breathability. Similarly, components formed from the foamed material described herein can also have relatively high resistance to crushing and resistance to buckling. As a result, it is possible to manufacture tubes with adequate "bulk" properties (for example, thickness, material, material blending, elastic modulus, breathability, and/or bulk stiffness) to meet the requirements of the ISO 5367:2000(E) standard (namely, the test for increase in flow resistance) without extra reinforcing, and also to be sufficiently breathable as defined in more detail later. ISO 5367:2000(E) is hereby incorporated in its entirety by this reference. For instance, it has been found that breathable thermoplastic elastomer (TPE) materials, such as ARNITEL® VT 3108, are particularly suited to foaming and forming components according various embodiments. For this material, the breathability-to-strength relationship can be significantly improved by foaming the material as it is formed into a product or component.

Thus, certain embodiments include the realization that particular foamed polymers can be used to form breathable components, such that the components have combined Young's modulus (stiffness) and permeability (breathability) properties that are significantly improved over previously known breathable materials. These new foamed polymers and techniques for forming the foamed polymers and medical circuit components incorporating such foamed polymers are described herein as illustrative examples. Because of their high permeability, these foamed polymers allow water vapor to diffuse through them rapidly. This reduces the build up of condensation within the component by transmitting water vapor from the humidified gases within the component to the surrounding ambient air or to other drier gases on the other side of the component. Yet, the components formed from these foamed polymers are also stiff, self supporting, crush resistant, or semi-rigid, and even may not require additional reinforcement. The foamed polymers are useful for forming medical circuit components because the foamed polymer allow the transmission of water vapor from gases, but prevent the transmission of liquid water. They are also substantially impermeable to the bulk flow of gas, such that they can be used to form components for delivering humidified gases.

In general, the foamed polymer according to at least one embodiment is a breathable foamed thermoplastic polymer. Preferably, the breathable thermoplastic polymer is a foamed thermoplastic elastomer (or TPE as defined by ISO 18064:2003(E)), such as (1) a copolyester thermoplastic elastomer (e.g., ARNITEL®, which is a copolyester thermoplastic elastomer with a polyether soft segment, or other TPC or TPC-ET materials as defined by ISO 18064:2003(E)), or (2) a polyether block amide (e.g., PEBAX®, which is a polyamide thermoplastic elastomer with a polyether soft segment, or other TPA-ET materials as defined by ISO 18064:2003(E)), or (3) a thermoplastic polyurethane (TPU material as defined by ISO 18064:2003(E)), or (4) a foamed polymer blend, such as a TPE/polybutylene terephthalate (PBT, e.g., DURANEX® 500FP) blend. If the breathable thermoplastic polymer is a foamed TPE/PBT blend, the blend preferably comprises between 80% and 99% (or about 80% and 99%) TPE by weight and 20% and 1% (or about 20% and 1%) PBT by weight.

In any of the above embodiments, the void fraction of the foamed material can be greater than 25% (or about 25%), such as between 25 and 60% (or about 25 and 60%), or between 30 and 50% (or about 30 and 50%). In at least one embodiment, no more than 5% (or about 5%) of the voids of said foamed material exceed a diameter of 500 µm.

Figure 2A:
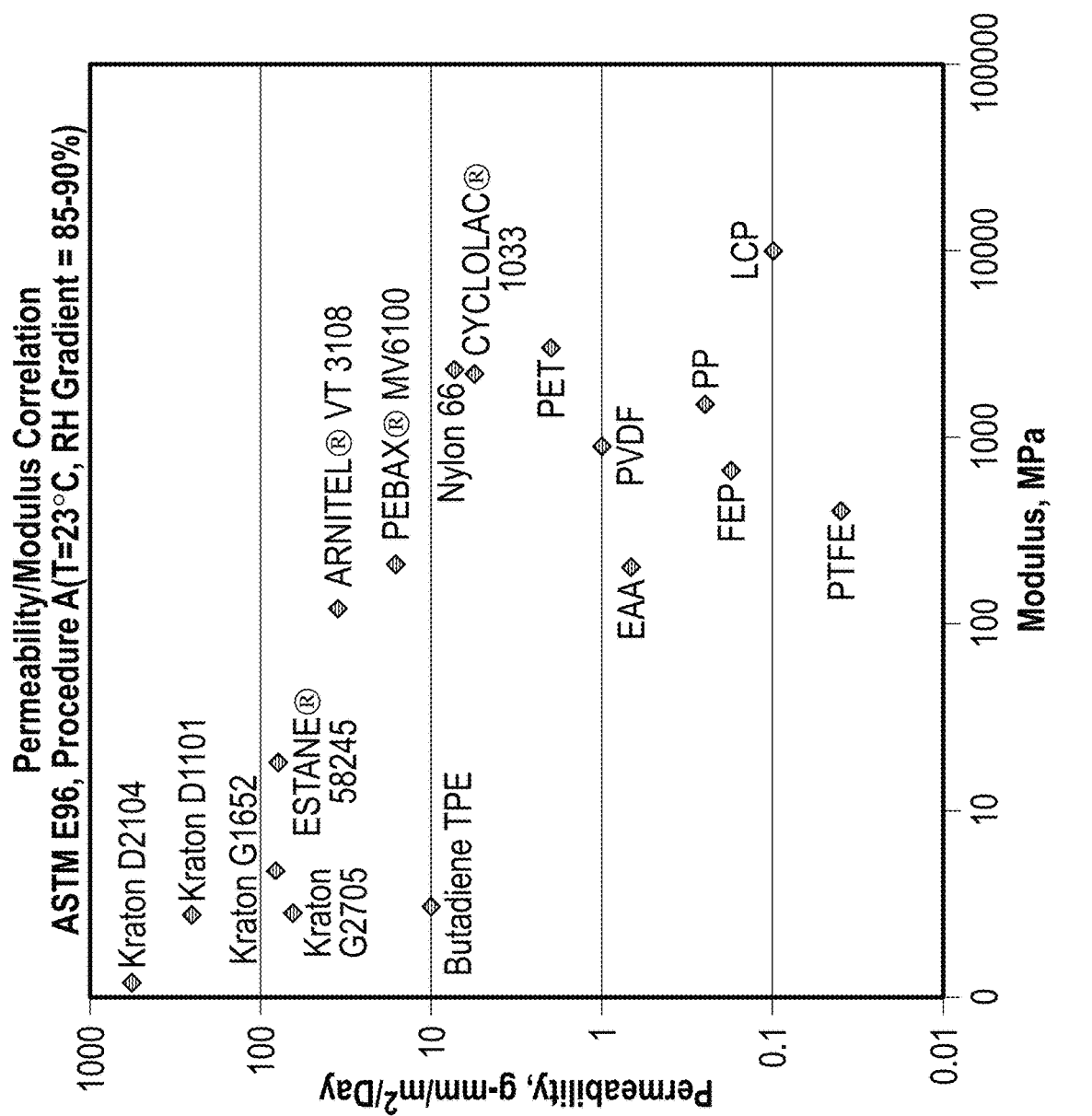
FIG. 2A is a log/log plot of permeability versus Young's modulus for several previously known breathable materials used for components in medical circuits.

FIG. 2A shows a log/log plot of literature values of permeability versus Young's modulus for breathable materials previously known in the art. The values vary over six orders of magnitude in both modulus and permeability.

FIG. 2B adds to FIG. 2A data points for examples of example foamed polymers according to various embodiments disclosed herein, labelled #1 through #4 and #6. It was discovered that the combined permeability and modulus for all the previously known materials did not exceed line 201, representing the formula:

$$\ln(P) > 0.019(\ln(M))^2 - 0.7 \ln(M) + 6.5$$

in which P represents permeability of the material in g·mm/m²/day, measured according to ASTM E96 Procedure A (desiccant method at a temperature of 23° C. and a relative humidity of 90%), and M represents the Young's modulus of the material in MPa. ASTM E96 is hereby incorporated in its entirety by this reference.

For the foamed polymer materials represented by points #1 through #4, #6, and #8 in FIG. 2B, permeability P satisfies the formula:

$$P > \exp\{0.019[\ln(M)]^2 - 0.7 \ln(M) + 6.5\}$$

Thus, these foamed polymers have combined levels of breathability and stiffness not previously known.

The permeability and modulus of a foamed polymer can be selected to provide improved stiffness and/or breathability in components incorporating the foamed polymer. Preferably, the material should be stiff enough to not easily crush or kink or change volume with pressure. For example, the breathable foamed polymer should be sufficiently stiff, such that the foamed polymer can be bent around a 25 mm diameter metal cylinder without kinking or collapse, as defined in the test for increase in flow resistance with bending according to ISO 5367:2000(E). Therefore, modulus M is greater than 30 MPa (or about 30 MPa) in at least one embodiment. The line M=30 MPa is indicated on FIG. 2B as line 203. However, it may also be desirable to limit the stiffness of the component, to make the component easier to handle or improve patient comfort. Therefore, modulus M can be limited in certain embodiments to less than 1000 MPa (or about 1000 MPa). The line M=1000 MPa is indicated as line 205. It may also be desirable to limit the modulus M to less than 800 MPa (or about 800 MPa), or less than 500 MPa (or about 500 MPa).

Figure 3:
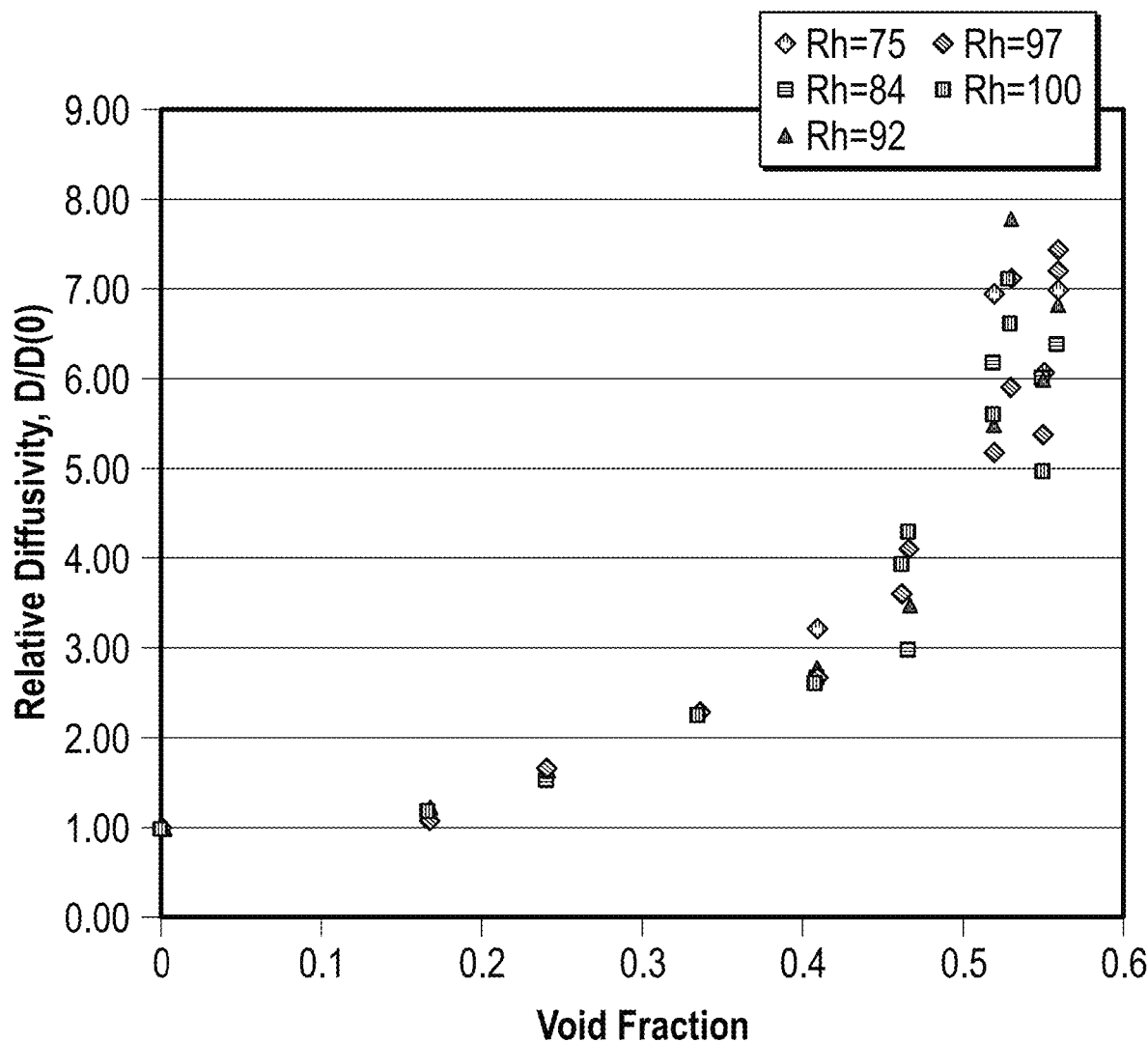
FIG. 3 is a plot of relative diffusivity versus void fraction in breathable foamed polymer materials according to embodiments discussed herein.

In addition, it may be desirable to select a breathability sufficiently high to prevent condensation in a variety of common uses and medical components. It was discovered that the diffusivity of a foamed polymer is function of void volume fractions. This is illustrated in TABLE 1, which summarizes at each relative humidity (RH) the ratio of the diffusivity at a specific void fraction (D) divided by the diffusivity, at the same RH, of solid ARNITEL® VT 3108 ($D_0$). The plot of the data in TABLE 1 is shown in FIG. 3.

TABLE 1

VALUES OF RELATIVE DIFFUSIVITY D/D$_0$

| Point # | Sample Name | Void Fraction | RH = 100 | RH = 97 | RH = 92 | RH = 84 | RH = 75 | RH = 69 |
|---|---|---|---|---|---|---|---|---|
|  | FmdAd1 | 0.168 | 1.18 | 1.09 | 1.19 | 1.17 |  |  |
| 1 | AB-14.2 | 0.337 | 2.25 | 2.26 | 2.27 |  |  |  |
| 2 | MB 27 4% | 0.41 | 2.61 | 2.68 | 2.73 | 2.64 | 3.21 |  |
| 3 | FIIA-2 | 0.466 | 4.28 | 4.11 | 3.45 | 2.95 |  |  |
| 4 | FIIA-5 | 0.53 | 6.60 | 7.13 | 7.79 |  |  |  |
| 4 | FIIA-5 | 0.53 | 7.08 | 5.90 |  |  |  |  |
| 7 | FIIA-1 | 0 | 1.00 | 1.00 | 1.00 | 1.00 | 1.00 | 1.00 |
|  | Batch 15 wts | 0.56 |  | 7.19 |  |  |  |  |
|  | Batch 15 wts | 0.56 |  | 7.44 | 6.83 | 6.36 | 6.98 |  |
|  | Batch 15 f | 0.55 | 4.97 | 5.37 | 6.02 | 5.99 | 6.06 |  |
|  | MB 27 6% | 0.52 | 5.60 | 5.19 | 5.52 | 6.17 | 6.95 |  |
|  | MB 41.4 | 0.462 | 3.91 | 3.59 | 3.74 | 4.06 |  |  |
|  | MB 22.1 | 0.241 |  | 1.65 | 1.66 | 1.56 |  |  |

Accordingly, it is possible to select an appropriate level of permeability and/or void fraction for the foamed polymer to define an appropriate breathability. In certain embodiments, permeability P is greater than 60 g-mm/m$^2$/day (or about 60 g-mm/m$^2$/day), measured according to ASTM E96 Procedure A. A permeability of 60 g-mm/m$^2$/day represents a 66% increase over solid ARNITEL® VT 3108. The line P=60 g-mm/m$^2$/day is indicated as line 207. It may also be desirable to select a permeability P greater than 70 MPa g-mm/m$^2$/day (or about 70 g-mm/m$^2$/day) in some embodiments.

It is possible to relate permeability to a corresponding void fraction. A permeability of 60 g-mm/m$^2$/day is 1.66 times the value of solid ARNITEL® VT 3108. Knowing that permeability is directly proportional to diffusivity, then it is possible to seek a corresponding void fraction where the diffusivity ratio is greater than 1.66 from FIG. 3. From FIG. 3, the corresponding void fraction is greater than 25%. Accordingly, in certain embodiments, void fraction is greater than 25% (or about 25%). It may also be desirable to select a void fraction greater than 30% (or about 30%) in some embodiments. A void fraction of 30% corresponds with a permeability of 70 g-mm/m$^2$/day (or about 70 g-mm/m$^2$/day), as explained above.

It can also be desirable to limit the void fraction in the foamed polymer, to prevent liquid water from leaking through the voids. If the foamed polymer does not have an outer skin structure (discussed in greater detail below), then it may be desirable to have a void fraction less than 45% (or about 45%). If the foamed polymer has an outer skin structure, then a void fraction less than 60% (or about 60%) may be suitable. It has been found that a void fraction between 25 and 60% (or about 25 and 60%) for foamed ARNITEL® VT 3108 is suitable for forming components for medical circuits as described herein. For example, a void fraction of 30% (or thereabout) can improve the breathability of Arnitel VT3108 by up to 2 times. A relatively modest modulus decrease can be offset by added thickness of the component as described below, while still maintaining a similar breathability. It has been found that a void fraction between 30 and 50% (or about 30 and 50%) of foamed ARNITEL® VT 3108 is particularly well suited for forming these components. It will be appreciated that the foregoing are only examples of suitable void fraction percentages and the corresponding material properties.

As discussed above, another measure of the material breathability is the diffusivity of water in the material (diffusion coefficient, measured in cm$^2$/sec). At similar test conditions, permeability and diffusivity are directly proportional to each other for a specific base material. In various embodiments, the foamed polymer has a diffusion coefficient greater than 3×10$^{-7}$ cm$^2$/s (or thereabout), and more preferably greater than 6×10$^{-7}$ cm$^2$/s (or thereabout). For example, a 0.1625 cm diameter rod of foamed ARNITEL® VT 3108 at 47% void fraction has been calculated to have a diffusion coefficient equal to (or about equal to) 7.6×10$^{-7}$ cm$^2$/s. As another example, a 0.0505 cm thick film of foamed ARNITEL® VT 3108 at 13% void fraction has been calculated to have a diffusion coefficient equal to (or about equal to) 3.3×10$^{-7}$ cm$^2$/sec.

Samples #1 through #4 in FIG. 2B comprise foamed ARNITEL® VT 3108. It can be seen that these materials, and particularly sample #4 at 53% void fraction, perform better than any other previously known material in terms of their combined permeability and modulus. For sample #4, the foaming process resulted in nearly a 6.5-fold average increase in permeability at 97% RH, while still having a modulus 30% of pure ARNITEL® VT 3108.

In FIG. 2B, point #1 represents data for a sample named "AB 14.2a." AB 14.2a is a foamed, corrugated ARNITEL® VT 3108 adult tube with an outer diameter of 24.5 cm. Experimental data collected on this sample include photomicrographs (shown in FIGS. 4A through 4D and summarized in TABLE 2), void fraction and average sample thickness (shown in TABLE 3), modulus (shown in TABLE 4), and the variation of diffusivity with RH (summarized in TABLE 1).

Figure 4A:
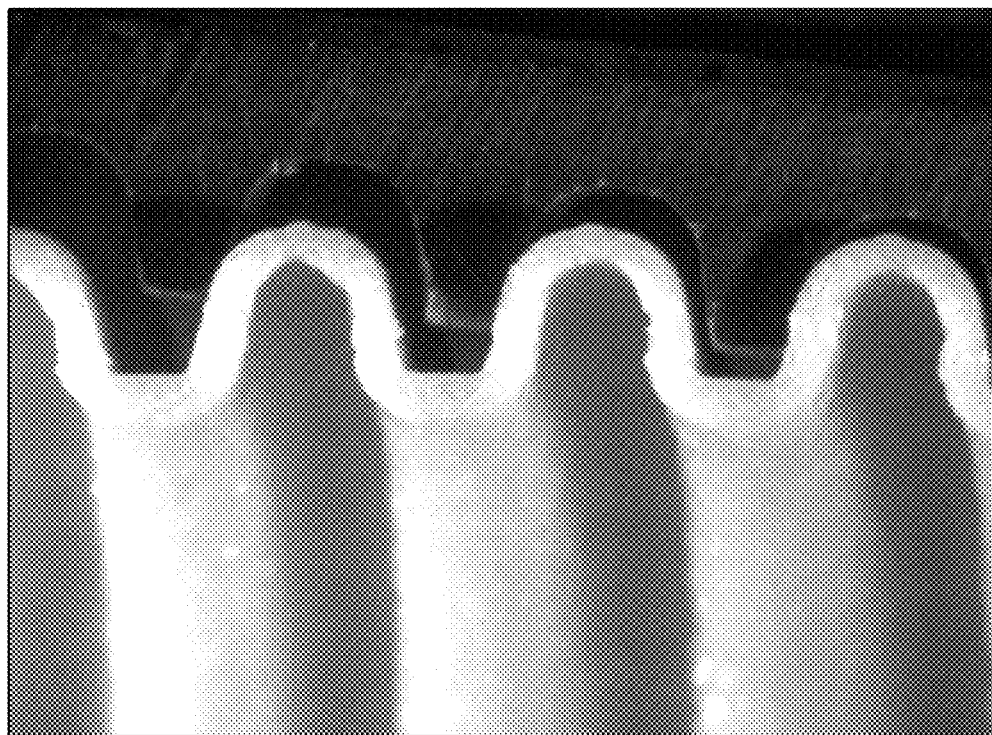
FIGS. 4A through 4D are micrographs of an example foamed, corrugated tube.
Figure 4B:
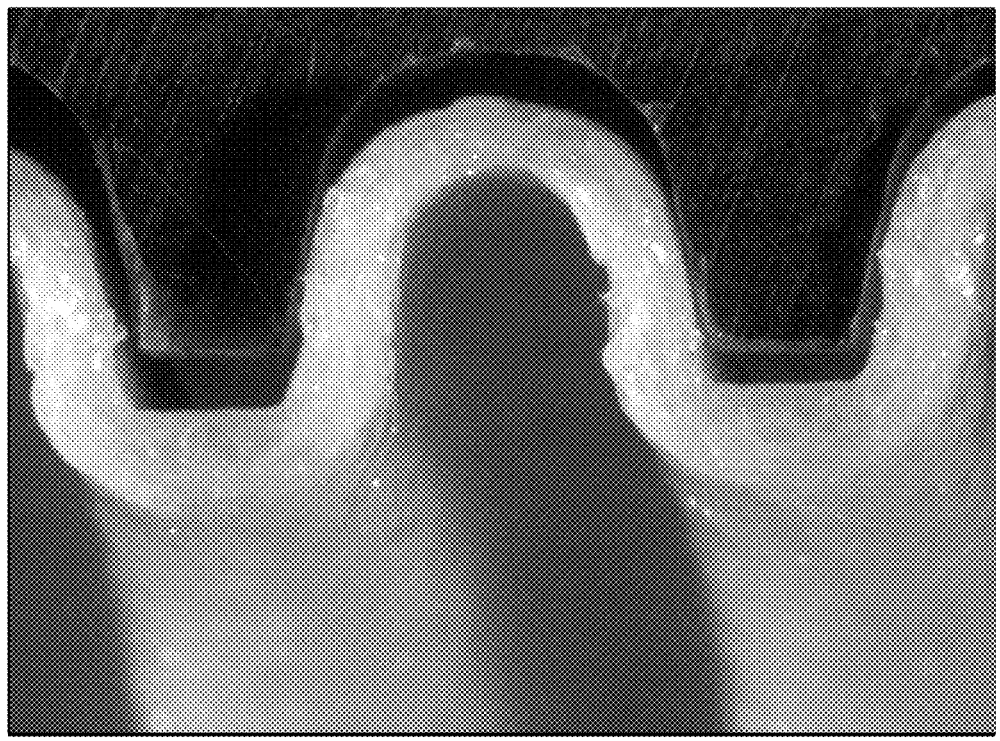
Figure 4C:
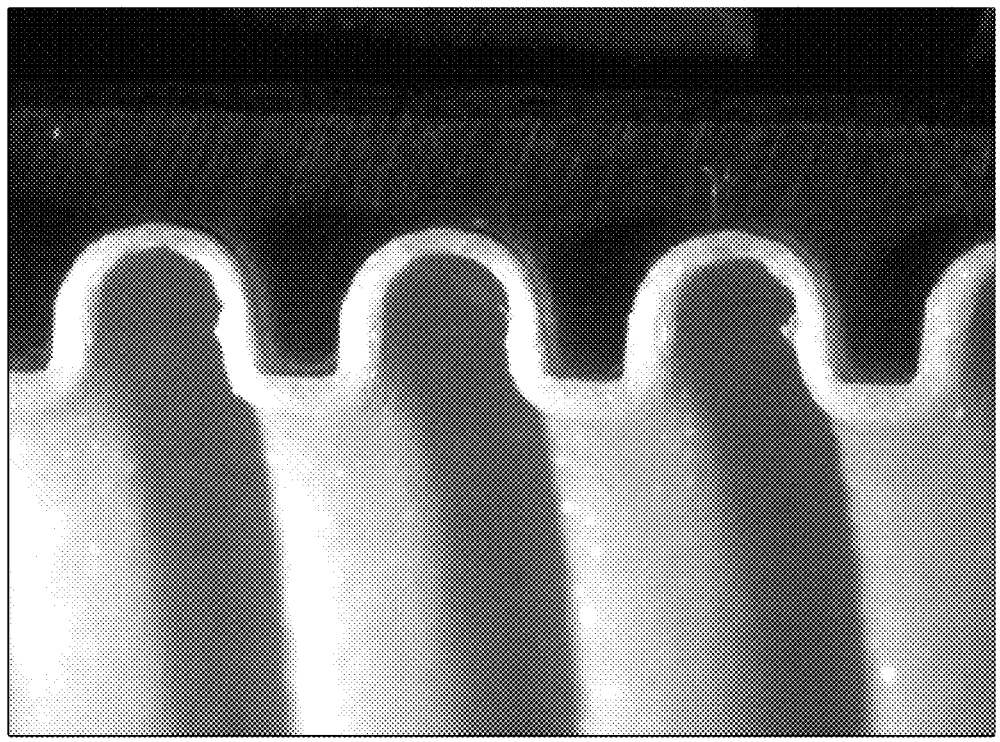
Figure 4D:
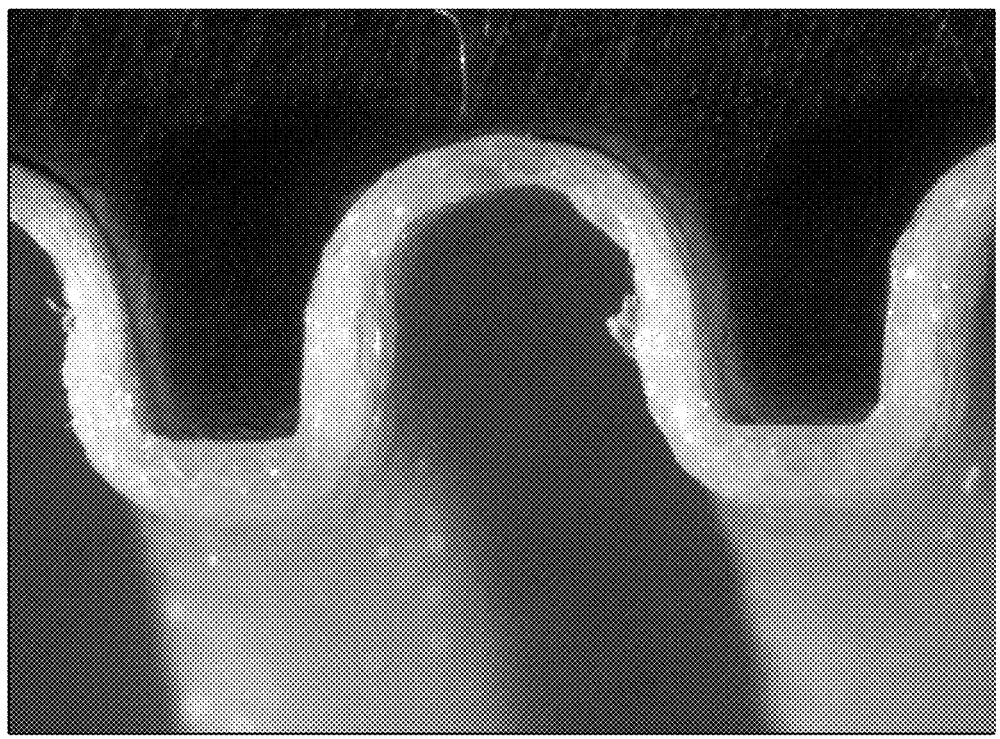
Figure 4E:
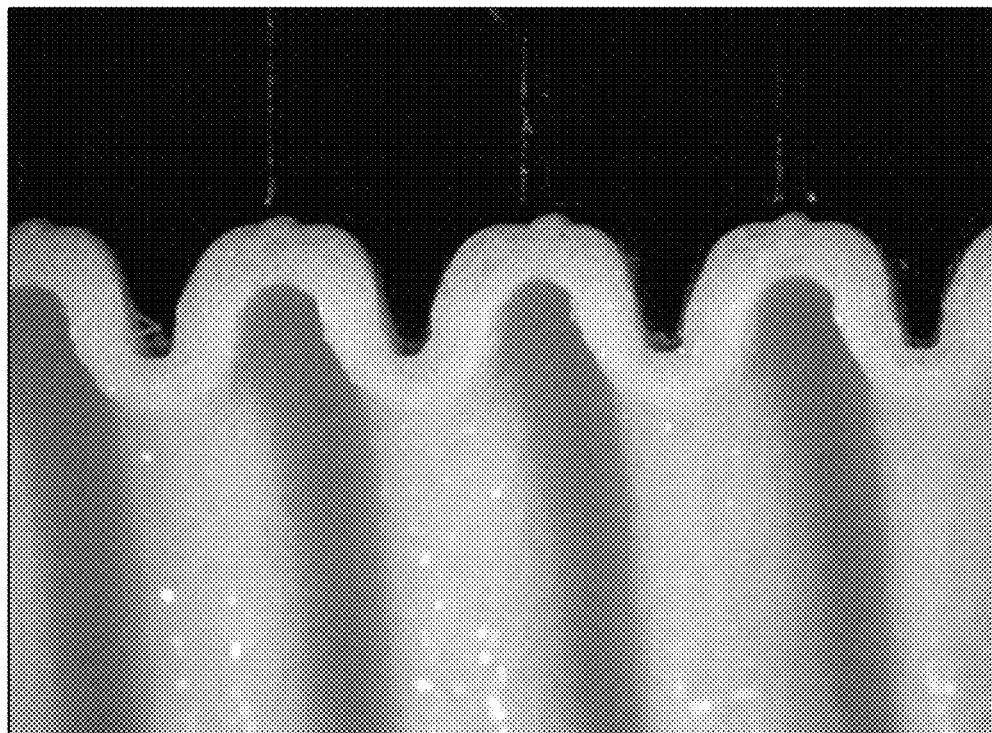
FIGS. 4E and 4F are micrographs of another example foamed, corrugated tube.
Figure 4F:

Point #2 represents data for a sample named "MB27 4%." MB27 4% is a foamed, corrugated ARNITEL® VT 3108 infant tube with an outer diameter of 15.46 cm. The tube was extruded from a mixture of a base polymer (ARNITEL® VT 3108) and 4% (or about 4%) by weight of a foaming agent masterbatch (comprising polyethylene and 20% by weight of Clariant HYDROCEROL® BIH-10E). Experimental data collected on this sample include photomicrographs (shown in FIGS. 4E and 4F and summarized in TABLE 2), void fraction and average sample thickness (shown in TABLE 3), modulus (shown in TABLE 4), and the variation of diffusivity with RH (summarized in TABLE 1).

Figure 4G:
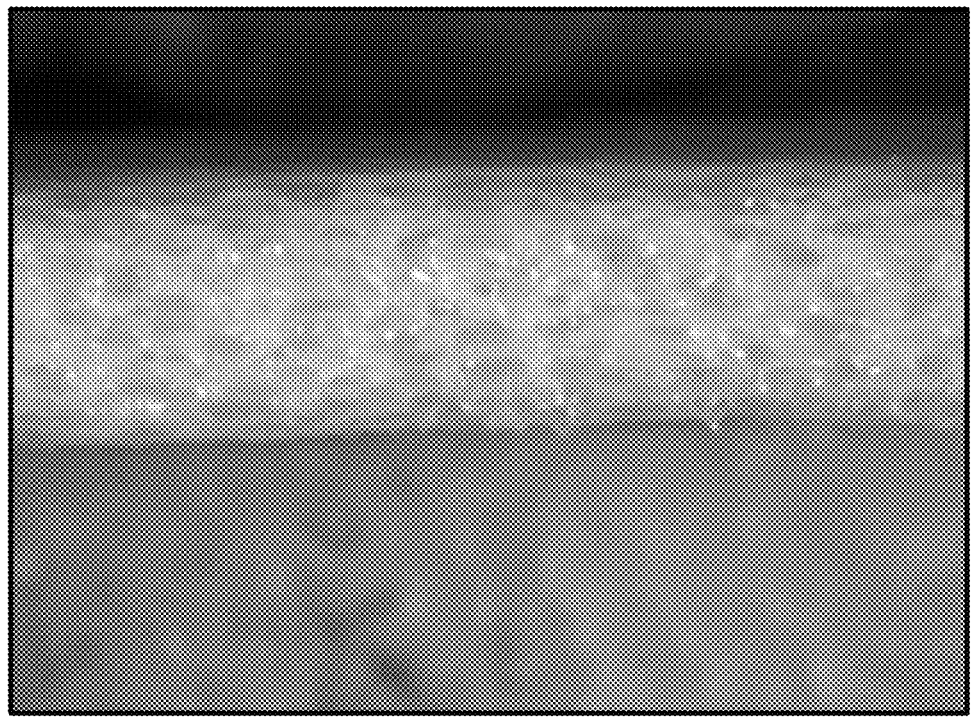
FIGS. 4G and 4H are micrographs of an example foamed, extruded strip.
Figure 4H:
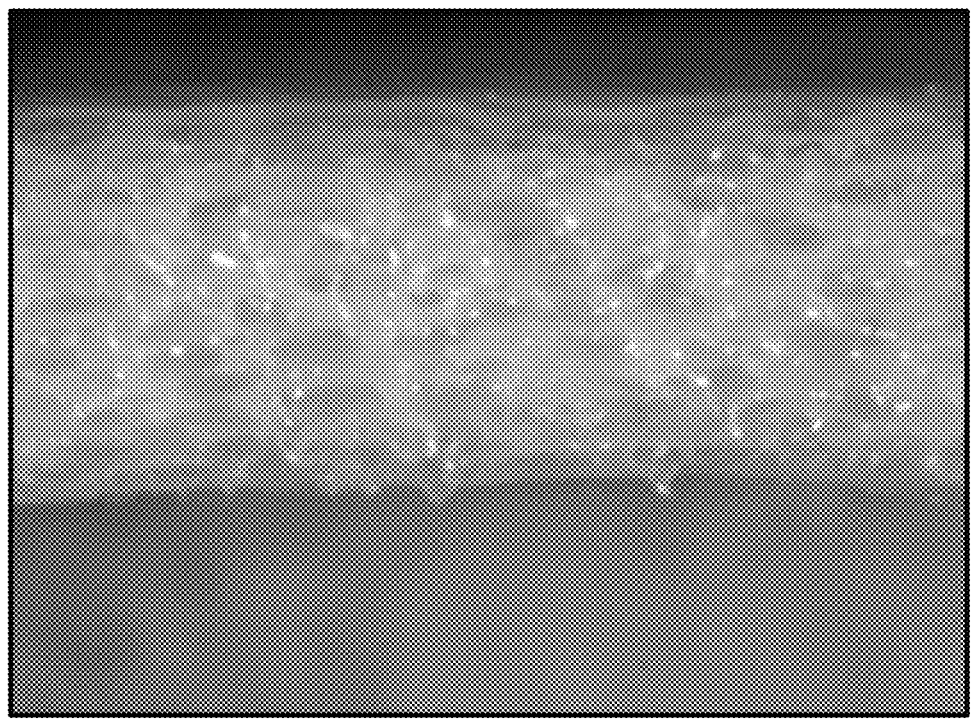

Point #3 represents data for sample named "FIIA-2." FBA-2 is a foamed extruded strip of ARNITEL® VT 3108. Experimental data collected on this sample include photomicrographs (shown in FIGS. 4G and 4H and summarized in TABLE 2), void fraction and average sample thickness (shown in TABLE 3), modulus (shown in TABLE 4), and the variation of diffusivity with RH (summarized in TABLE 1). The variation of dimensions with water content was also measured. It was determined that the variation of length with water content can be described by the following equation:

$$\Delta \frac{X}{X_0} = 0.3683(W\ \%) - 0.1626(W\ \%)^2$$

where
W % is the grams of water absorbed per gram dry polymer
X is the measured dimension, and
$X_0$ is the measured dimension at W %=0.

Figure 4I:
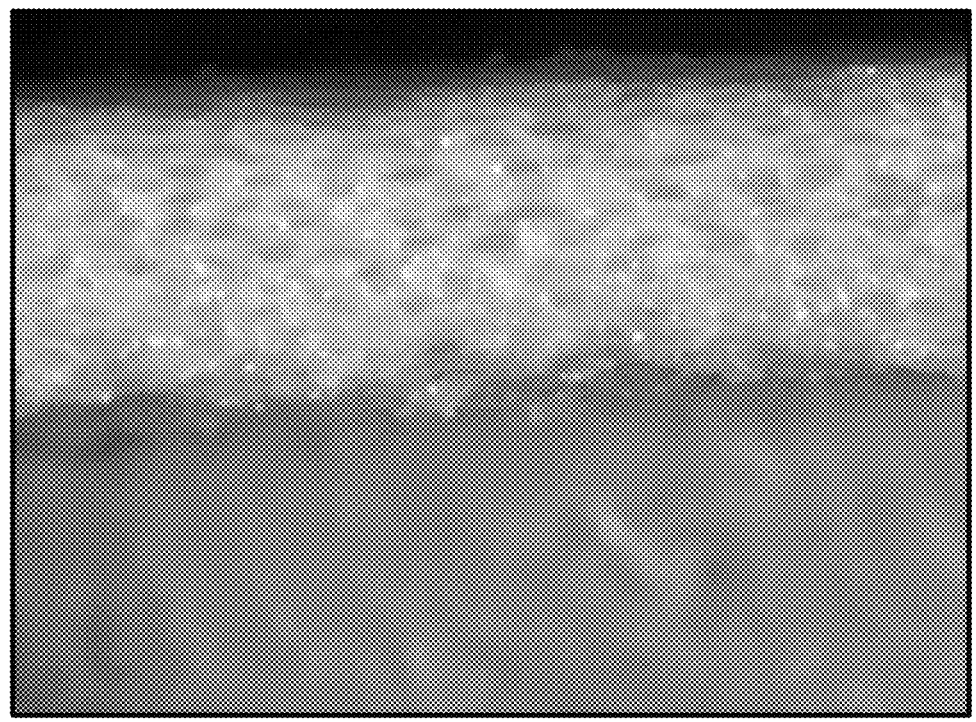
FIGS. 4I and 4J are micrographs of another example foamed, extruded strip.
Figure 4J:
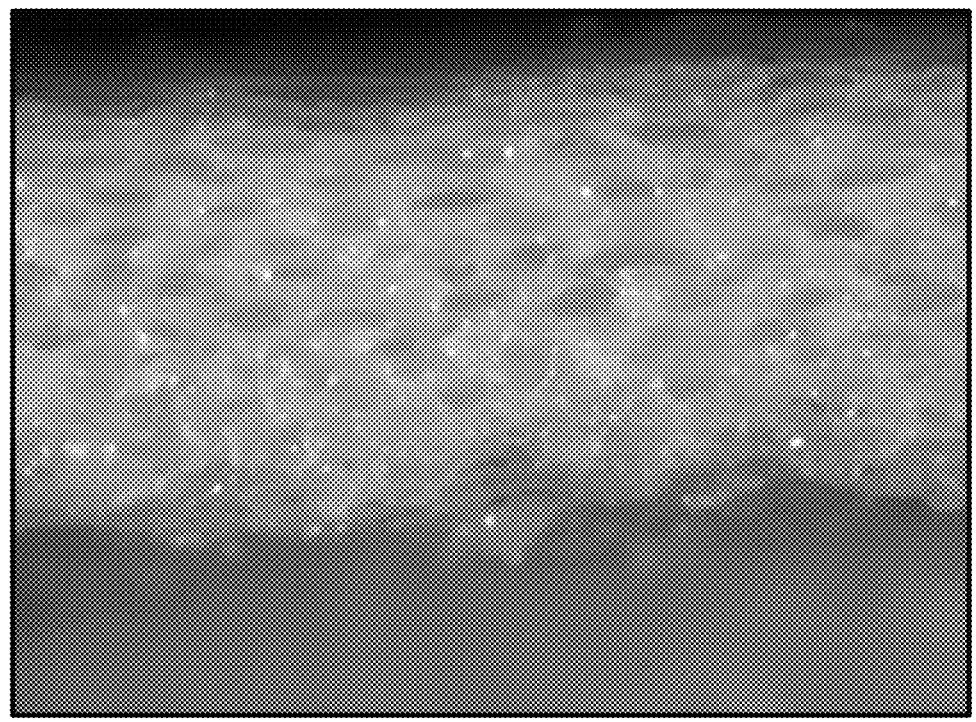

Point #4 represents data for a sample named "FIIA-5." FIIA-5 is a foamed extruded strip of ARNITEL® VT 3108. Experimental data collected on this sample include photomicrographs (shown in FIGS. 4I and 4J and summarized in TABLE 2), void fraction and average sample thickness (shown in TABLE 3), modulus (shown in TABLE 4), and the variation of diffusivity with RH (summarized in TABLE 1). The variation of dimensions with water content was also measured. It was determined that the variation of length with water content ($\Delta X/X_0$) can be described by the following equation:

$$\Delta \frac{X}{X_0} = 0.3674(W\ \%) - 0.3012(W\ \%)^2$$

Figure 4K:
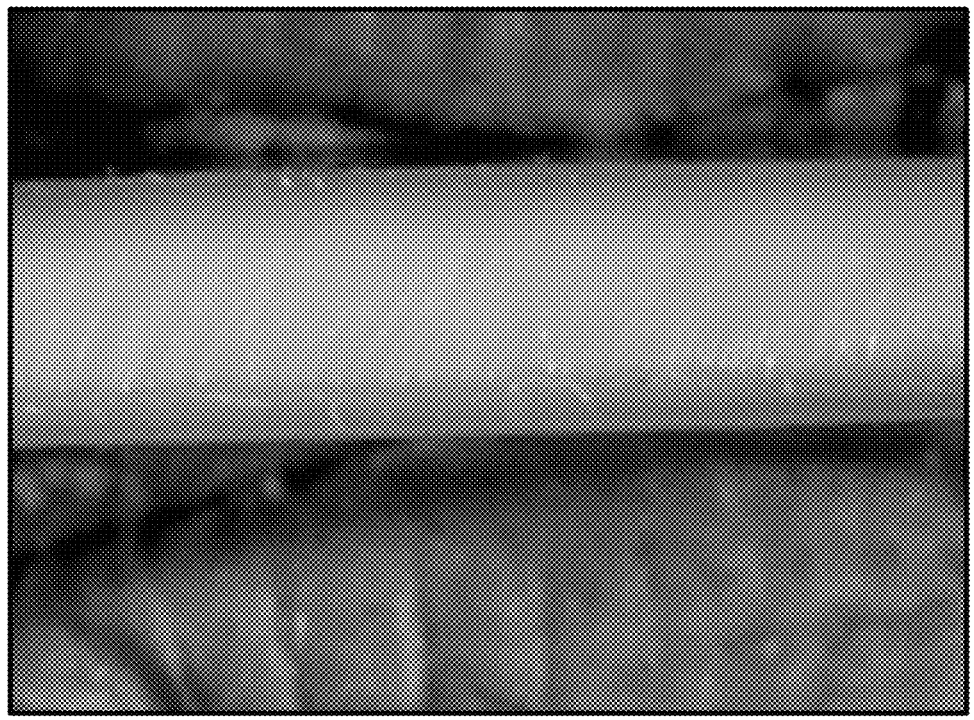
FIG. 4K is a micrograph of a non-foamed, extruded strip formed from a polymer blend.

Point #5 represents data for a sample named "80/20 ARNITEL/PBT." 80/20 ARNITEL/PBT is an extruded strip of polymer made from a 80/20 weight percent blend of ARNITEL® VT 3108 and polybutylene terephthalate (PBT). Experimental data collected on this sample include photomicrographs (shown in FIG. 4K and summarized in TABLE 2), average sample thickness (shown in TABLE 3), modulus (shown in TABLE 4), and the diffusivity RH=100 (summarized in TABLE 1).

Figure 4L:
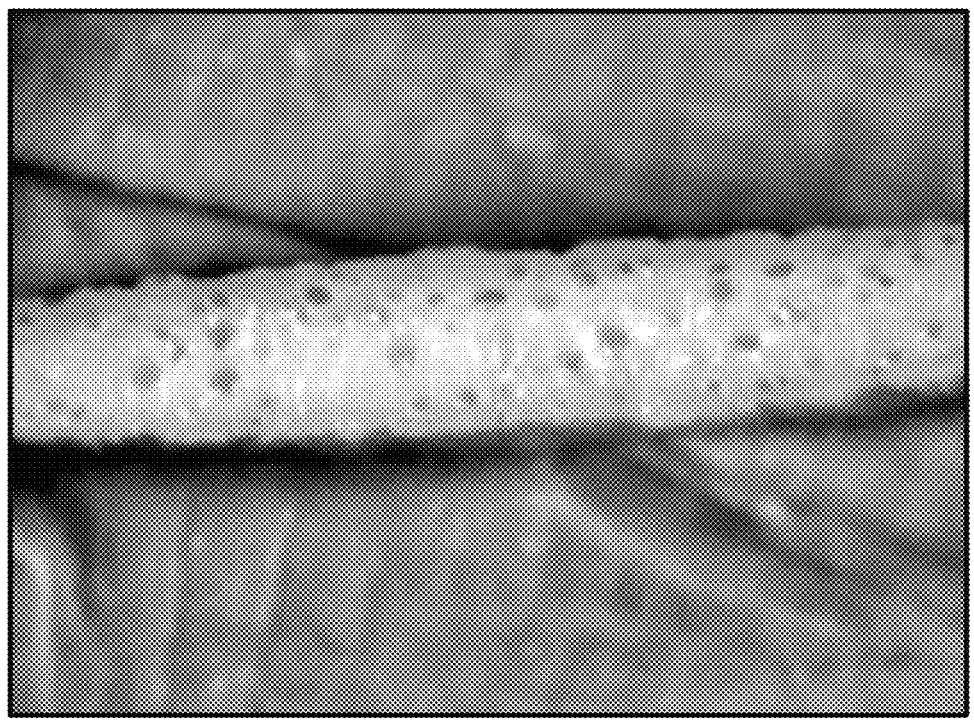
FIGS. 4L and 4M are micrographs of a foamed, extruded strip formed from the polymer blend.
Figure 4M:
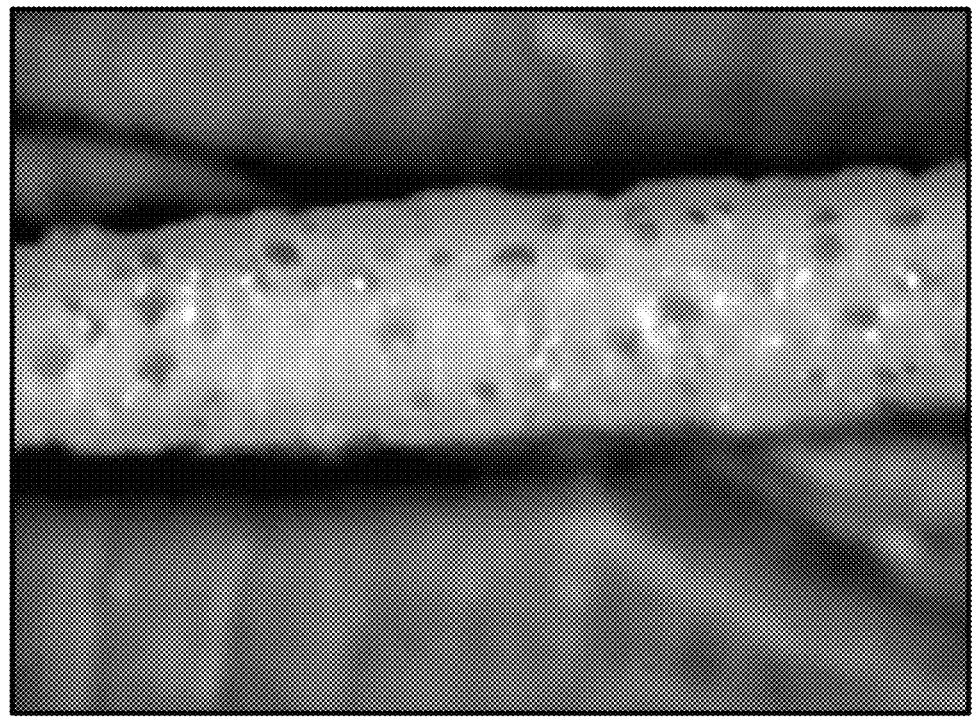

Point #6 represents data for a sample named "80/20 ARNITEL/PBT foamed." 80/20 ARNITEL/PBT foamed is a foamed extruded strip of polymer made from a 80/20 weight percent blend of ARNITEL® VT 3108 and PBT. Experimental data collected on this sample include photomicrographs (shown in FIGS. 4L and 4M and summarized in TABLE 2), void fraction and average sample thickness (shown in TABLE 3), modulus (shown in TABLE 4), and the diffusivity at RH=100 (summarized in TABLE 1).

Figure 4N:
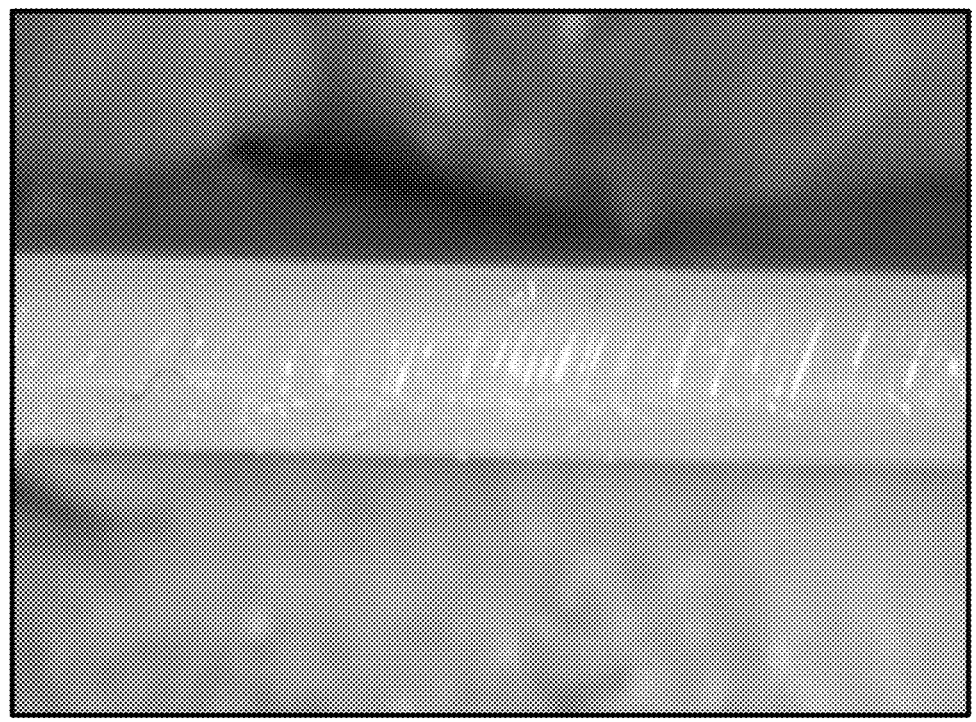
Figure 40:
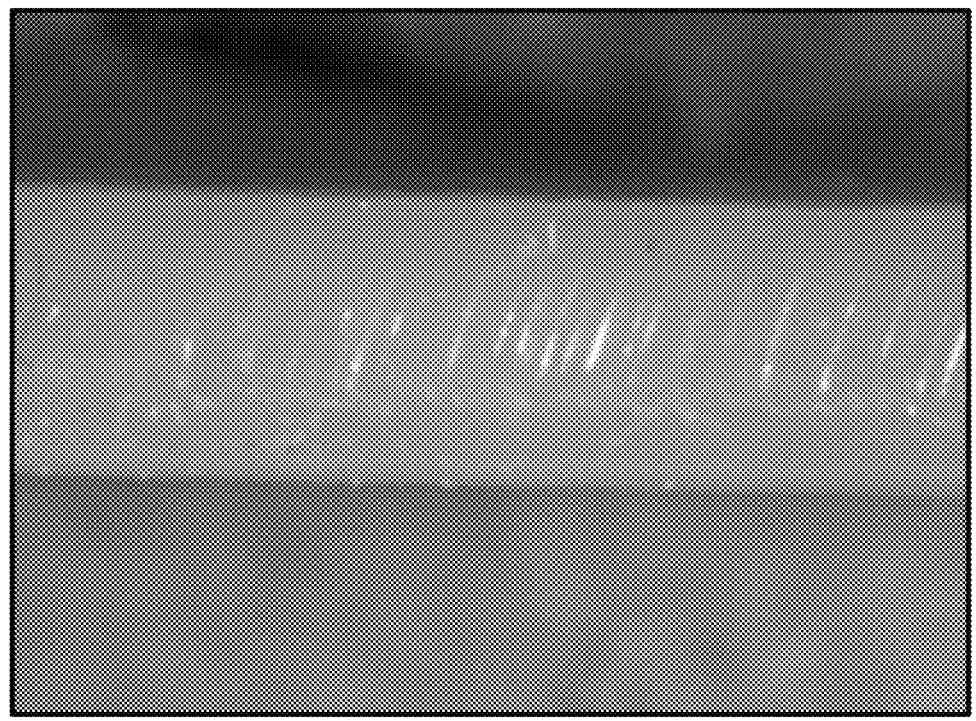

Point #7 represents data for a sample named "FIIA-1." FIIA-1 is an extruded strip of solid Arnitel 3108. Experimental data collected on this sample include photomicrographs (shown in FIGS. 4N and 4O and summarized in TABLE 2), average sample thickness (shown in TABLE 3), modulus (shown in TABLE 4), and the variation of diffusivity with RH (summarized in TABLE 1). The variation of dimensions with water content was also measured. Variation of all three dimensions (length, width and thickness) with water content were observed to be nearly identical (i.e., isotropic expansion) and could be described the following equation.

$$\Delta \frac{X}{X_0} = 0.4123(W\ \%) - 0.1410(W\ \%)^2$$

This relationship was used to calculate the variation of sample thickness in time in water desorption experiments.

Finally, point #8 represents data for a sample named "TPU/Acetal fmd 10%." TPU-acetal fmd 10% is an extruded strip of a foamed blend of ESTANE® 58245 (a TPU) and acetal. Experimental data collected on this sample included void fraction and average sample thickness (shown in TABLE 3), modulus (shown in TABLE 4), and diffusivity (shown in TABLE 4).

Also shown in FIG. 2B is a point labelled "FmdAd1." FmdAd1 is a foamed, corrugated ARNITEL® VT 3108 adult tube with an outside diameter of 24.5 cm. Experimental data collected on this sample included void fraction and average sample thickness (shown in TABLE 3), modulus (shown in TABLE 4), and the variation of diffusivity with RH (summarized in TABLE 1).

Additional unfoamed and foamed polymer materials that are not plotted in FIG. 2A or 2B are described below.

"Batch 15 wts," "Batch 15 f," "MB27 0%," "MB27 6%," "MB22.1," "MB32.1," and "MB41.4" are foamed, corrugated ARNITEL® VT 3108 infant tubes with an outer diameter of 15.46 cm. Experimental data collected on these sample included void fraction and average sample thickness (shown in TABLE 3) and the variation of diffusivity with RH (summarized in TABLE 1). For MB32.1, the variation of length with water content was also measured. The variation was found to be described by the equation:

$$\Delta \frac{X}{X_0} = 0.4614(W\ \%) - 0.1742(W\ \%)^2$$

"TPU, ESTANE 58245" is an unfoamed, corrugated, TPU (ESTANE® 58245) tube having a wall thickness of 0.048 cm. Experimental data collected on this same included void fraction and average sample thickness (shown in TABLE 3), modulus (shown in TABLE 4), and diffusivity (shown in TABLE 4).

TABLE 2

SUMMARY OF MICROGRAPHS

| Point # | Sample Name | Magnifications | Comment |
| --- | --- | --- | --- |
| 1 | AB 14.2a | 10x (FIGS. 4A, C) 20x (FIGS. 4B, D) | Many cells flattened, several connected |
| 2 | MB27 4% | 10x (FIG. 4E) 20x (FIG. 4F) | All cells very flattened, many connected |
| 3 | FIIA-2 | 20x (FIG. 4G) 30x (FIG. 4H) | Very flattened cells, many connected |
| 4 | FIIA-5 | 20x (FIG. 4I) 30x (FIG. 4J) | Very flattened cells, many connected |
| 5 | 80/20 ARNITEL/PBT | 20x (FIG. 4K) | No cells observed |
| 6 | 80/20 ARNITEL/PBT foamed | 15x (FIG. 4L) 20x (FIG. 4M) | Cells are spherical and isolated from each other |
| 7 | FIIA-1 | 20x (FIG. 4N) 30x (FIG. 4O) | No cells observed |

The micrographs show that the foamed polymer samples (samples #1 through #4 and #6) comprise cells or voids within solid polymer. Desirably the size of these voids in the transverse direction are less than 30% (or about 30%) of the thickness of the foamed polymer, for example, less than 10% (or about 10%) of the total thickness.

The micrographs also show that for certain foamed polymer samples falling above lines 201 and 207 (P>60 g-mm/m²/day) in FIG. 2B (namely, samples #1 through #4), the voids are substantially flattened, not spherical. The flattened shape of the voids in turn causes the polymer between the voids to be flattened as well. The flattened shape of the polymer was found to improve the mechanical properties components comprising the foamed polymer. It is believed that having longer lengths of continuous polymer in the longitudinal direction increases the modulus in this direction. Therefore, at least one embodiment includes the realization it can be advantageous for the foamed polymer to have at least some voids, for instance at least 80% or thereabout, that are flattened along the longitudinal axis. The aspect ratio of this flattening (length to height) is desirably at least 2:1 (or about 2:1) or at least 3:1 (or about 3:1), for example, between 2:1 and 7:1 (or about 2:1 and 7:1) or between 3:1 and 7:1 (or about 3:1 and 7:1).

It was also observed that for these samples, the voids are not isolated from each other. Many of the voids are connected or joined together. That is, the foamed polymer has "open cells." The open cellular structure of these foamed polymer improves breathability, because it allows water vapor to travel a greater distance both axially (or transversely) and longitudinally, without having to pass through solid polymer. Desirably, at least 10% (or about 10%) of the voids in a foamed polymer are interconnected. In some embodiments, at least 20% (or about 20%) of the voids are connected to other voids.

TABLE 3

SUMMARY OF VOID FRACTION AND AVERAGE THICKNESS

| Point # | Sample Name | Void Fraction, % | Average thickness, cm |
|---|---|---|---|
|  | FmdAd1 | 16.8 | 0.507 |
| 1 | AB 14.2a | 33.7 | 0.0487 |
| 2 | MB27 4% | 41.0 | 0.0628 |
| 3 | FIIA-2 | 46.6 | 0.173 |
| 4 | FIIA-5 | 53.0 | 0.198 |
| 5 | 80/20 ARNITEL/PBT | 0.0 | 0.1807 |
| 6 | 80/20 ARNITEL/PBT foamed | 20.0 | 0.1647 |
| 7 | FIIA-1 | 0.0 | 0.124 |
| 8 | TPU/Acetal foamed 10% | 15.0-20.0 | 0.139 |
|  | TPU, ESTANE 58245 | 0.0 | 0.048 |
|  | Batch 15 wts | 56.0 | 0.0799 |
|  | Batch 15 f | 56.0 | 0.0799 |
|  | MB27 0% | 0.0 | 0.0256 |
|  | MB27 6% | 52.0 | 0.0941 |
|  | MB22.1 | 24.1 | 0.0575 |
|  | MB32.1 | 33.2 | 0.0448 |
|  | MB41.4 | 46.2 | 0.0829 |

TABLE 4

SUMMARY OF MODULUS, DIFFUSIVITY, AND PERMEABILITY

| Point # | Sample Name | Modulus, MPa | Diffusivity at RH = 97, $cm^2$/sec | Permeability, g-mm/$m^2$/day |
|---|---|---|---|---|
|  | ARNITEL ® VT 3108 | 122 | $2.11 \times 10^{-7}$ | 36 |
|  | FmdAd1 | 96.8 | $2.30 \times 10^{-7}$ | 39 |
| 1 | AB 14.2 | 61.5 | $4.77 \times 10^{-7}$ | 81.4 |
| 2 | MB 27 4% | 45 | $5.65 \times 10^{-7}$ | 96.5 |
| 3 | FIIA-2 | 47.7 | $8.66 \times 10^{-7}$ | 147.6 |
| 4 | FIIA-5 | 41.7 | $13.7 \times 10^{-7}$ | 234 |
| 5 | 80/20 ARNITEL/PBT | 375 | $1.46 \times 10^{-7}$ | 24.8 |
| 6 | 80/20 ARNITEL/PBT foamed | 266 | $1.9 \times 10^{-7}$ | 32.5 |
| 7 | FIIA-1 | 122 | $2.11 \times 10^{-7}$ | 36 |
| 8 | TPU/Acetal foamed | 37 | $6.59 \times 10^{-6}$ | 151 |
|  | 10% TPU, ESTANE 58245 | 18 | $2.41 \times 10^{-7}$ | 80 |

In TABLE 4, the permeability data for ARNITEL®-based samples were calculated using the relation:

$$P_{sample} = P_{ARNITEL\ VT3108} \frac{D_{sample}}{D_{ARNITEL\ VT3108}}$$

where $P_{sample}$ represents the permeability of the sample, $P_{ARNITEL\ VT\ 3108}$ represents the permeability of ARNITEL® VT 3108, $D_{sample}$ represents the diffusivity of the sample, and $D_{ARNITEL\ VT\ 3108}$ represents the diffusivity of ARNITEL® VT 3108. Similarly, the permeability data for TPU (ESTANE®)-based samples were calculated using the relation:

$$P_{sample} = P_{ESTANE\ 58245} \frac{0.7 D_{sample}}{D_{ESTANE\ 58245}}$$

$P_{ESTANE\ 58245}$ and $D_{ESTANE\ 58248}$ represent the permeability and diffusivity of ESTANE® 58245, respectively. The factor 0.7 reflects the lower water content of the blended sample.

Another suitable foamed polymer material is polyether-based thermoplastic polyurethane (TPU), which has good breathability and tear resistance. However, TPU has poor stiffness (a low Young's modulus). Much research has gone into improving the stiffness of the material by mixing it with other polymers. However, it has been found while blending TPU with other polymers can be effective in increasing stiffness, there can be a serious decrease in the breathability of the blended polymer.

After testing, blends have been identified which greatly improve mechanical stiffness without reducing the breathability to an unacceptable level. An example blend is the blend of copolyester TPE/PBT discussed above. Another example blend comprises TPU and polycarbonate-acrylonitrile butadiene styrene (PC-ABS, sold as WONDERLOY® for example). A suitable weight ratio of TPU:WONDERLOY® is 70:30 (or about 70:30). Tests conducted using a 19 mm diameter single screw extruder have shown that tensile strength of the blend exhibits a marked improvement in stiffness over TPU alone (14 fold or thereabout), while the moisture vapour transmission rate shows only a slight reduction in breathability (30% or thereabout). By foaming the TPU-WONDERLOY® polymer blend, a further improvement in the breathability versus stiffness can be achieved as described above.

As discussed above, yet another example blend according to at least one embodiment comprises a TPU (ESTANE® 58245) and acetal, a compound having very low breathability (permeability) and water uptake. A foamed strip (void fraction between 15 and 20% or about 15 and 20%) was created from ESTANE® 58245 and acetal in a weight ratio of 70:30 (or about 70:30). The average sample thickness was 0.139 cm. The water uptake of the blend at 100% RH was 0.38 g water per gram dry polymer (38%). The diffusivity of the sample was measured from the desorption curve and found to be $6.59 \times 10^{-6}$ $cm^2$/sec at 23° C. The modulus of the sample was 34 MPa, and the permeability was calculated to be 151 g-mm/$m^2$/day.

These results compare to a control example which comprises unfoamed TPU (ESTANE® 58245). A corrugated tube was extruded having a wall thickness of 0.048 cm and a water uptake at 100% RH of 0.53 g water per gram of dry polymer (53%). The diffusivity of the non-foamed sample was measured from the desorption curve and found to be $2.41 \times 10^{-7}$ $cm^2$/s at 23° C. The modulus was 18 MPa. The permeability of this polymer is 80 g-mm/$m^2$/day.

Components Comprising Foamed Polymers

It will be appreciated that the foamed breathable materials described above lend themselves to many medical components where a highly breathable but self supporting, semi-rigid material is advantageous. Accordingly, all of the particulars of the breathable foamed material discussed above are applicable to these components. The following are just some examples of components to which the foamed breathable material provides new advantages that have previously not been possible. Manipulation of the void fraction, thickness, and void size allows a wide range of customisation of the bulk properties of formed components.

In general, a component comprises a wall defining a space within and wherein at least a part of said wall is of a breathable foamed material as described above, which allows the transmission of water vapor from gases within the space, but prevents the transmission of liquid water. Preferably, the wall is also impermeable to the bulk flow of gases within the space, including breathing gases, anaesthetic gases, insufflation gases, and/or smoke.

Because of its breathability, the wall forms a water vapor pathway from the gases space to the region on the other side of the wall. In some embodiments, there is a water vapor pathway from the gases space to ambient air through said breathable foamed material. The pathway through can be a direct pathway, and the wall is exposed directly to ambient air. Alternatively, the pathway is indirect, and the pathway passes through one or more other walls between the gases space and ambient air. In other configurations, there can be a second gases space (called a sweep gases space) on the other side of said wall, instead of ambient air. This sweep gases space can, in turn, vent indirectly to ambient air. In that case, the water vapor pathway runs from the gases space to the sweep gases space.

In any of the above embodiments, the entire enclosing wall can be formed of the foamed material. In at least one embodiment, at least a region of the wall has a thickness between 0.1 and 3.0 mm (or about 0.1 and 3.0 mm), such as between 0.1 and 1.5 mm (or about 0.1 and 1.5 mm). For example, at least a region of the wall can have a thickness between 0.7 and 1.0 mm (or about 0.7 and 1.0 mm) or between 0.7 and 3.0 mm (or about 0.7 and 3.0 mm).

In any of the above embodiments, the wall can include at least two zones. The first zone is an outer skin comprising a layer of substantially closed-cell foamed material, and the second zone is an inner layer adjacent the outer layer and between the outer layer and the gases space. The skin thickness can be between 5 and 10% (or about 5 and 10%) of the wall thickness, for example, between 10 and 50 µm (or about 10 and 50 µm). Each of the first zone and the second zone have voids. In certain embodiments, no more than 5% (or about 5%) of the voids in the first zone exceed a diameter of 100 µm. The voids in the second zone are larger than the voids in the first zone. For example, in some embodiments no more than 5% (or about 5%) of the voids of said second zone of foamed material exceed a diameter of 700 µm.

In any of the above embodiments, the wall can also include at least one reinforcing rib stiffening the wall or at least one region where the wall is locally thickened to stiffen the wall.

The component can be a patient interface; or a tube, such as a breathing tube for use in a breathing circuit; or a tube and at least part of a patient interface; or a conduit (that is, a portion of a tube that need not be closed around its circumference) for use in a breathing circuit; or a mask (including a mask frame and a seal extending around the perimeter of the mask frame, wherein the mask frame comprises the wall and a substantial majority of the wall is formed of the breathable foamed material); or a component of an insufflation system, such as a tube or conduit for use in at least part of the exhaust arm of an insufflation system.

Figure 5:
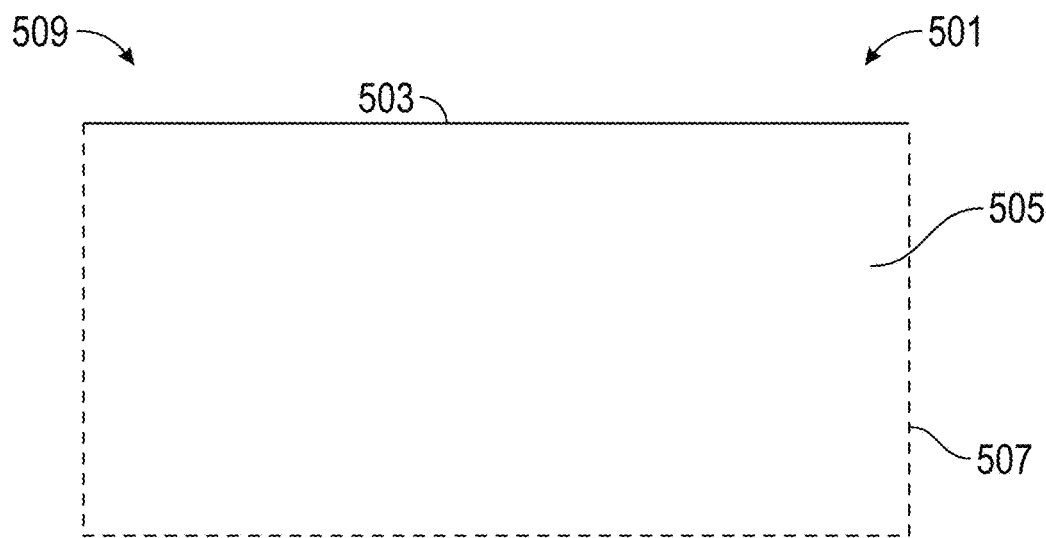
FIG. 5 is a schematic illustration of a component for a medical circuit incorporating a breathable foamed polymer material.

Reference is next made to FIG. 5, which shows a component 501 according to at least one embodiment. The component 501 is formed having a wall 503, defining a gases space 505 on one side. The wall 503 comprises a breathable foamed polymer as described above. As represented by dotted line 507, the wall may or may not define a completely closed gases space 505. When in use, the gases space can be substantially closed so that the wall 503 defines gases space 505 on one side of the wall 503 and the space 505 contains a humid gas.

On the other side of wall 503 is a second gases space 509. In at least one embodiment, the second gases space 509 is ambient air. The wall 503 of component 501 is of a breathable foamed material that allows the transmission of water vapor but substantially prevents the transmission of liquid water and the bulk flow of breathing gases. In order for the breathable foamed material to permit drying of the gases in space 505, the outer surface of the wall 503 is exposed to ambient air or a dry sweep gas in a second gases space 509. In such a configuration, gases having a high relative humidity within gases space 505 can be dried by transmission of water vapor through wall 503 into the second gases space 509, which may be for example ambient air. The drying of the gases within gases space 505 is useful to produce and/or prevent rain-out occurring in the gases space 505 when filled with a relatively warm or humid gas/air/breathing gas.

In one example, the component 501 may be a patient interface, such as a respiratory mask, and gases space 505 may be at least partially defined by wall 503, and by a patient's face (not shown) to substantially enclose the space 505. In this example, the patient's face is represented by dotted line 507. In another embodiment, the component 501 may be a breathing tube (inspiratory or expiratory). Patient interfaces and breathing tubes are discussed in greater detail below.

Breathable Tubes

In assisted breathing, particularly in medical applications, gases having high levels of relative humidity are supplied and returned through flexible breathing tubes of a relatively restricted size, typically between a range of 10 to 25 mm (or about 10 to 25 mm) diameter (covering both neonatal and adult applications). Such breathing tubes are ideally very light, resistant to kinking or pinching, and flexible to ensure the greatest performance and level of comfort for the patient. The light weight of a breathing tube is very important to reduce any forces applied to the patient interface by the weight of the tube. Similarly, breathing tubes must be flexible and able to bend easily to achieve a high level of patient comfort which in turn can improve patient compliance. However, extremely light and flexible components are usually weak and prone to excessive kinking. It was discovered that a tube comprising the above-described foamed polymer can resist kinking and pinching, yet is light and sufficiently flexible to improve patient comfort.

Because a tube is a type of component, the particulars of the component discussed above are applicable to the tube discussed here. In general, a medical circuit tube comprises an inlet (for receiving humidified gases), an outlet (for expelling humidified gases), and an enclosing wall defining at least one gases passageway between said inlet and said outlet, wherein at least a part of said enclosing wall is of a breathable foamed material allowing the transmission of water vapour but substantially preventing the transmission of liquid water and the bulk flow of breathing gases. In at least one embodiment, the tube is an extruded corrugated tube. The medical circuit tube can be used as a breathing tube or conduit or a tube or conduit for a limb of an insufflation system. For instance, the tube can be an expiratory breathing tube or an exhaust conduit, respectively. The tube can also be part of a patient interface.

The tube can be flexible. That is, the tube can be bent around a 25 mm diameter rod without kinking or collapse. More particularly, the tube is flexible as defined by passing the test for increase in flow resistance with bending according to ISO 5367:2000(E).

In any of the above embodiments, the tube can have a length between 1 and 2 m (or about 1 and 2 m), for instance 1.5 m (or about 1.5 m). A tube can have a mean diameter between 10 and 25 mm (or about 10 and 25 mm). In at least one embodiment, the tube has a wall thickness between 0.1 and 1.2 mm (or about 0.1 and 1.2 mm), for example, between 0.6 mm and 1.0 mm (or about 0.6 and 1.0 mm). Preferably, a tube comprises a breathable enclosing wall over a significant portion of its total length. For instance, in at least one embodiment, at least 80% of the length of the tube comprises a breathable enclosing wall. The breathable wall is preferably located proximal the inlet end of the tube for receiving humidified gas. For example, for a tube 1.5 m (or about 1.5 m) in length, at least 1.2 m (or about 1.2 m) of the tube comprises a breathable wall, starting proximal the inlet end.

Because of its breathability, the wall forms a water vapor pathway from the gases space to the region on the other side of the wall. In some embodiments, there is a water vapor pathway from the gases space to ambient air through said breathable foamed material. The pathway through can be a direct pathway, and the wall is exposed directly to ambient air. For example, in at least one embodiment, the tube is a breathing tube and is terminated by a first connector at said inlet and a second connector at said outlet. Only one gases passageway is provided the length between said inlet connector and said outlet connector.

Alternatively, the pathway is indirect, and the pathway passes through one or more other walls between the gases space and ambient air. In other configurations, there can be a second gases space (called a sweep gases space) on the other side of said wall, instead of ambient air. This sweep gases space can, in turn, vent indirectly to ambient air. In that case, the water vapor pathway runs from the gases space to the sweep gases space. For example, the tube can be a coaxial breathing tube. In a coaxial breathing tube, the gases space is an inspiratory limb or an expiratory limb, and the second gases space is the other of said inspiratory limb or an expiratory limb. One gases passageway is provided between the inlet of said inspiratory limb and the outlet of said inspiratory limb, and one gases passageway is provided between the inlet of said expiratory limb and the outlet of said expiratory limb. In one embodiment, the gases space is said inspiratory limb, and said second gases space is said expiratory limb. Alternatively, the gases space can be the expiratory limb, and the second gases space is the inspiratory limb.

As explained above in conjunction with the description of the component, in any of the above embodiments, the wall can include at least two zones. The first zone is an outer skin comprising a layer of substantially closed-cell foamed material, and the second zone is an inner layer adjacent the outer layer and between the outer layer and the gases space. The skin thickness can be between 5 and 10% (or about 5 and 10%) of the wall thickness, for example, between 10 and 50 µm (or about 10 and 50 µm). Each of the first zone and the second zone have voids. In certain embodiments, no more than 5% (or about 5%) of the voids in the first zone exceed a diameter of 100 µm. The voids in the second zone are larger than the voids in the first zone. For example, in some embodiments no more than 5% (or about 5%) of the voids of said second zone of foamed material exceed a diameter of 700 µm.

Furthermore, in any of the above embodiments, the tube can include a plurality of reinforcing ribs arranged about the enclosing wall. These ribs can be co-extruded with the tube to be generally aligned with the longitudinal axis of the tube. Preferably, there are three to eight reinforcing ribs, and more particularly, three to five reinforcing ribs.

In addition to the above, to reduce or eliminate the formation of condensation within the tube, and to maintain a substantially uniform temperature in the gases flow through the tube in use, a heater, such as a resistance heater wire, may be provided within the tube passageway or within tube wall.

In a particular embodiment, the tube has a length of 1.525 m (or thereabout), a weight of 54 g (or thereabout), a void fraction of 35% (or thereabout), a pneumatic compliance of 0.23 mL/cm $H_2O$/m (or thereabout), and a permeability of 85 g-mm/m$^2$/day (or thereabout). The tube is formed from 95% (or about 95%) ARNITEL® VT 3108 and 5% (or about 5%) of a foaming agent masterbatch comprising polyethylene and 20% (or about 20%) by weight of Clariant HYDROCEROL® BIH-10E.

Figure 6A:
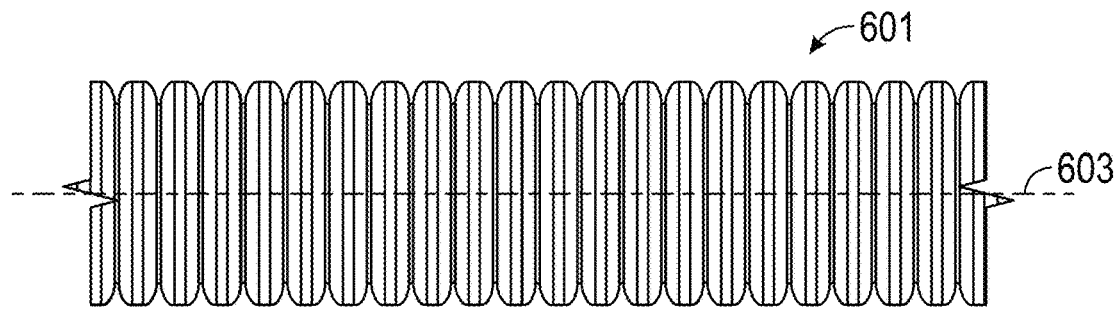
FIG. 6A is a side-plan view of a tubular component incorporating a breathable foamed polymer material.
Figure 6B:
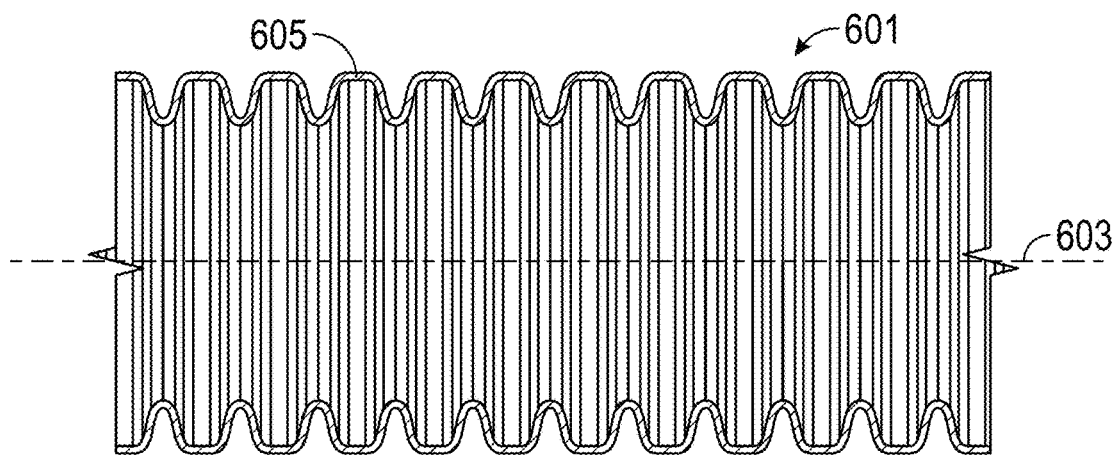
FIG. 6B is cross section view of the tube component of FIG. 6A.

Reference is next made to FIGS. 6A and 6B, which show a breathable tube 601 according to at least one embodiment. FIG. 6A shows a side view of the tube 601, while FIG. 6B shows cross-section of the tube 601 along the same side view as FIG. 2A. In both FIG. 6A and FIG. 6B, the horizontal axis is indicated as line 603-603. The tube wall, shown as wall 605 in FIG. 6B is a breathable foamed material, as described above. Wall 605 can be between 100 and 1500 µm (or about 100 and 1500 µm) thick for a breathing tube of typical dimensions—between 12 and 20 mm (or about 12 and 20 mm) diameter for neonatal and adult applications respectively and 1 to 2 m (or about 1 to 2 m) in length. However, the wall 605 may be up to 3 mm (or about 3 mm) thick and still deliver good breathability.

The tube 601 is corrugated (that is, the tube has a ridged or grooved surface). The method for forming the corrugated tube is discussed in greater detail below, with respect to FIG. 15. However, in some embodiments, the tube has a smooth surface.

Figure 7A:
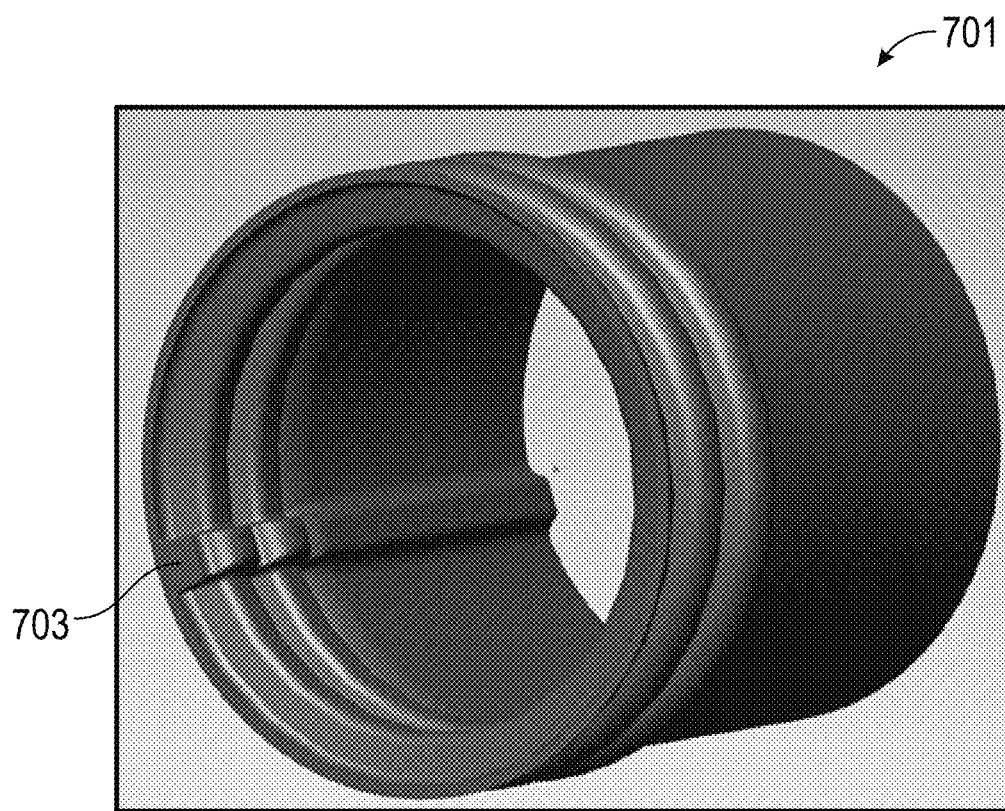
FIG. 7A is a front-perspective view of a tubular component incorporating integral, reinforcing ribs, the component being partially corrugated.
Figure 7B:
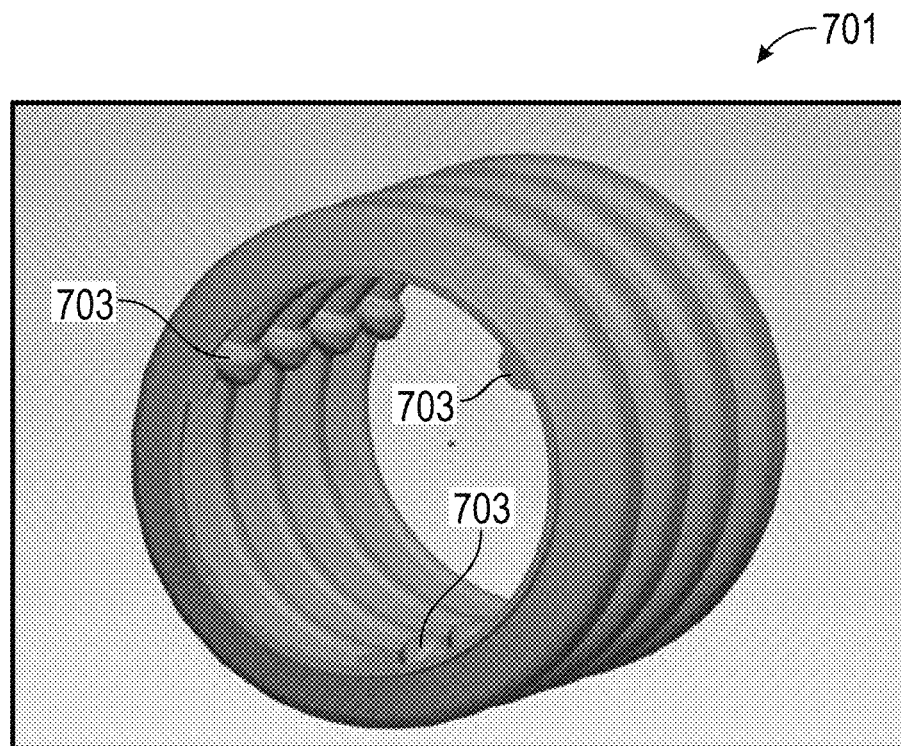
FIG. 7B is a front perspective view of the tubular component being fully corrugated.

Reference is next made to FIGS. 7A and 7B, which show a breathable tube 701 according to at least one embodiment. Again, the tube 701 is manufactured from a foamed breathable material, as described in any one of the examples herein. The tube further includes a plurality of reinforcing ribs 703 that can be co-extruded with the tube. The form of the ribs 703 is determined by the extruder die head, and the size and the foaming level is controlled by the temperature and pressure when it exits the die head.

The ribs 703 can be formed from the same foamed polymer as the tube 701. Alternatively, the ribs 703 can be made from a different material than the tube. This can be achieved by co-extrusion. As shown in FIG. 7A, the tube 701 can be extruded with the ribs 703 in place, and then corrugated to form the "dotted" structure shown in FIG. 7B. In certain embodiments, a tube includes between three and eight reinforcing ribs, such as between three and five reinforcing ribs. Such additionally reinforced tubes can find independent application in one or more of the tube components described in this specification in relation to medical circuits.

Figure 8A:
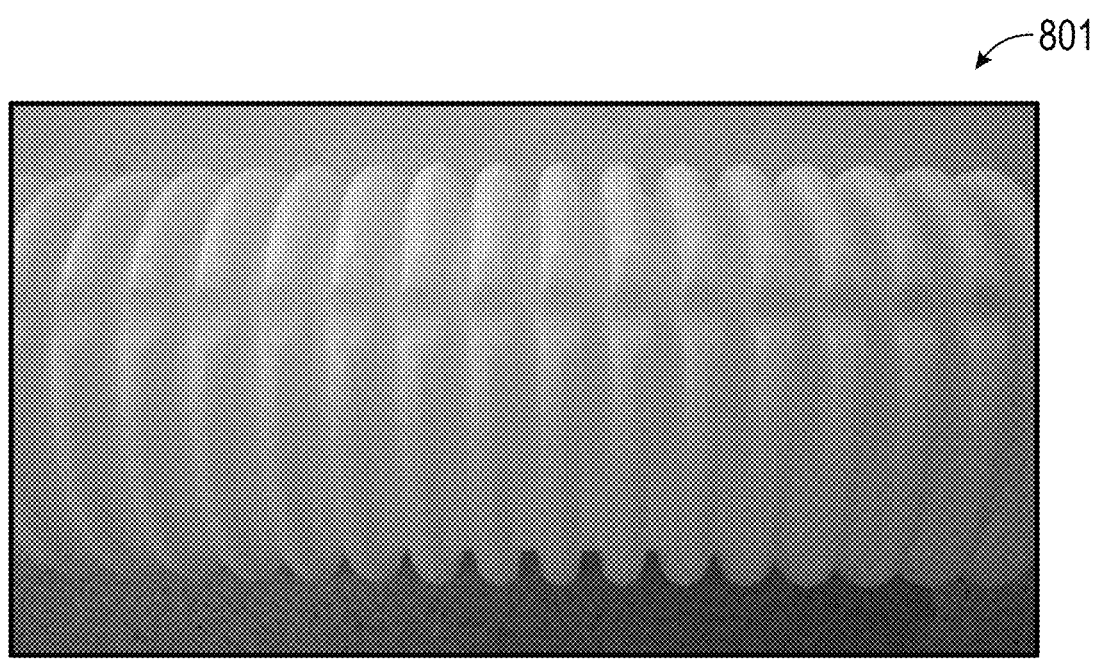
FIG. 8A is a front-perspective photograph of an alternate configuration of a corrugated, tubular component incorporating ribs.
Figure 8B:
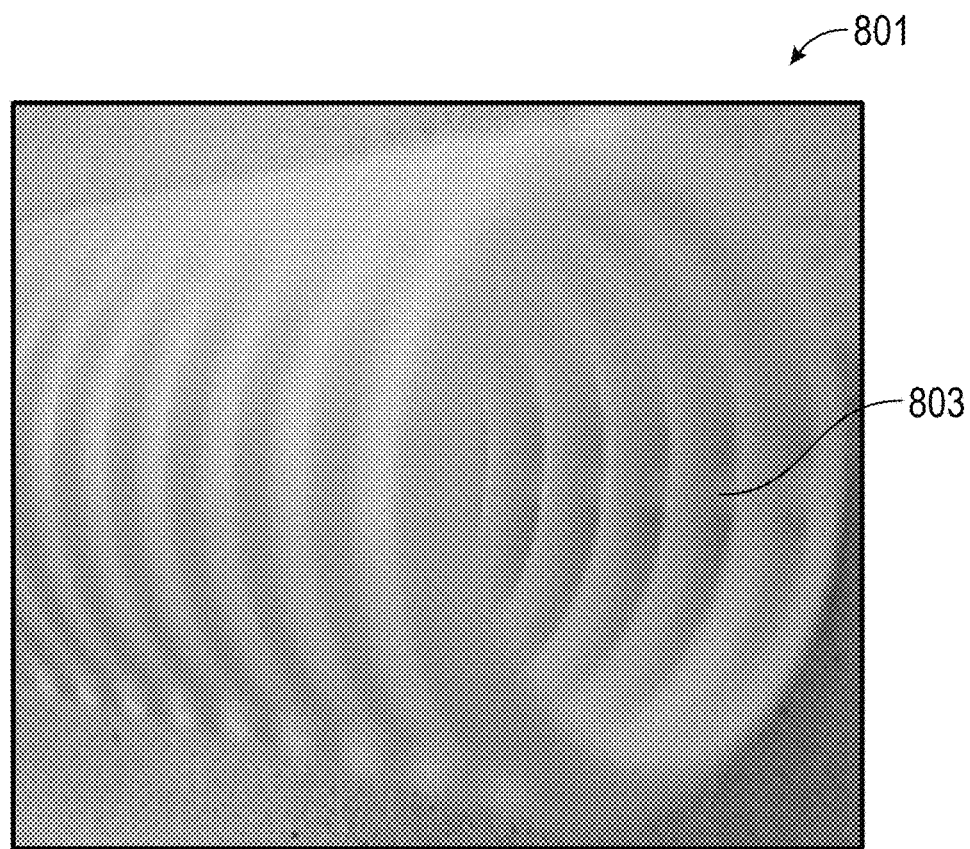
FIG. 8B is a front-perspective photograph of the tubular component of FIG. 8A.
Figure 8C:
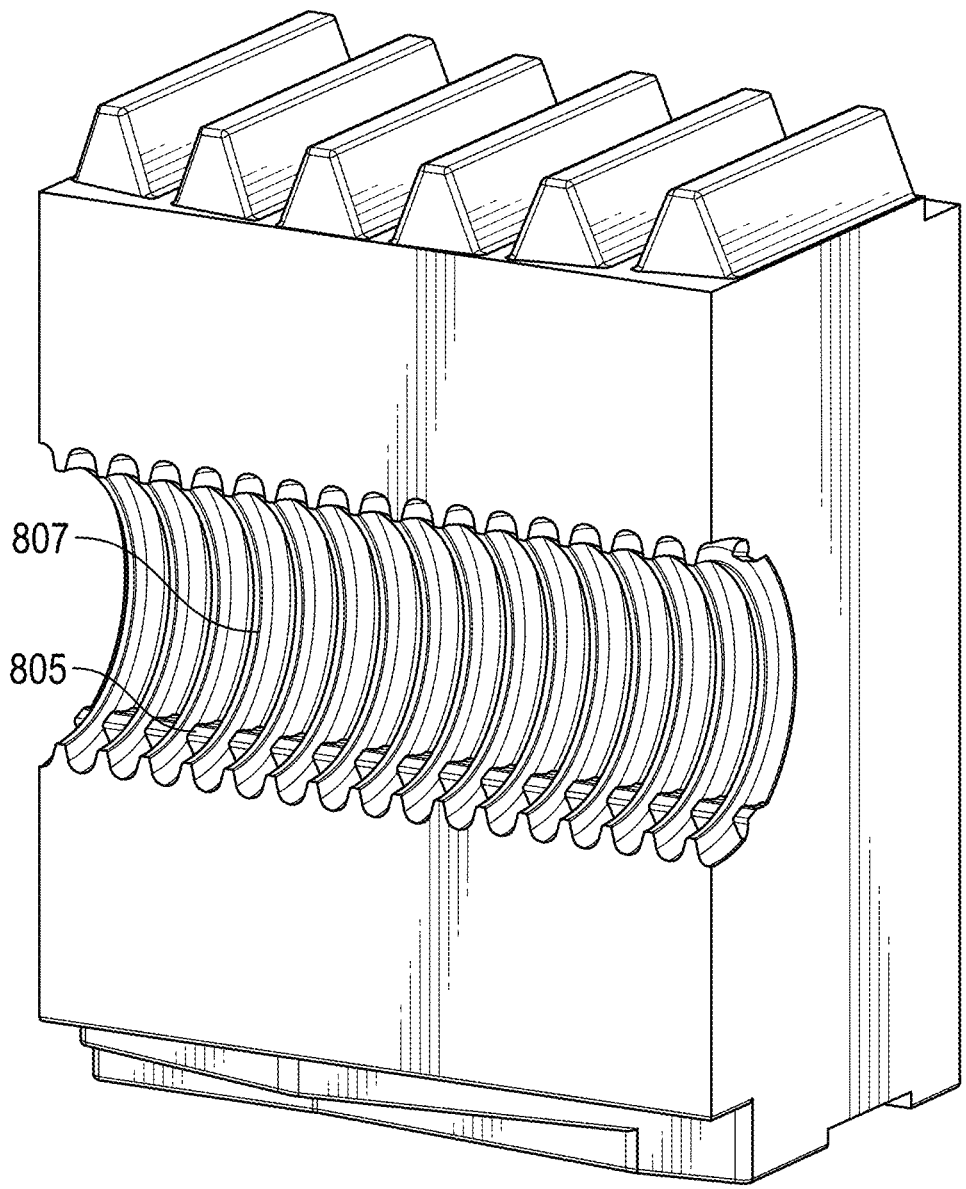
FIG. 8C is a corrugator block suitable for forming the tubular component of FIGS. 8A and 8B.

Reference is next made to FIGS. 8A and 8B, which show an alternative configuration for a ribbed, breathable tube 801 according to at least one embodiment. In FIG. 8B, raised ribs 803 are visible in the space between the ridges in the inside of the tube 801. FIG. 8C shows a corrugator suitable for forming the tube shown in FIGS. 8A and 8B. The block comprises raised portions 805 in between ridge portions 807, which will form the raised ribs when the tube is removed from the corrugator. It will be appreciated that still other reinforcing processes may used to supplement the tube in order to improve its performance characteristics still further (such as compliance, pull strength, resistance to flow with bending and crush resistance). Those processes may or may not be integrated with the tube forming process.

Figure 9:
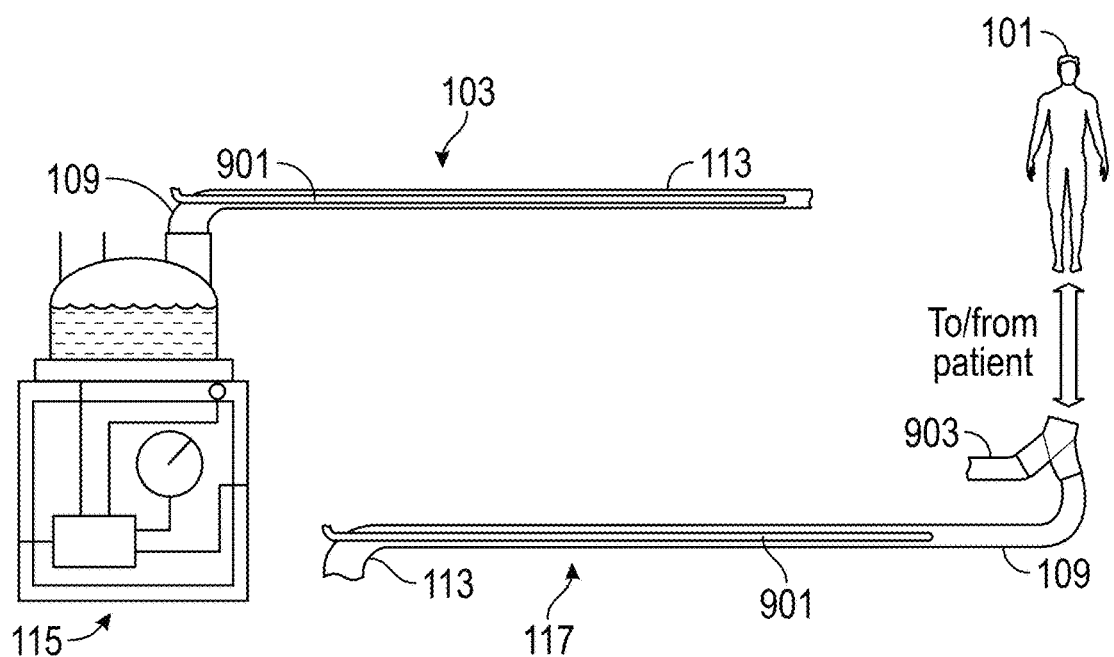
FIG. 9 is a schematic illustration of a breathing circuit according to at least one embodiment.

Reference is next made to FIG. 9, which shows another example medical circuit according to at least one embodiment. The circuit comprises two breathable tubes comprising a breathable foamed polymer as described above, namely an inspiratory tube 103 and an expiratory tube 117. The properties of the inspiratory tube 103 and the expiratory tube 117 are similar to the tubes described above with respect to FIG. 1. The inspiratory tube 103 has an inlet 109, communicating with a humidifier 115, and an outlet 113, through which humidified gases are provided to the patient 101. The expiratory tube 117 also has an inlet 109, which receives exhaled humidified gases from the patient, and an outlet 113. As described above with respect to FIG. 1, the outlet 113 of the expiratory tube 117 can vent exhaled gases to the atmosphere, to the ventilator/blower unit 115, to an air scrubber/filter (not shown), or to any other suitable location.

As described above with respect to FIG. 1, heating wires 901 can be placed within the inspiratory tube 103 and/or the expiratory tube 117 to reduce the risk of rain out in the tubes by raising the temperature above the saturation temperature.

In this example, the expiratory tube 117 comprises a connector (here, a Y-connector 903) for connecting to other components. For instance, the Y-connector 903 is configured to connect to the inspiratory tube 103 and a patient interface (not shown). Of course, the embodiment of FIG. 9 is simply an example configuration. A component according to at least one embodiment comprises a breathable, foamed polymer tube. The component can further comprise a suitable connector. Preferably, the connector also comprises the breathable, foamed polymer.

Figure 10:
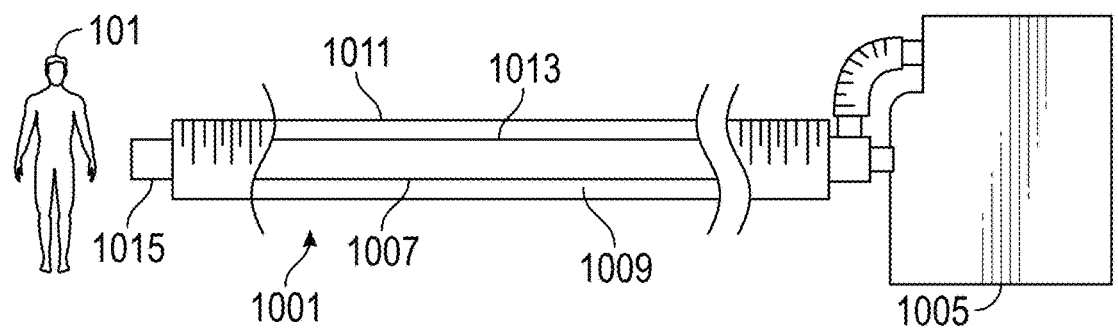
FIG. 10 is a schematic illustration of a component comprising a coaxial tube, according to at least one embodiment.

Reference is next made to FIG. 10, which shows a coaxial tube 1001 according to at least one embodiment. In this example, the coaxial tube 1001 is provided between a patient 101 and a ventilator 1005. Expiratory gases and inspiratory gases each flow in one of the inner tube 1007 or the space 1009 between the inner tube 1007 and the outer tube 1011. It will be appreciated that the outer tube 1011 may not be exactly aligned with the inner tube 1007. Rather, "coaxial" refers to a tube situated inside another tube. In use, water vapour, but not liquid water, is transmitted through a foamed, breathable tube wall, as explained below.

For heat transfer reasons, the inner tube 1007 carries the inspiratory gases in the space 1013 therewithin, while the expiratory gases are carried in the space 1009 between the inner tube 1007 and the outer tube 1011. This airflow configuration is indicated by arrows.

The inner tube 1007 is formed using the breathable foamed material described herein. Thus, humidity in the expiratory flow space 1009 may pass through the foamed breathable material to humidify the inspiratory flow in inspiratory flow space 1013. With the gases flow in a counter-flow arrangement as shown in the example, the breathable material provides substantial passive humidification of the inspiratory flow.

With a coaxial tube 1001, the ventilator 1005 may not become aware of a leak in the inner tube 1007. Such a leak may short circuit the patient 101, meaning that the patient 101 will not be supplied with sufficient oxygen. Such a short circuit may be detected by placement of a sensor at the patient end of the coaxial tube 1001. This sensor may be located in the patient end connector 1015. A short circuit closer to the ventilator 1005 will lead to continued patient 101 re-breathing of the air volume close to the patient 101. This will lead to a rise in the concentration of carbon dioxide in the inspiratory flow space 1013 close to the patient 101, which can be detected directly by a $CO_2$ sensor. Such a sensor may comprise any one of a number of such sensors as is currently commercially available. Alternatively, this re-breathing may be detected by monitoring the temperature of the gases at the patient end connector 1015, wherein a rise in temperature above a predetermined level indicates that re-breathing is occurring.

In addition to the above to reduce or eliminate the formation of condensation within either the inner tube 1007 or outer tube 1011, and to maintain a substantially uniform temperature in the gases flow through the coaxial tube 1001, a heater, such as a resistance heater wire, may be provided within either the inner tube 1007 or outer tube 1011, disposed within the gases spaces 1009 or 1013, or within the inner tube 1007 or outer tube 1011 walls themselves.

In an alternative embodiment of a coaxial tube 1001 where passive humidification is not desired, the foamed breathable wall may be the outer wall of the outer tube 1011. In this arrangement, the outer tube 1011 is in contact with ambient air, and the breathable wall allows water vapor exchange from the relatively humid expiratory gases with the ambient air. As a result, rain out can be managed and/or prevented.

Respiratory Mask

In the art of respiration devices, there are a well known variety of respiratory masks which cover the nose and/or mouth of a patient in order to provide a continuous seal around the nasal and/or oral areas of the patient's face, such that gas may be provided at positive pressure within the mask for consumption by the patient. The uses for such masks range from high altitude breathing (for example, aviation applications) to mining and fire fighting applications, to various medical diagnostic and therapeutic applications.

One application of such a mask is in respiratory humidification treatment. This system normally consists of a ventilator, humidifier, breathing circuit and patient interface, such as a mask or nasal cannula. In this form of treatment, humid air is supplied to the patient and as a result of the temperature difference between the humid air and the surrounding environment, the humid air can condense and form water droplets. In cases where treatment is prolonged (up to several days) these droplets may form water pools in the mask that can hamper the treatment, increase the risk of the patient inadvertently inhaling water and may cause discomfort and/or choking to the patient.

One requisite of such respiratory masks has been that they provide an effective seal against the patient's face to prevent leakage of the gas being supplied. Commonly, in prior mask configurations, a good mask-to-face seal has been attained in many instances only with considerable discomfort for the patient. This problem is most crucial in those applications, especially medical applications, which require the patient to wear such a mask continuously for hours or perhaps even days. In such situations, the patient will not tolerate the mask for long durations and optimum therapeutic or diagnostic objectives thus will not be achieved, or will be achieved with great difficulty and considerable patient discomfort.

Described below are various improvements in the delivery of respiratory therapy. In particular, a patient interface is described which is comfortable for the patient to wear and includes at least in part a water vapor permeable (breathable) area in the body of the patient interface made of a foamed breathable material as described herein. A large portion of the mask body (or the entire mask body) can be made of the foamed breathable material, taking advantage of the unique strength properties and high breathability.

Figure 11A:
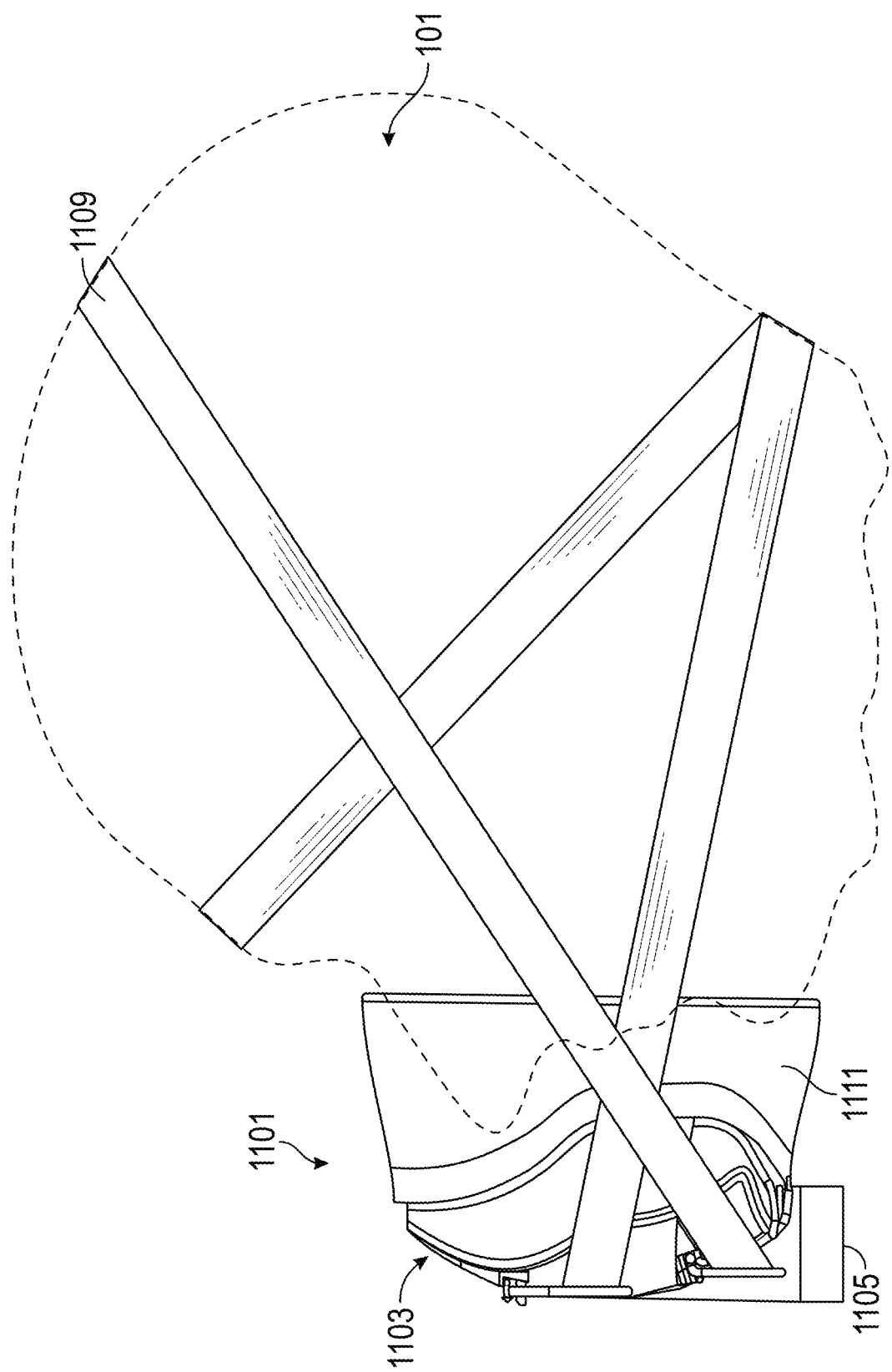
FIG. 11A is a side-plan view of a mask-type patient interface according to at least one embodiment.
Figure 11B:
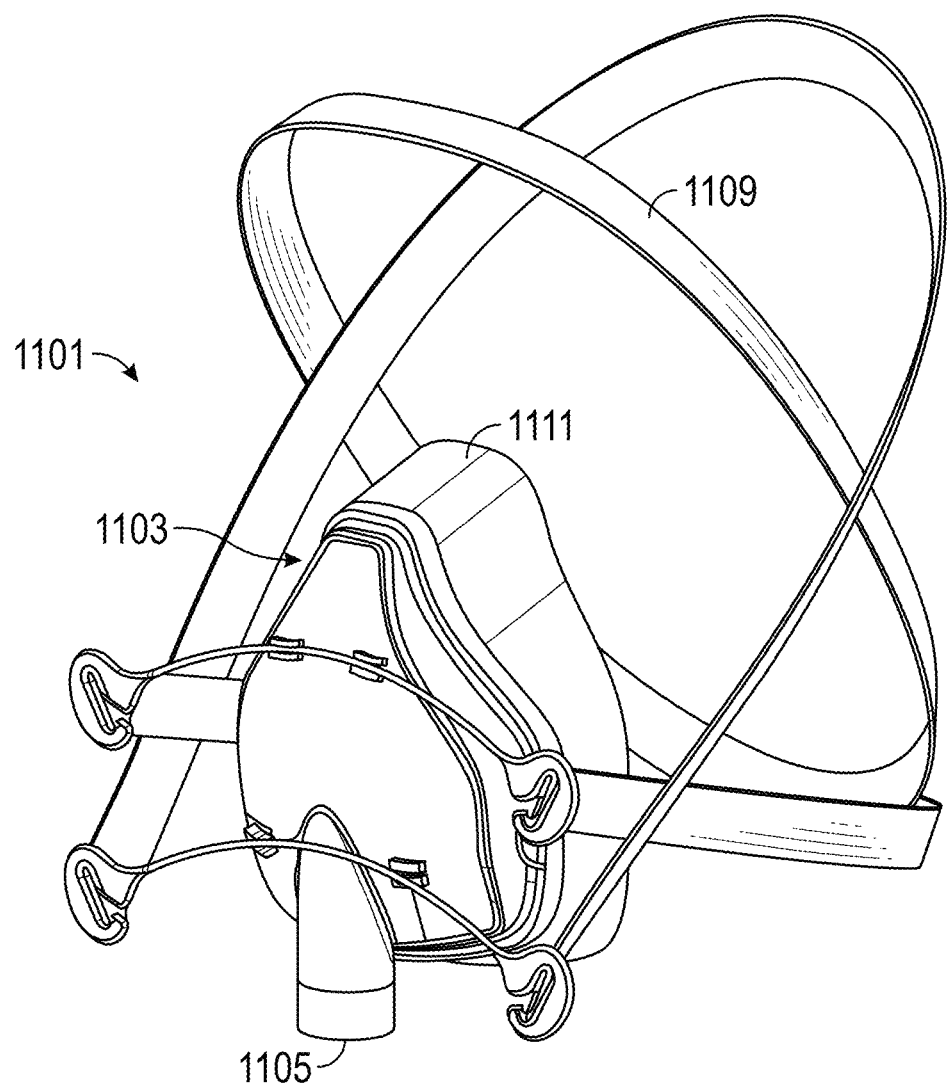
FIG. 11B is a front perspective view of the patient interface of FIG. 11A.

Reference is next made to FIGS. 11A and 11B, which show a respiratory mask 1101 according to at least one embodiment. It will be appreciated that this patient interface can be used in respiratory care generally or with a ventilator but will now be described below with reference to use in a humidified Positive Airway Pressure (PAP) system. It will also be appreciated that the following description can be applied to nasal masks, oral masks, oronasal masks, nasal prongs, and full-face masks due to the materials ability to be formed into a self-supporting, semi-rigid structure with high breathability, rather than being limited to the very thin film structures of the prior art.

The mask 1101 includes a hollow body 1103 with an inlet 1105 for connection to an inspiratory breathing tube. The mask 1101 is positioned on the face of the patient 101 with the headgear 1109 secured around the back of the head of the patient 101. The restraining force from the headgear 1109 on the hollow body 1103 ensures enough compressive force on the mask cushion 1111, to provide an effective seal against the patient 101 face. A number of engaging clips are connected to the body for the attachment of sliding members to connect the mask 1101 to the headgear 1109. The expiratory gases can be expelled through a valve (not shown) in the mask 1101, a further expiratory conduit (not shown), or any other such method as is known in the art.

The hollow body 1103 is constructed of a foamed polymer material as described herein. Such a material provides the requisite rigidity to the mask 1101 as well as being highly breathable. Previous attempts to provide a mask 1101 with breathable areas have required the use of thin membranes in order to achieve sufficiently high breathability. These membranes have had to be supported by additional reinforcing such as a strong mask frame and have also needed protection from damage. The areas of breathable membrane are usually supported within cutout areas of the mask frame. However, with the self-supporting breathable foamed polymers described herein, large portions of the mask 1101 (or the entire mask 1101) can be made of the foamed polymer, taking advantage of the unique strength properties and high breathability. The result is a self supporting semi-rigid mask 1101 that can be entirely (and highly) breathable.

Alternatively, the hollow body 1103 could have large areas cut out of the front surface such that the hollow body 1103 substantially consists of a framework having an outer circumference. Inserts made from the foamed, self-supporting breathable material described herein can be placed in the cut outs and bonded in order to prevent or reduce the formation of water droplets inside the mask 1101 during prolonged humidification treatment, thereby allowing moisture to escape to the surrounding ambient environment. A number of techniques exist as a means of attaching the breathable structure to the hollow body 1103 which may include gluing, sonic welding techniques, over-molding co-extrusion, or a snap-tight connection between the foamed breathable insert and the hollow body 1103.

It will be appreciated that additional reinforcing structures may also be provided, for example to a mask made of the foamed breathable material, to further customise the flexural properties of the component. For example, ribs may be added to the interior and/or exterior surface of the mask. Local variations of the wall thickness may also be employed to stiffen/weaken some areas to improve fitting to a patient facial features and/or to provide regions of even greater breathability. In particular, this type of reinforcement can be very useful to tailor the flexural properties of a component in particular directions where different loading patterns are anticipated. These advantages have not been possible or as easy to achieve with very thin breathable membranes used previously.

Nasal Cannula

Figure 12:
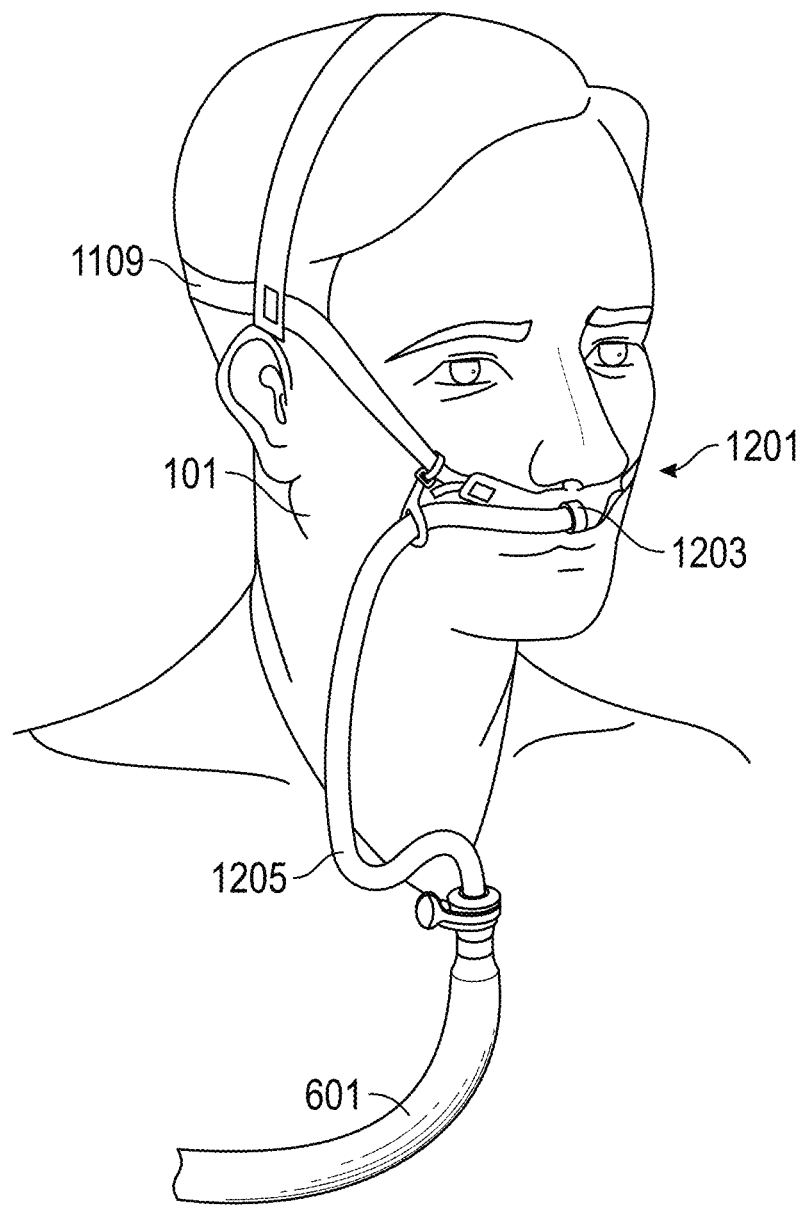
FIG. 12 is a front perspective view of a patient wearing a nasal-cannula-type patient interface according to at least one embodiment.

Reference is next made to FIG. 12, which shows a nasal cannula 1201 patient interface according to at least one embodiment. The nasal cannula 1201 comprises a cannula body 1203 and a short delivery tube 1205. The foamed breathable polymer described herein can be utilized in the cannula body 1203 and/or the short delivery tube 1205 to manage and/or prevent rainout from occurring within the gases spaces of these components. As also described earlier, application can also be found in the inspiratory breathing tube 601.

Catheter Mount

Yet another medical circuit component to which breathable foamed polymers can be applied is catheter mounts. A catheter mount connects between a patient interface component such as a mouth piece, nasal mask, or endotracheal tube and the dual limbs or breathing tubes of a breathing circuit. Connection with the dual limbs of the breathing circuit is generally via a Y-connector. In the patient inhalation and exhalation cycles, the dual limbs of the breathing circuit each have a distinct role: one as inhalation conduit and one as exhalation conduit. The catheter mount serves a dual role, transporting both inhaled and exhaled gases. Accordingly, the catheter mount can have significant disadvantages. A volume of exhaled air remains in the catheter mount between exhalation and inhalation. Accordingly some air is re-breathed by the patient. While not unacceptable, re-breathing is not generally desirable and where significant re-breathing is likely, a boost in oxygen supply levels may be required.

Gases inhaled by a patient are, in a well managed ventilation system, delivered in a condition having humidity near a saturation level and at close to body temperature, usually at a temperature between 33 and 37° C. (or about 33 and 37° C.). This temperature may be maintained by a heater in the inhalation breathing tube right up to the point where the gases enter the catheter mount. Gases exhaled by a patient are returned fully saturated and are subjected to further cooling as they flow through the catheter mount. Accordingly, although little condensation forms on the interior walls during patient inhalation, significant condensation levels may form during patient exhalation. The condensation, or rain out, occurring inside the catheter mount is particularly deleterious due to its proximity to the patient. Mobile condensate breathed or inhaled by a patient may lead to coughing fits or other discomfort.

Figure 13:
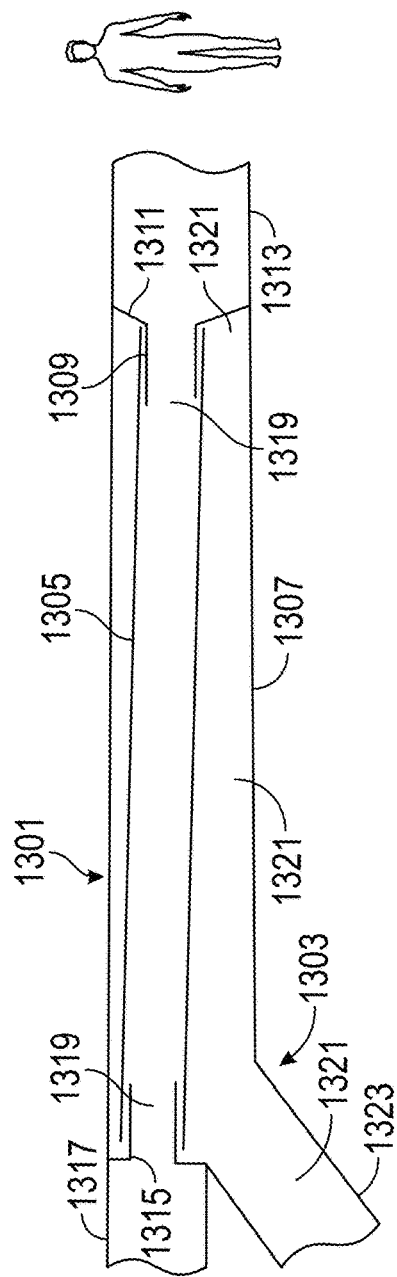
FIG. 13 is a schematic illustration of a catheter mount according to at least one embodiment.

Reference is next made to FIG. 13, which shows a catheter mount 1301 according to at least one embodiment. The catheter mount 1301 incorporates a Y-connector 1303 at the ventilator end. An inner tube 1305 extends coaxially with an outer tube 1307. The inner tube 1305 is supported at its patient end by an inner tube connector 1309, which in turn is supported via support struts 1311 from patient end connector 1313. The inner tube 1305 is supported at its other end by a second inner tube connector 1315, which forms part of the ventilator end Y-connector 1303.

The second inner tube connector 1315 communicates with the inspiratory breathing tube connector 1317. The outer tube 1307 has at least a part of its wall being made from a foamed breathable material as described herein. In certain embodiments, the outer tube 1307 is formed entirely from foamed breathable material.

Therefore, in use, the catheter mount 1301 has an inspiratory flow 1319 entering the catheter mount 1301. The inspiratory flow 1319 passes through the inner tube 1305 to exit to the patient through the patient end connector 1313. Upon patient exhalation, whether assisted or otherwise, expired gases 1321 pass through patient end connector 1313 and into the space surrounding the inner tube 1305. These expired gases 1321 pass along the inside of the wall of outer tube 1307 and out through the expiratory breathing tube connector 1323 of the Y-connector 1303. In passing through the catheter mount 1301 within the space between the inner tube 1305 and the outer tube 1307, water vapor may pass through the water vapour permeable foamed outer tube 1307. In certain embodiments, the entire of outer tube 1307 is breathable. In this way, although the expired gases 1321 may experience some temperature drop as they pass through the catheter mount 1301 to the expiratory breathing tube connector 1323, hand in hand with this temperature drop is a reduction in humidity by water vapor passing through the breathable foamed material of the outer tube 1307. Accordingly, relative saturation of the expiratory flow is reduced and rain out is thereby also reduced. The tube walls made of the foamed breathable material can have a wall thickness between 0.1 and 3 mm (or about 0.1 and 3.0 mm) and be sufficiently stiff to be self supporting or semi-rigid while still maintaining a high breathability.

The catheter mount 1301 incorporating the breathable foamed polymers described herein includes explicit division of the inspiratory and expiratory flows through the catheter mount 1301, thereby significantly reducing re-breathing. Rain out is also reduced by reducing the humidity of the expired gases even as the temperature of those gases reduces.

Component of an Insufflation or Smoke Evacuation System

Laparoscopic surgery, also called minimally invasive surgery (MIS), or keyhole surgery, is a modern surgical technique in which operations in the abdomen are performed through small incisions (usually 0.5 to 1.5 cm) as compared to larger incisions needed in traditional surgical procedures. Laparoscopic surgery includes operations within the abdominal or pelvic cavities.

During laparoscopic surgery with insufflation, it may also be desirable for the insufflation gas (commonly $CO_2$) to be humidified before being passed into the abdominal cavity. This can help prevent "drying out" of the patient's internal organs, and can decrease the amount of time needed for recovery. Even when dry insufflation gas is employed, the gas can become saturated as it picks up moisture from the patient's body cavity. The moisture in the gases tends to condense out onto the walls of the discharge limb or conduit of the insufflation system. The water vapour can also condense on other components of the insufflation system such as filters. Any vapour condensing on the filter and run-off along the limbs (inlet or exhaust) from moisture is highly undesirable. For example water which has condensed on the walls, can saturate the filter and cause it to become blocked. This potentially causes an increase in back pressure and hinders the ability of the system to clear smoke. Further, liquid water in the limbs can run into other connected equipment which is undesirable.

In abdominal surgery, for example, the abdomen is usually insufflated with carbon dioxide gas to create a working and viewing space. The gas used is generally $CO_2$ which is common to the human body and can be absorbed by tissue and removed by the respiratory system. It is also non-flammable, which is important because electrosurgical devices are commonly used in laparoscopic procedures. It has been common practice in laparoscopic surgery to use dry gases. However, it is also desirable for the $CO_2$ or other insufflation gas to be humidified before they are passed into the abdominal cavity. This can help prevent 'drying out' of the patient's internal organs, and can decrease the amount of time needed for recovery from surgery. Insufflation systems generally comprise humidifier chambers that hold a quantity of water within them. The humidifier generally includes a heater plate that heats the water to create a water vapour that is transmitted into the incoming gases to humidify the gases. The gases are transported out of the humidifier with the water vapor.

Surgical procedures frequently involve electrosurgery or electrocautery or increasingly the use of lasers. The use of these devices tends to create surgical smoke in the working space due to burning of tissue. Smoke evacuation systems which use a discharge arm or limb are commonly used to remove the smoke from the surgical site, so that a surgeon can see what he or she is doing, and so that this potentially harmful material does not remain within the body cavity post-surgery. One end of the discharge arm or limb is connected to, or inserted into, a second incision (or sometimes the same incision). A typical smoke evacuation system generally includes a trocar and a cannula at the end to aid insertion into the operative site. The smoke exits the insufflated abdominal area through the discharge limb. The discharge limb may be attached to the end of a laparoscopic instrument so as to provide evacuation close to the site where electrocautery takes place. Usually, the gases and smoke from the body cavity are filtered through a filter to remove particulate matter before they are vented to atmosphere. The filter may also be additionally designed to remove chemicals and any harmful micro-organisms from the surgical smoke.

Figure 14:
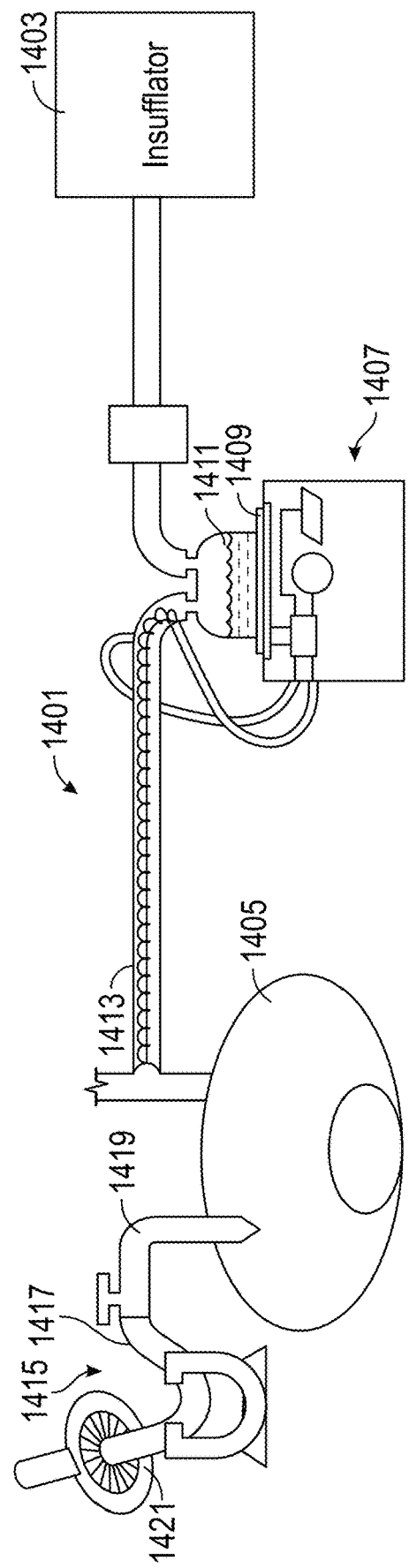
FIG. 14 is a schematic illustration of a humidified insufflation system according to at least one embodiment, comprising inlet and exhaust limbs.

Reference is next made to FIG. 14, which shows an insufflation system 1401, according to at least one embodiment. The insufflation system 1401 includes an insufflator 1403 that produces a stream of insufflation gases at a pressure above atmospheric for delivery into the patient 1405 abdominal or peritoneal cavity. The gases pass into a humidifier 1407, including a heater base 1409 and humidifier chamber 1411, with the chamber 1411 in use in contact with the heater base 1409 so that the heater base 1409 provides heat to the chamber 1411. In the humidifier 1407, the insufflation gases are passed through the chamber 1411 so that they become humidified to an appropriate level of moisture.

The system 1401 includes a delivery conduit 1413 that connects between the humidifier chamber 1411 and the patient 1405 peritoneal cavity or surgical site. The conduit 1413 has a first end and second end, the first end being connected to the outlet of the humidifier chamber 1411 and receiving humidified gases from the chamber 1411. The second end of the conduit 1413 is placed in the patient 1405 surgical site or peritoneal cavity and humidified insufflation gases travel from the chamber 1411, through the conduit 1413 and into the surgical site to insufflate and expand the surgical site or peritoneal cavity. The system also includes a controller (not shown) that regulates the amount of humidity supplied to the gases by controlling the power supplied to the heater base 1409. The controller can also be used to monitor water in the humidifier chamber 1411. A smoke evacuation system 1415 is shown leading out of the body cavity of the patient 1405.

The smoke evacuation system 1415 can be used in conjunction with the insufflation system 1401 described above or may be used with other suitable insufflation systems. The smoke evacuation system 1415 comprises a discharge or exhaust limb 1417, a discharge assembly 1419, and a filter 1421. The discharge limb 1417 connects between the filter 1421 and the discharge assembly 1419, which in use is located in or adjacent to the patient 1405 surgical site or peritoneal cavity. The discharge limb 1417 is a self-supporting tube (that is, the tube is capable of supporting its own weight without collapsing) with two open ends: an operative site end and an outlet end.

The gases supplied by the insufflation system 1401 are already humidified at the point of entry to the patient 1405 body cavity. As the body cavity is already moist and humid, the gases do not tend to lose moisture in the body, and can become fully saturated if they are not already at saturation point. If the gases are dry on entry to the body cavity, they tend to become humidified as they pass through the body cavity, picking up moisture from the damp atmosphere in the body cavity above the internal organs.

When these saturated gases pass out of the patient 1405 body cavity, they pass along the cooler walls of the discharge limb 1417, which is normally 1 m (or thereabout) in length. The moisture in the gases tends to condense out of the gas onto the walls of the discharge limb 1417, discharge assembly 1419, and/or the filter 1421. The vapor condensing on the filter 1421 and run-off along the discharge limb 1417 from moisture which has condensed on the walls, can saturate the filter 1421 and cause it to become blocked. This potentially causes an increase in back pressure and hinders the ability of the system to clear smoke.

The condensed moisture within the filter 1421 can cause the filter 1421 to become partially or totally blocked, leading to an increase in back pressure and reduced filter efficiency due to the blockage. This is disadvantageous because the increased back pressure hinders the ability of the system to effectively clear the surgical smoke. The surgical smoke remaining at the operational site within the surgical cavity or within the conduit of the evacuation system can be hazardous to the patient since the surgical smoke contains several potential toxins that may become entrained in the surgical cavity or tissue of the patient 1405. The vision of the surgeons can be obstructed or hindered due to the surgical smoke remaining at the operational site and not being evacuated, potentially leading to a hazardous working environment for the surgeons. The condensation may partially block the filter 1421 resulting in reduced filtration of toxins from the surgical smoke. This could result in potentially harmful substances like odors, surgical smoke, dead cellular matter, and so on escaping into the operating theater. These sorts of materials can be hazardous to the health and may lead to many health problems for medical practitioners and the patient.

At least one embodiment includes the realization that the use of a discharge limb 1417 having a breathable wall or the wall of the limb which includes breathable material will help to alleviate this problem. In particular, a foamed breathable material as described herein is especially suitable for forming this type of discharge limb 1417 conduit of an insufflation system because of the properties discussed in relation to foamed material, component, and breathing tube described earlier. A certain amount of moisture from the expelled gases passes through the wall of the discharge limb 1417 before reaching the filter 1421, and therefore there is less moisture in the gas to condense out of the gas and clog the filter 1421. Accordingly, the discharge limb 1417 is preferably made of a breathable, foamed material as described herein. The process detailed below for manufacturing a breathing tube can be applied directly to insufflation system tubes, including inlet or exhaust (smoke evacuation) limbs.

Method of Manufacture

Figure 15:
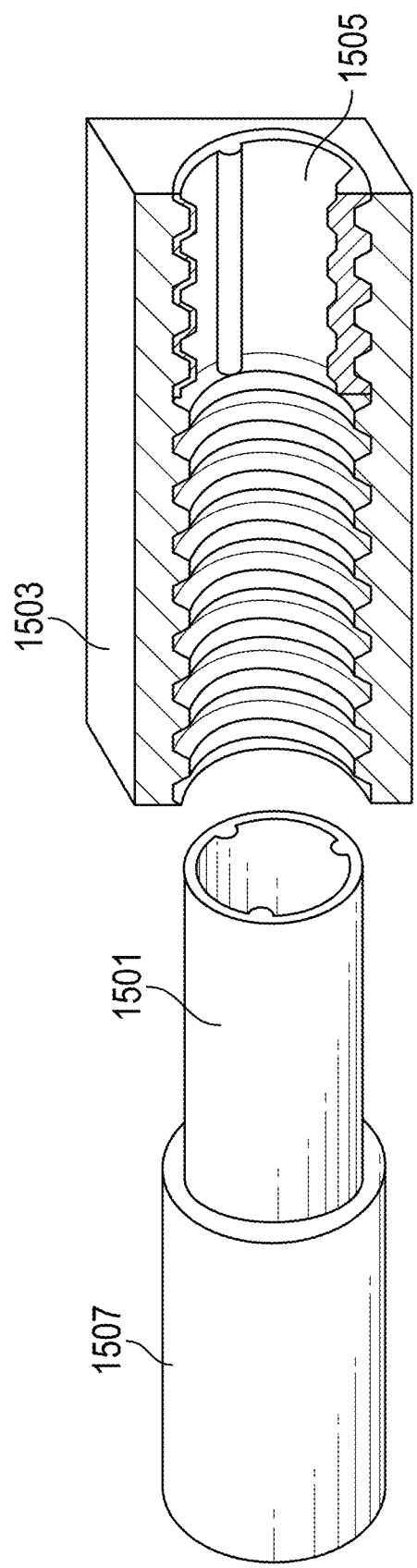
FIG. 15 is a schematic illustration of a method of manufacturing a component according to at least one embodiment.

Reference is next made to FIG. 15, which illustrates an example method of manufacturing a breathable component suitable for delivering humidified gas, such as a tube as in FIG. 2A and FIG. 2B or any other tube discussed herein, according to at least one embodiment.

In general, a method of manufacturing a component involves mixing a foaming agent into a polymeric base material and forming a liquefied mixture. The foaming agent is allowed to release gas bubbles into the base material portion of the liquefied mixture. Then, the release of gas bubbles is arrested and the mixture is solidified to form the desired component. Desired properties of the finished component are discussed above.

In at least one embodiment, the process used to make a component such as a breathing tube involves extruding a molten extrudate 1501 into a corrugator 1503 to form the desired component, such as a tube 1505. In certain embodiments, the polymeric base material for the extrudate has a diffusion co-efficient greater than $0.75 \times 10^{-7}$ cm$^2$/s (or thereabout). The base material can have the following stiffness properties: (a) a tensile modulus greater than 15 MPa (or about 15 MPa), which can be desirable for urethane-thermoplastic-elastomer-based base materials (or TPU-based base materials, as defined by ISO 18064:2003(E)); or (b) a tensile modulus greater than 100 MPa (or about 100 MPa), which can be desirable for copolyester-thermoplastic-elastomer-based base materials (or TPC-based base materials, as defined by 18064:2003(E)), such as ARNITEL®-based base materials. These foregoing properties are simply by way of example. A base material need not have these properties to produce a foamed material with the desired breathability and stiffness, and the example modulus numbers are not expressly limited to TPU and TPC-based base materials.

An extruder such as a Welex extruder equipped with a 30 mm diameter screw and a 12 mm annular die head with a gap of 0.5 mm has been found to be suitable producing low cost tubes quickly. After exiting the extruder die head 1507, the molten tube 1501 can be passed between a series of rotating molds or blocks on the corrugator 1503. A corrugator such as those manufactured and supplied by UNICOR® also has been found to be suitable. This forms a corrugated tube 1505.

The above-described method is simply by way of example. Alternate methods for forming components comprising the foamed materials described herein are also suitable. For instance, another method for manufacturing a breathable component involves extruding a strip of foamed material, winding the foamed strip on a mandrel, and sealing the seams of the wound strip with a bead (such as a bead of the foamed material).

Foaming during the extrusion process can be done in several ways, including physical foaming and chemical foaming.

In physical foaming, the foaming agent is an inert gas (e.g. $CO_2$ or $N_2$), which is injected in the extruder barrel at a flow rate and a pressure sufficiently high to dissolve it into the molten polymer. For example, a pressure greater than 100 bar (or about 100 bar) and a flow rate as little as 1% (or about 1%) of the polymer flow rate may be suitable. Preferably, a nucleating agent is also introduced into the polymer to create sites for the foam bubbles to expand. An example of this method includes using a commercial unit by Sulzer to inject inert gasses at the end of the extruder barrel and mixing the gas with static mixers prior to die exit.

Chemical foaming involves the addition of a chemical that induces a chemical decomposition reaction (endothermic or exothermic) when heated, thereby releasing gases. The gases dissolve into the polymer melt during the extrusion process due to the pressure in the melt being higher than the gases' critical solubilization pressure. The gases come out of solution when encountering a pressure drop, such as that at (or soon after) the die head exit. Foaming agents act as plasticizers, thereby reducing the viscosity of the melt. A reduction in viscosity translates to a reduced melt pressure for a given temperature, shear rate, and die head geometry. Accordingly, care should be taken to ensure that the gases do not foam prematurely by keeping the pressure in the extruder above the critical solubilization pressure. This pressure can be maintained by controlling the shear rate at the die head and/or the temperature of the melt.

An example process suitable for foaming the material in the extruder prior to corrugating the tubes involves adding a chemical foaming agent in amounts of 0.3 to 1.5% (or about 0.3 to 1.5%) by weight to a base polymer (such as ARNITEL® VT 3108). This can be achieved by directly mixing a foaming agent powder (such as HYDROCEROL® CT 671 or an equivalent) with the base polymer or by first mixing a foaming agent "masterbatch" (that is, a mixture of a carrier polymer, such as polyethylene, and active foaming agent (such as HYDROCEROL® BIH-10E or an equivalent) at 80/20% or about 80/20% by weight of carrier polymer to active foaming agent before feeding the mixture into the feed zone of the extruder barrel. In the first case, the foaming agent powder is the foaming agent. In the second case, the foaming agent masterbatch is the foaming agent. HYDROCEROL® CT 671 has a decomposition temperature of 160° C. and a solubilization pressure of 60 bar. ARNITEL® VT 3108 has a melt temperature of 185° C. Therefore, in this extrusion example, the processing temperatures can be dropped by 10 to 20° C. (or about 10 to 20° C.) to prevent the pressure from dropping below the critical value, because dropping melt temperature increases viscosity The shear rates (via extruder speed) are set high enough to ensure that the pressure is higher than the critical pressure as well as to ensure that the foaming agent is mixed well with the molten polymer. Once the polymer exits the die head, foaming starts to take place and bubbles can be seen to nucleate, and expand until the polymer is cooled to a point where the forces of bubble expansion are lower than the forces required to deform the molten polymer (for example, below the melting temperature of the polymer or below the activation temperature of the foaming agents, where the foaming reaction starts/stops). Cooling begins when the polymer enters the corrugator and is molded onto the corrugator blocks. Those blocks, in turn, are cooled by the corrugator water supply and the forming vacuum.

Once foamed, the component consists of a corrugated tube having thousands of foamed cell voids distributed throughout the thickness of the component wall. It has been found that for a typical breathing tube component, a void size diameter not exceeding about 700 μm (95% confidence level) in the transverse direction can produce a desirable product. However, it is advantageous that the void size diameter in the transverse direction is smaller than 700 μm to prevent voids extending entirely through the thickness of the tube wall and causing a leak path. For example, in some embodiments the void size diameter in the transverse direction may not exceed about 500 μm (95% confidence level). It has also been found that a void size diameter in the transverse direction between 75 and 300 μm (or about 75 and 300 μm) produces a high quality product for medical circuits. The maximum void size diameter in the transverse direction will depend on the minimum wall thickness of the component. For example, the maximum void size in the transverse direction can be limited to less than half (or about half) of the minimum wall thickness. However, the maximum void size diameter in the transverse direction can be less than one third (or about one third), less than 30% (or about 30%), or even less than one quarter (or about one quarter) of the minimum wall thickness.

Figure 16A:
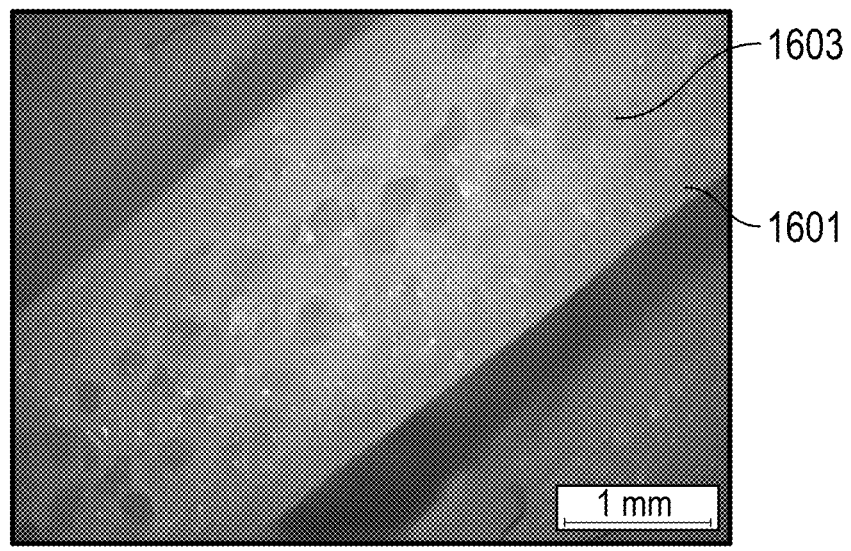
FIGS. 16A and 16B are micrographs showing an extruded foam polymer having an outer skin layer.
Figure 16B:
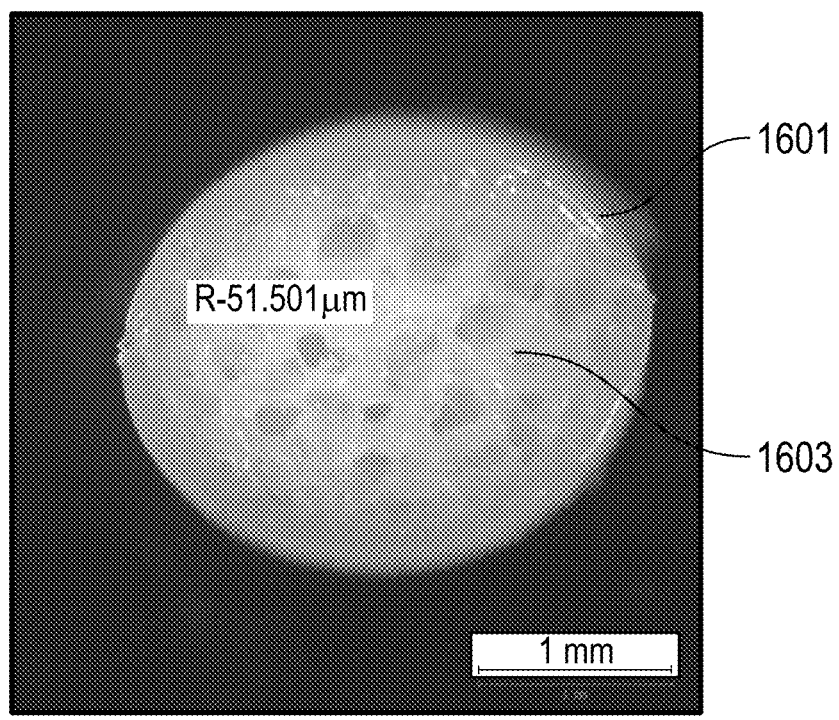

As discussed above, the foaming bubbles stop growing as the material cools. It has been found that quickly cooling results in the formation of two zones through the thickness of the wall. FIGS. 16A and 16B show an extruded foamed material comprising two zones, according to at least one embodiment. A first zone 1601, 100 μm thick (or about 100 μm thick), forms as an outer "skin" of closed cell foamed material on the surface that contacts the corrugator molds/blocks. In this zone, the average and maximum void size is smaller and the skin is less likely to form a leak path through the wall. In the remaining second zone 1603, the material cools slower and larger voids can result in open cells. Accordingly, at least one embodiment includes the realization that it is desirable to cool the material quickly after foaming has initiated as it exits the die head.

The tube is cooled as part of the corrugation process once it comes into contact with the corrugator blocks (the metal blocks where the profile shape is machined into). Quick cooling is achieved by maintaining the corrugator blocks temperature to a low value, for instance, 15° C. (or about 15° C.), using a coolant such as water. Quick cooling may also be achieved by modifying the melt temperature at the exit of the extruder (and before touching the blocks) to a temperature near the melting point of the polymer so that the molten plastic solidifies quickly. This can be accomplished with an air gap between the extruder and corrugator, which can be augmented with cooling gases and/or air jets or a liquid bath, such as a water bath. Quick cooling can also achieved by increasing the vacuum pressure in the blocks so that the polymer gets "sucked" into the metal shape very quickly and thus cools down before the bubbles have time to expand fully. One or more of these techniques can be used alone or in combination to achieve quick cooling in various embodiments.

The formation of the skin depends not only on quick cooling. Skin formation also depends on the material composition (such as the level of foaming), the extruder speed, the melt temperature and pressure, the gap before cooling, the water temperature and length of the bath, and finally the haul off speed (a mechanism that pulls the formed tube from the extruder). Quick cooling depends mainly on the haul off speed, the gap, and the water temperature.

The resulting skin thickness can be between 5 and 10% (or about 5 and 10%) of the wall thickness, for example, between 10 and 50 μm (or about 10 and 50 μm). Each of the first zone and the second zone have voids. In certain embodiments, no more than 5% (or about 5%) of the voids in the first zone exceed a diameter of 100 μm. The voids in the second zone are larger than the voids in the first zone. For example, in some embodiments no more than 5% (or about 5%) of the voids of said second zone of foamed material exceed a diameter of 700 μm.

Figure 17:
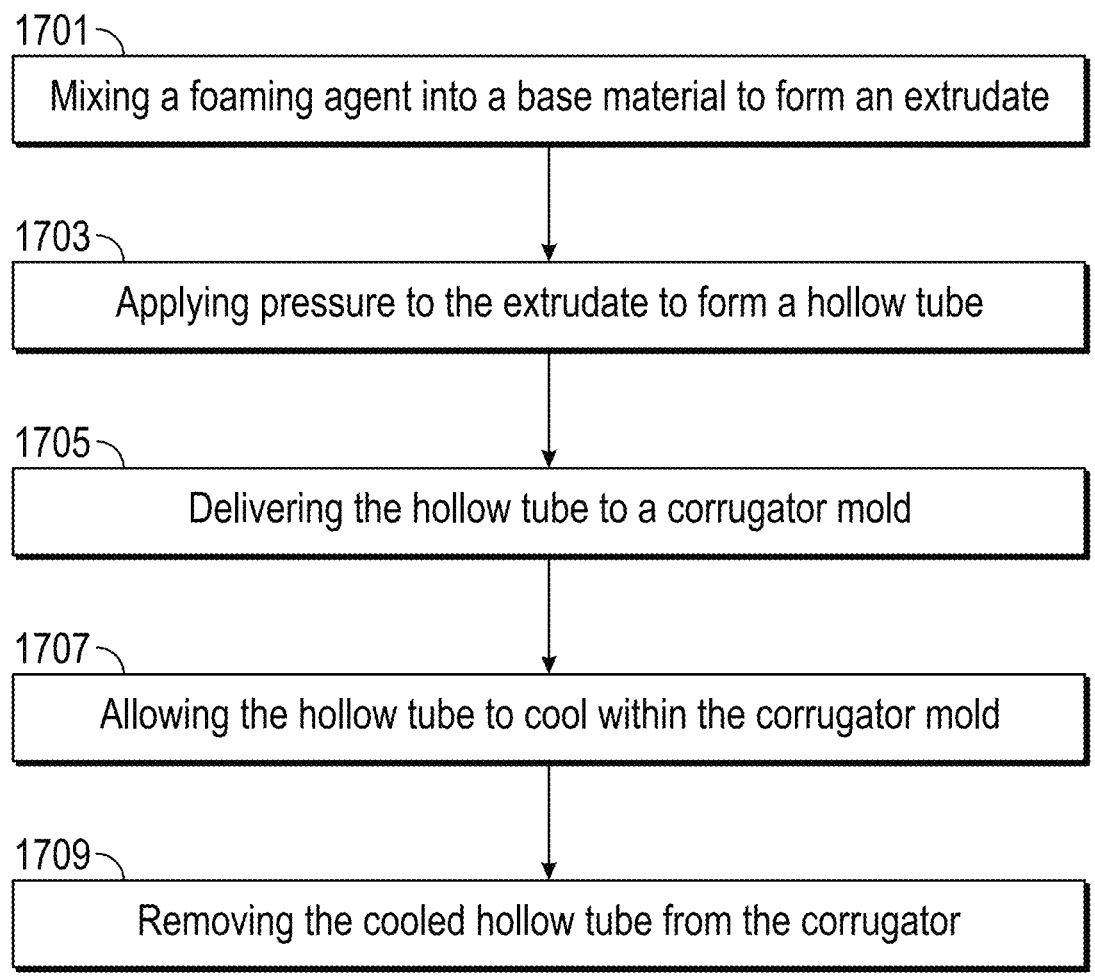
FIG. 17 is a flow chart showing a method of manufacturing a component according to at least one embodiment.

Reference is next made to FIG. 17, which describes an example method of manufacturing a tube according to at least one embodiment. In the example method, a foaming agent is first mixed into a base material to form an extrudate, as shown in block 1701. The base material comprises one or more breathable thermoplastic elastomers having a diffusion coefficient greater than $0.75 \times 10^{-7}$ cm$^2$/s (or about $0.75 \times 10^{-7}$ cm$^2$/s) and a tensile modulus greater than about 15 MPa. Pressure is then applied to the extrudate using an extruder to form a hollow tube, as shown in block 1703. The hollow tube is delivered to a corrugator mold, as shown in block 1705. The hollow tube is allowed to cool within the corrugator mold, thereby allowing the foaming agent portion of the extrudate to release gas bubbles, as shown in block 1707. Finally, the cooled hollow tube is removed from the corrugator, as shown in block 1709, thereby forming a tube comprising solid thermoplastic elastomer and voids formed by the gas bubbles. In this example, the resulting tube has a wall thickness between 0.1 and 3.0 mm (or about 0.1 and 3.0 mm). And the maximum void size is less than one third (or about one third) of the minimum wall thickness and the void fraction of the corrugated tube is greater than 25% (or about 25%).

Measurements

Properties, including modulus, void fraction, mass, diameter, thickness, and diffusivity, are referred to above. The following provides preferred methods for measuring these properties. All measurements are at room temperature (23° C. or thereabout).

A. Modulus

Tensile measurements were carried out to determine the force/strain relationship of foamed corrugated tubes under constant extension. It was determined that this relation is typically linear for up to 10% extension. An Instron machine equipped with a 500 N load cell was used to carry out this experiment and 200 mm long corrugated tube samples were used as the test specimens.

A 2D axi-symmetric finite element (numerical) model was implemented to extract the material's Young's modulus from the experiment. The geometry in this model was constructed from measurements of the corrugated tubes. The model included a linearly elastic (Hookean) material behavior for the analysis of a modulus of (E). The use of linear elastic materials in the model is justified under the small extension conditions. The model was constrained from one end and pulled from the other with a constant load to simulate a similar behaviour to that seen on the Instron machine. Extension values at different moduli (E) were extracted from the model and the model data was compared to those in the Instron experiment according to the following equality:

$$\left[\frac{FL}{\varepsilon}\right]_{model} = \left[\frac{FL}{\varepsilon}\right]_{Instron}$$

where
F represents force
L represents specimen length, and
ε represents extension.

The modulus was chosen as the value that matches this equality between the model and the experiment. A validation experiment was carried out using a corrugated tube with a known modulus and the results agreed well with the numerical model.

B. Void Fraction Measurement

The void fraction ($\phi_v$) of the foamed polymer sample is defined in EQ. 1 as:

$$\phi_v = 1 - \left[\frac{\rho(S)}{\rho(P)}\right] \tag{1}$$

where ρ(S) is the density of a foamed polymer sample and ρ(P) is the density of the corresponding unfoamed polymer. Two example methods for measuring ρ(S) are the buoyancy method and the displacement method, discussed below.

The buoyancy method involves measuring the mass of a sample suspended in air ($M_1$) and then measuring the mass of the sample suspended in a fluid of a known, low density ($M_2$), such as heptane. The density of the foamed polymer sample can be calculated according to EQ. 2 as follows:

$$\rho(S) = \frac{M_1 \rho_F}{M_1 - M_2} \tag{2}$$

where $\rho_F$ represents the density of the suspension fluid. The buoyancy method is suitable for smaller samples, when the density of the sample is larger than the density of the suspension fluid. For example, if heptane is employed as the suspension fluid, this method is suitable for foamed ARNITEL® samples having a void fraction less than 45%.

The displacement method involves calculating the volume of a sample by measuring the amount of liquid that it displaces. Using a digital height meter, the height of the markings on an empty graduated cylinder are measured. This provides a calibrated correlation between height and volume. A liquid is placed in the cylinder and, measuring to the bottom of a concave meniscus or to the top of a convex meniscus, the height of the liquid in the cylinder is determined. This gives an initial volume ($V_1$). Then a sample of foamed polymer of known dry mass ($M_1$) is placed in the liquid and the height of the liquid in the cylinder is again determined. This gives a final volume ($V_2$). The density of the foamed polymer sample can be calculated according to EQ. 3 as follows:

$$\rho(S) = \frac{M_1}{V_2 - V_1} \tag{3}$$

While the displacement method requires a larger sample to get adequate precision, it does allow for measurement of lower density samples, because a sample can be submerged and held in place.

C. Mass

All masses were obtained using a Vibra AJ-420 CE tuning fork microbalance manufactured by Shinko Denshi Co. (Plant #504068).

D. Thickness and Diameter

Sample thicknesses and/or diameters can be obtained in the following fashions.

For tubular samples, a Mitutoyo digital calliper (Model CD-8 CSX) can be used to measure diameter. Sample diameters can be measured at multiple points and a simple average of these measurements taken as the sample diameter.

For film samples, thicknesses can be obtained at many points using a Mitutoyo vernier micrometer D(0-25 mm) RH NEO MODELSHOP. Again, a simple average can be taken as the sample thickness.

For measuring thickness of a corrugated tubular sample, the tube can be cut into sections and numerous measurements taken using the digital calliper at various positions along the profile. An area-weighted average thickness can be calculated. In the alternative, a calibrated microscope, such as a Meiju Techno Microscope, can also be used to measure the thickness of a corrugated tubular sample. The method involves taking many measurements (typically more than 90) of both the peak and valley thicknesses along the length of the tube at different positions around the circumference. This is accomplished by cutting the tube in half, but along a helical path that covers 45 corrugations per helical turn.

E. Diffusivity

The time dependent sorption and desorption of water by polymeric systems is a function of the diffusivity of water in the polymer. Crank J. The mathematics of diffusion. 2nd ed. Oxford: Clarendon Press; 1975 gives detailed descriptions of how experimental data can be analysed to yield the diffusion coefficient of water in a polymer. Pages 46-49, 60, 61, and 72-75 of Crank are hereby incorporated by this reference.

According to Crank, when the diffusion coefficient D is a constant, the desorption/absorption of water in a sample of thickness 2l is defined by EQ. 4.

$$\frac{M(t)}{M(\infty)} = 1 - \sum_n A_n \exp(-\beta_n^2 D t) \tag{4}$$

where:

$$\frac{M(t)}{M(\infty)}$$

represents fractional mass loss or mass gain
M(t)=m(t)−m(0), grams
M(∞)=m(∞)−m(0), grams
m(0) represents mass at time=0, grams
m(t) represents mass at time=t, grams
m(∞) represents mass of the sample at very long times, grams
n represents the nth term in the infinite sum $$A_n = \frac{8}{(2n+1)^2 \pi^2} \tag{5}$$

$$\beta_n = \frac{(2n+1)\pi}{2l} \tag{6}$$

D represents the diffusion coefficient, cm²/sec
t represents time, sec, and
2l represents the thickness of the sample, cm.

In EQ. 4, the leading exponential for n=1 (that is, with $A_1$ and $\beta_1$) becomes the dominant term for values of $$\frac{M(t)}{M(\infty)} > 0.4.$$

An alternative representation for $$\frac{M(t)}{M(\infty)}$$

is obtained by solving the diffusion equation using Laplace transforms. The result is given by Crank and reproduced below as EQ. 7.

$$\frac{M(t)}{M(\infty)} = 2\sqrt{\frac{Dt}{l^2}} \left\{ \sqrt{\frac{1}{\pi}} + 2\sum_n (-1)^n \mathrm{ierfc}(\gamma_n) \right\} \tag{7}$$

where $$\gamma_n = \frac{nl}{\sqrt{Dt}}$$

$$\mathrm{ierfc}(x) = \left[ \frac{\exp(-x^2)}{\sqrt{\pi}} \right] - x\,\mathrm{erfc}(x),$$

and erfc(x) represents the complementary error function of x. At short times, for values of $$\frac{M(t)}{M(\infty)} < 0.4,$$

only the term $$\sqrt{\frac{1}{\pi}}$$

inside the curly braces {·} contributes most significantly. EQ. 7 suggests that plots of $$\frac{M(t)}{M(\infty)}$$

versus √t will be straight lines with a slope equal to $$\frac{2}{l}\sqrt{\frac{D}{\pi}}.$$

Figure 18:
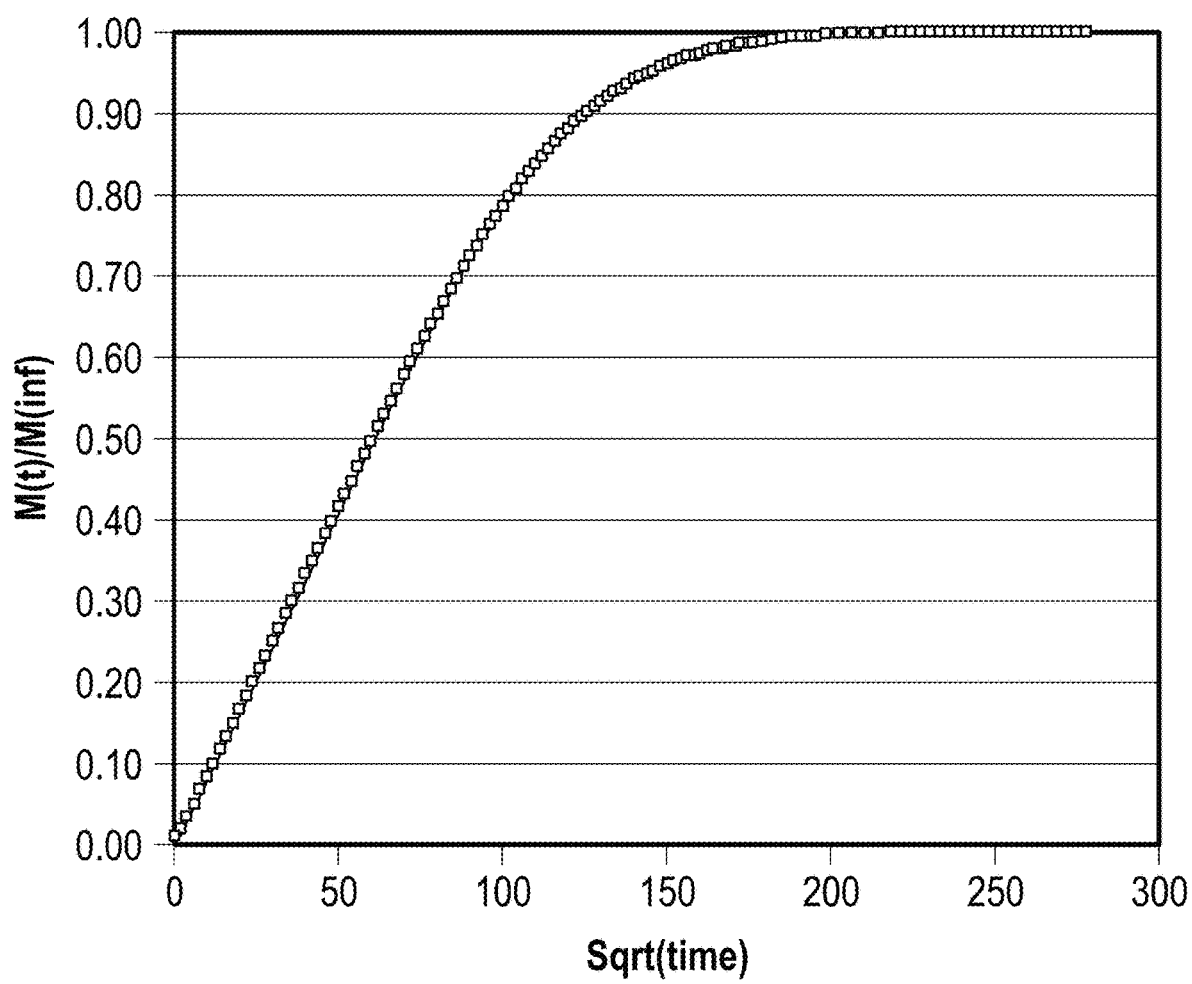
FIG. 18 is a plot of an ideal sorption/desorption curve with constant diffusivity.
Figure 19:
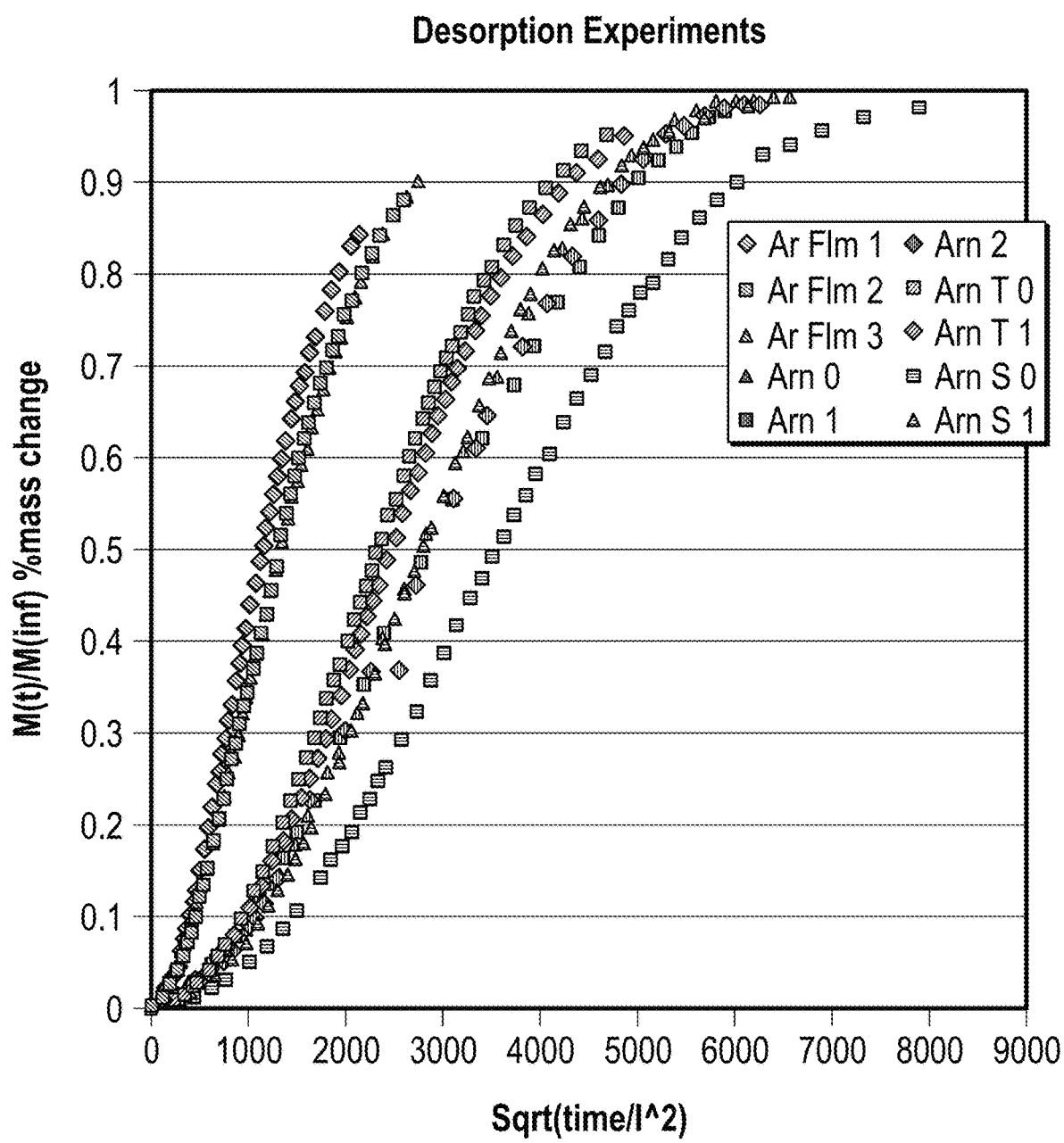
FIG. 19 is a plot of representative experimental desorption curves.

FIG. 18 shows an idealized sorption/desorption curve with a constant diffusion coefficient D=3.0×10⁻⁷ cm²/sec and l=0.075 cm. Actual experimental curves, as shown in FIG. 19, look different than the idealized curve. Compared with the idealized curve, the fractional mass change in the experimental curves look retarded in time, and the overall experimental curves have a sigmoid shape. A sigmoid shape is obtained when desorption of water from the film is limited by the rate of evaporation at the surfaces of the film. This is mathematically described by the boundary condition in EQ. 8 at the surface of the material.

$$-D\frac{\partial C}{\partial x} = \alpha(C_0 - C_s) \qquad (8)$$

where
- $C_0$ represents the concentration in the film that would be in equilibrium with the external environment, g/cm$^3$
- $C_s$ represents the concentration of water just inside the surface, g/cm$^3$, and
- $\alpha$ represents a constant related to the rate of evaporation at the surface, cm/sec.

With evaporation, the analog to EQ. 1 can be expressed according to EQ. 9.

$$\frac{M(t)}{M(\infty)} = 1 - \sum_n A_n \exp\left(\frac{-\beta_n^2 Dt}{l^2}\right) \qquad (9)$$

where $$A_n = \frac{2L^2}{\beta_n^2(\beta_n^2 + L^2 + L)} \qquad (10)$$

$$L = \frac{l\alpha}{D}$$

and $\beta_n$ is a solution to the equation $$L = \beta_n \tan(\beta_n) \qquad (11)$$

Again, at longer times, when $$\frac{M(t)}{M(\infty)} > 0.4,$$

EQ. 9 is dominated by the leading (n=1) exponential, with $A_1$ and $\beta_1$. As $\alpha$, and therefore L, become larger, then $A_n$ and $\beta_n$ reduce to the definitions in EQS. 5 and 6.

Because of strong coupling between $\beta$, L, and D in EQ. 9, it can be desirable to also derive D from the data at short times. In the ideal diffusion case, the diffusion coefficient D was extracted by looking at the experimental data at short times using EQ. 7. The corresponding equation for EQ. 7 with the boundary condition given by EQ. 8 was not shown by Crank. Accordingly, Laplace transform solutions were derived through terms n=2. For values of $$\frac{M(t)}{M(\infty)} < 0.4,$$

EQ. 12 provides a very close approximation of the actual results.

$$\frac{M(t)}{M(\infty)} = \frac{2}{l}\sqrt{\frac{Dt}{\pi}} - \qquad (12)$$

-continued $$\frac{1}{L}\left\{1 - \left(\exp\left[L\sqrt{(Dt/l)^2}\right]\right)\left(\mathrm{erfc}\left[L\sqrt{Dt/l}\right]\right)\right\} + \text{higher order terms}$$

At short times the higher order terms are small and can be neglected.

Using the above derivation, an example method for calculating diffusivity is provided as follows:

1. Collect experimental data on $$\frac{M(t)}{M(\infty)}$$

(the fractional mass loss or mass gain) over time (t) in seconds. For a desorption experiment, this is done by first equilibrating a sample of known dry weight to water vapor at a controlled RH and then measuring the weight of the sample at various times, including its initial value m(0). Measurements are taken until the weight no longer changes, m(∞). All measurements are taken while blowing dry air over the sample at rates from 10-30 L/min (or about 10-30 L/min) to reduce the effect of evaporation on the experimental observations.

2. Calculate the grams of water per gram of dry polymer (W %) at each time. From this data and other experiments calculate the value of l(t) at each time, where 2l(t) represents the thickness of the sample in cm.

3. Select initial values (or first estimates) of L and D.

4. Define a function G(t) derived from EQ. 12 above according to EQ. 13:

$$G(t) = \frac{M(t)}{M(\infty)} + \frac{1}{L}\left\{1 - \left(\exp\left[L\sqrt{(Dt/l(t))^2}\right]\right)\left(\mathrm{erfc}\left[L\sqrt{Dt/l(t)}\right]\right)\right\} \qquad (13)$$

5. Calculate the values of G(t) using the initial estimates of L and D.

6. Plot G(t) versus $$\frac{1}{l(t)}\sqrt{t}$$

and, from the slope of the first four data points, calculate a comparison value for D using EQ. 14:

$$G(t) = \frac{2}{l(t)}\sqrt{\frac{Dt}{\pi}} \qquad (14)$$

7. Using the initial value of L in step 3, repeat steps 5 and 6 until D converges. This defines D and L as input parameters for subsequent steps.

8. Using the value of L from step 3, calculate the first six roots of $\beta_n$ (n=1 . . . 6) according to EQ. 11.

9. From experiment, calculate the value of $$\ln\left[1 - \frac{M(t)}{M(\infty)}\right] \qquad (15)$$

at each time t. From EQ. 9 at longer times, EQ. 15 is equivalent to the relationship given below in EQ. 16:

$$\ln\left[1 - \frac{M(t)}{M(\infty)}\right] = \ln(A_1) - \left[\frac{\beta_1^2 Dt}{l(t)^2}\right] \quad (16)$$

10. Accordingly, the values calculated according to EQ. 15 are next plotted against $$\frac{t}{l(t)^2}.$$

11. From the slope of this plot in the range where $$0.35 < \left[1 - \frac{M(1)}{M(\infty)}\right] < 0.65$$

and from the value of $\beta_1$ calculated in step 8, a new value of D can be calculated using EQ. 16.

12. Adjust the value of L in step 3 and repeat steps 4 through 11 until the value of D in step 11 and the value of D in step 7 are the same value. This defines unique values for L and D that satisfy both EQ. 9 and EQ. 12.

Figure 20:
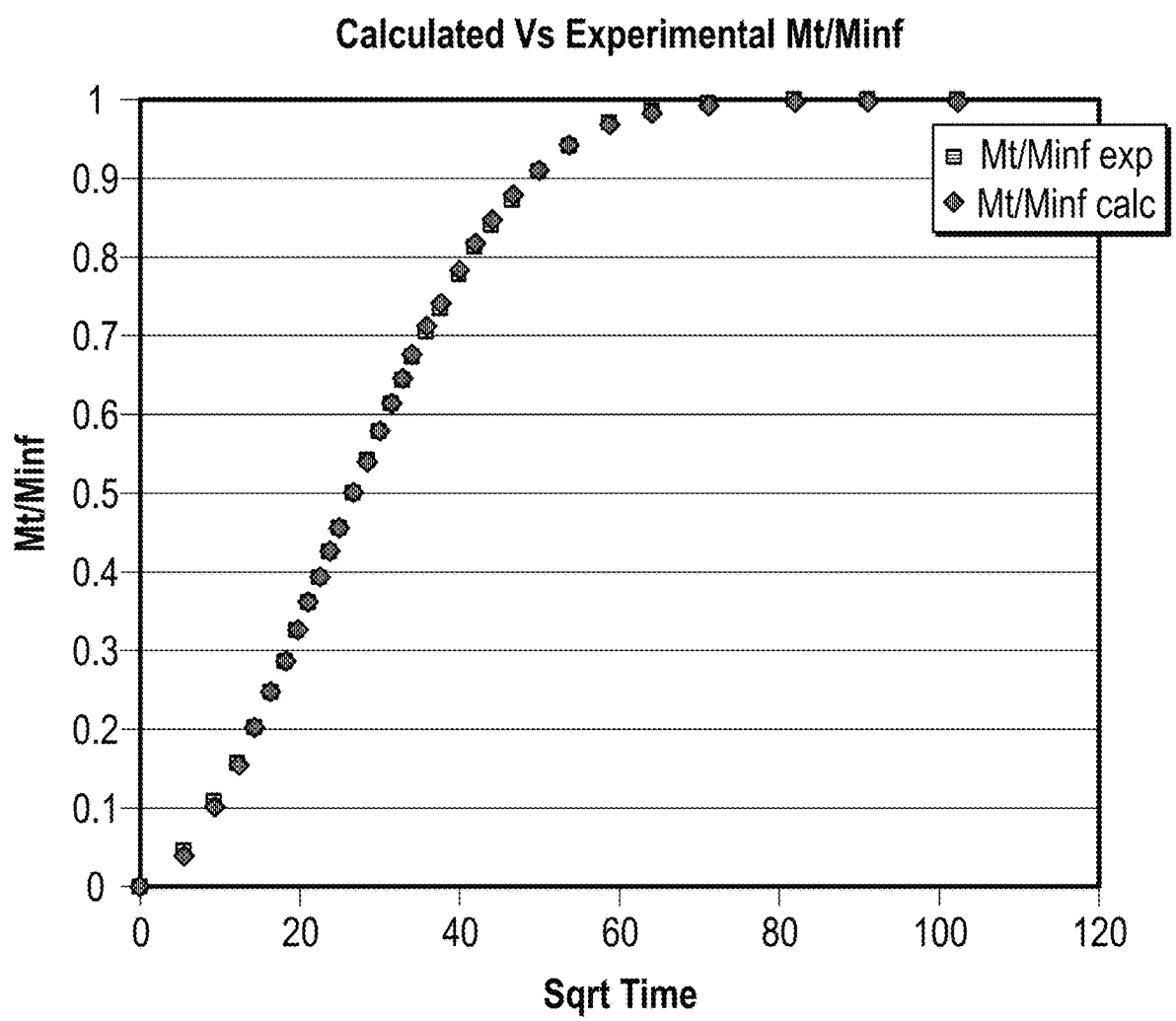
FIG. 20 is a plot of experimental versus calculated desorption curve.

13. Record values of D, L, $A_1$, and $\beta_n$ for n=1 . . . 6. Calculate the full curve using EQ. 9 and calculate and record $R^2$ for the fit. FIG. 20 shows the results of the foregoing calculation method on an infant-sized foamed polymer tube. The tube comprises sample MB-27 6% at 52% void fraction, at a flow rate of 16.7 L/min, RH=100%, D=1.228×10$^{-6}$ cm$^2$/s, and L=3.5697. The $R^2$ of the curve fit was 0.9998.

The foregoing description of the invention includes preferred forms thereof. Modifications may be made thereto without departing from the scope of the invention. To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

What is claimed is:

1. A breathing assistance system comprising:
a gas source configured to transport a gas;
a humidifier configured to humidify the gas from the gas source;
a patient interface configured to provide the gas to a patient; and
an expiratory limb comprising:
an inlet and an outlet; and
a foamed-polymer conduit that is permeable to water vapor and substantially impermeable to liquid water and bulk flow of gas, the foamed-polymer conduit enabling flow of humidified gases from the inlet to the outlet within a space enclosed by the foamed-polymer conduit,
wherein the foamed-polymer conduit is extruded and corrugated,
the foamed-polymer conduit comprises a solid thermoplastic elastomer material and cell voids distributed throughout the solid thermoplastic elastomer material,
the foamed-polymer conduit has a void fraction greater than 25%, and
the foamed-polymer conduit transmits water vapor from the humidified gases within the foamed-polymer conduit to surrounding ambient air through a wall forming at least a portion of the foamed polymer conduit, thereby reducing a build up of condensation within the foamed-polymer conduit.

2. The breathing assistance system of claim 1, wherein the foamed-polymer conduit has a diffusion coefficient of at least 3×10$^{-7}$ cm$^2$/s.

3. The breathing assistance system of claim 1, wherein at least one of the cell voids is connected to another of the cell voids, thereby forming open cell pathways promoting movement of water vapor through the foamed-polymer conduit.

4. The breathing assistance system of claim 3, wherein at least 10% of the cell voids are connected to other cell voids.

5. The breathing assistance system of claim 1, wherein the expiratory limb further comprises a plurality of reinforcing ribs circumferentially arranged around an inner surface of the foamed-polymer conduit and longitudinally aligned along a length of the foamed-polymer conduit between the inlet and the outlet.

6. The breathing assistance system of claim 1, further comprising a heating line along at least a portion of the foamed-polymer conduit.

7. The breathing assistance system of claim 1, wherein at least one of the cell voids is flattened along a longitudinal axis extending between the inlet and the outlet.

8. The breathing assistance system of claim 7, wherein at least 80% of the cell voids have an aspect ratio of longitudinal length to transverse height greater than 2:1.

9. The breathing assistance system of claim 1, wherein the foamed-polymer conduit has a wall thickness within a range of 0.1 mm and 3.0 mm.

10. The breathing assistance system of claim 1, wherein the foamed-polymer conduit has an inner volume having an average void size in a transverse direction less than 30% of a wall thickness of the foamed-polymer conduit.

11. The breathing assistance system of claim 1, wherein a permeability P of the foamed-polymer conduit is at least 60 g-mm/m$^2$/day when measured according to Procedure A of ASTM E96 (using a desiccant method at a temperature of 23° C. and a relative humidity of 90%) and satisfies the formula:

$$P > \exp\{0.019[\ln(M)]^2 - 0.7 \ln(M) + 6.5\}$$

in which M represents an elastic modulus of the foamed polymer in MPa and M is between 30 and 1000 MPa.

12. The breathing assistance system of claim 1, the foamed-polymer conduit comprising an outer skin, adjacent an inner volume, in which the cell voids of the outer skin are closed cell.

13. The breathing assistance system of claim 1, wherein the foamed-polymer conduit is sufficiently stiff, such that the foamed-polymer conduit can be bent around a 25 mm diameter metal cylinder without kinking or collapsing, as defined in a test for increase in flow resistance with bending according to ISO 5367:2000(E).

14. The breathing assistance system of claim 1, wherein the foamed-polymer conduit is configured to be positioned between a ventilator and the patient and configured to deliver humidified gas to the ventilator from the patient.

15. The breathing assistance system of claim 1, wherein the foamed-polymer conduit comprises at least 80% of a length of the expiratory limb.

16. The breathing assistance system of claim 1, wherein the solid thermoplastic elastomer material comprises a copolyester material.

17. The breathing assistance system of claim 16, wherein the copolyester material has a polyether soft segment.

18. A breathing assistance system comprising:
a gas source configured to transport a gas;
a humidifier configured to humidify the gas from the gas source;
a patient interface configured to provide the gas to a patient; and
an expiratory limb comprising:
an inlet and an outlet; and
a foamed-polymer conduit that is permeable to water vapor and substantially impermeable to liquid water and bulk flow of gas, such that the foamed-polymer conduit enables flow of humidified gas from the inlet to the outlet within a space enclosed by the foamed polymer conduit,
wherein the foamed-polymer conduit is extruded and corrugated,
the foamed-polymer conduit comprises a solid thermoplastic elastomer material and cell voids distributed throughout the solid thermoplastic elastomer material,
the foamed-polymer conduit has an inner surface adjacent the enclosed space and an inner volume adjacent the inner surface, said inner volume representing a volume of a wall of said foamed-polymer conduit,
at least one of the cell voids in the inner volume is connected to another of the cell voids, thereby forming open cell pathways promoting movement of water vapor through the wall of the foamed-polymer conduit, and
the foamed polymer conduit further has an outer skin, adjacent the inner volume, in which the cell voids are closed so as to prevent transmission of liquid water and bulk flow of gas.

19. The breathing assistance system of claim 18, wherein the foamed-polymer conduit has a diffusion coefficient of at least $3 \times 10^{-7}$ cm$^2$/s.

20. The breathing assistance system of claim 18, wherein at least 10% of the cell voids are connected.

21. The breathing assistance system of claim 18, further comprising a plurality of reinforcing ribs.

22. The breathing assistance system of claim 21, wherein the reinforcing ribs are longitudinally aligned along at least a portion of the foamed-polymer conduit.

23. The breathing assistance system of claim 18, further comprising a heating line along at least a portion of the foamed-polymer conduit.

24. The breathing assistance system of claim 18, wherein at least one of the cell voids is flattened along a longitudinal axis extending between the inlet and the outlet.

25. The breathing assistance system of claim 24, wherein at least 80% of the cell voids have an aspect ratio of longitudinal length to transverse height greater than 2:1.

26. The breathing assistance system of claim 18, wherein the foamed-polymer conduit has a wall thickness within the range of 0.1 mm and 3.0 mm.

27. The breathing assistance system of claim 18, wherein a permeability P of the foamed-polymer conduit is at least 60 g-mm/m$^2$/day when measured according to Procedure A of ASTM E96 (using a desiccant method at a temperature of 23° C. and a relative humidity of 90%) and satisfies the formula:

$$P > \exp\{0.019[\ln(M)]^2 - 0.7\ln(M) + 6.5\}$$

in which M represents an elastic modulus of the foamed polymer in MPa and M is between 30 and 1000 MPa.

28. The breathing assistance system of claim 18, wherein the foamed-polymer conduit is sufficiently stiff, such that the foamed-polymer conduit is configured to be bent around a 25 mm diameter metal cylinder without kinking or collapsing, as defined in a test for increase in flow resistance with bending according to ISO 5367:2000(E).

29. The breathing assistance system of claim 18, wherein the foamed-polymer conduit comprises at least 80% of a length of the expiratory limb.

30. The breathing assistance system of claim 18, wherein the solid thermoplastic elastomer material comprises a copolyester material.

* * * * *